United States Patent
Burger et al.

(10) Patent No.: US 7,163,924 B2
(45) Date of Patent: Jan. 16, 2007

(54) KETOLIDE DERIVATIVES

(75) Inventors: Matthew Burger, Albany, CA (US);
Daniel Chu, Santa Clara, CA (US)

(73) Assignee: Chiron Corporation, Emeryville, CA (US)

( * ) Notice: Subject to any disclaimer, the term of this patent is extended or adjusted under 35 U.S.C. 154(b) by 342 days.

(21) Appl. No.: 10/831,522

(22) Filed: Apr. 23, 2004

(65) Prior Publication Data
US 2005/0153905 A1 Jul. 14, 2005

Related U.S. Application Data

(60) Provisional application No. 60/465,337, filed on Apr. 25, 2003.

(51) Int. Cl.
*A61K 31/70* (2006.01)
*C07H 17/08* (2006.01)

(52) U.S. Cl. .......................................... 514/29; 536/7.4
(58) Field of Classification Search ................. 536/7.4; 514/29
See application file for complete search history.

(56) References Cited

U.S. PATENT DOCUMENTS

| | | | |
|---|---|---|---|
| 5,635,485 A | 6/1997 | Agouridas et al. ............. | 514/29 |
| 5,656,607 A | 8/1997 | Agouridas et al. ............. | 514/29 |
| 5,750,510 A | 5/1998 | Elliott et al. ................... | 514/29 |
| 5,866,549 A | 2/1999 | Or et al. ........................ | 514/29 |
| 6,063,561 A | 5/2000 | Katz et al. ...................... | 435/4 |
| 6,075,011 A | 6/2000 | Or et al. ........................ | 514/29 |
| 6,100,404 A | 8/2000 | Agouridas et al. ........ | 546/272.7 |
| 6,124,269 A | 9/2000 | Phan et al. .................... | 514/29 |
| 6,147,197 A | 11/2000 | Or et al. ........................ | 536/7.2 |
| 6,756,359 B1 | 6/2004 | Chu et al. ...................... | 514/29 |

FOREIGN PATENT DOCUMENTS

| | | |
|---|---|---|
| EP | 303471 A2 | 2/1989 |
| EP | 945459 A1 | 9/1999 |
| WO | WO 98/42720 | 10/1998 |
| WO | WO 99/35157 | 7/1999 |
| WO | WO 00/69875 | 11/2000 |
| WO | WO 03/004509 | 1/2003 |

OTHER PUBLICATIONS

Denis et al. "Beta-Keto-Ester Chemistry and Ketolides. Synthesis and Antibacterial Activity of 2-Halogeno, 2 Methyl and 2,3 Enol-Ether Ketolides" *Bioorganic Medicinal Chemistry Letters* 10:2019-2022, 2000.
Hauske et al., "Aglycon Modifications of Erythromycin A: Regiospecific and Stereospecific Elaboration of the C-12 Position" *J. Org. Chem.* 52(20):4622-4625, 1987.
Jacobsen et al., "Precursor-Directed Biosynthesis of 12-Ethyl Erythromycin" *Bioogranic and Medicinal Chemistry* 6:1171-1177, 1998.
Lartey et al., "Synthesis and Activity of C-21 Alkylamino Derivatives of (9R)-Erythromycylamine" *J. Antibiotics* 45 (3):380-385, 1992.

*Primary Examiner*—Elli Peselev
(74) *Attorney, Agent, or Firm*—Hugo Eng; Young J. Suh; Alisa A. Harbin

(57) ABSTRACT

Antimicrobial ketolide compounds are provided having the formula (A):

as well as pharmaceutically acceptable salts, esters or prodrugs thereof, pharmaceutical compositions comprising such compounds, methods of treating bacterial infections by the administration of such compounds, and processes for the preparation of the compounds.

35 Claims, No Drawings

KETOLIDE DERIVATIVES

CROSS-REFERENCE TO RELATED APPLICATION

This application claims priority to U.S. Provisional Application Ser. No. 60/465,337 filed on Apr. 25, 2003. The disclosure of the above provisional application is herein incorporated by reference in its entirety and for all purposes as if fully set forth herein.

FIELD OF THE INVENTION

This invention relates to novel semi-synthetic ketolides having antibacterial activity. In another aspect, the present invention relates to pharmaceutical compositions comprising these compounds and to a medical method of treatment employing these compositions. More particularly, this invention concerns pyridyl substituted ketolides, compositions containing these compounds, methods of producing the compounds, and methods of treating bacterial infections.

BACKGROUND OF THE INVENTION

Erythromycins A through D, represented by formula (I),

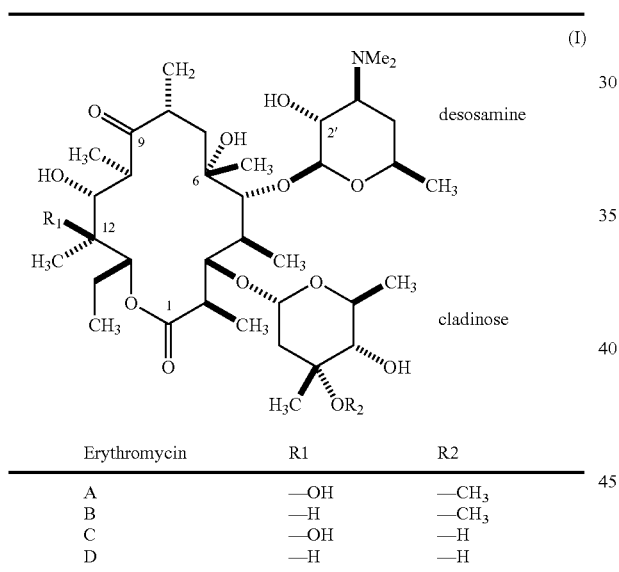

| Erythromycin | R1 | R2 |
|---|---|---|
| A | —OH | —CH₃ |
| B | —H | —CH₃ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess Gram-negative activity, or which possess unexpected selectivity against target microorganisms. Consequently, numerous investigators have prepared chemical derivatives of erythromycin in an attempt to obtain analogs having modified or improved profiles of antibiotic activity. For example, the compound 6-OMe erythromycin A, or clarithromycin, has found widespread use. However, even this compound is beginning to lose its effectiveness and other erythromycin derivatives having improved activity are needed. Other 6-O-substituted erythromycin compounds have also been proposed for this purpose. For example, PCT application WO 92/09614, published Jun. 11, 1992, discloses tricyclic 6-O-methylerythromycin A derivatives. U.S. Pat. No. 5,444,051 discloses 6-O-substituted-3-oxoerythromycin A derivatives in which the substituents are selected from alkyl, —CONH₂, —CONHC(O)alkyl and —CONHSO₂ alkyl. PCT application WO 97/10251, published Mar. 20, 1997, discloses 6-O-methyl 3-descladinose erythromycin derivatives. European Patent Application 596802, published May 11, 1994, discloses bicyclic 6-O-methyl-3-oxoerythromycin A derivatives.

More recently, a class of 3-O ketolide erythromycin derivatives have been disclosed in U.S. Pat. Nos. 6,147,197 and 5,635,485. Representative lead compounds in this class include, for example ABT-773 disclosed in U.S. Pat. No. 6,147,197 and telithromycin disclosed in U.S. Pat. No. 5,635,485. The structures of these compounds are as follows:

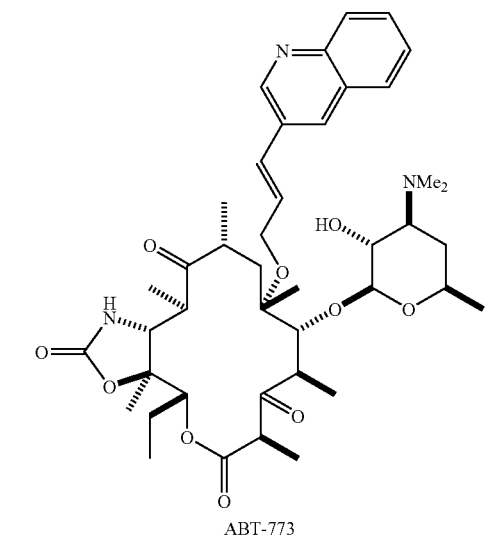

ABT-773

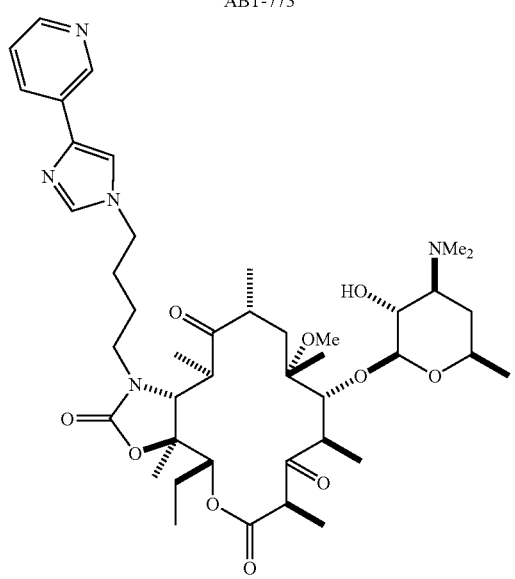

Telithromycin

Other modifications that have shown promise include modifications at C₂, including, for example, those shown in U.S.

Pat. No. 6,124,269 and International Application Publication No. WO 00/69875, the disclosures of which are incorporated herein by reference.

U.S. Pat. Nos. 5,635,485 and 6,100,404 (the disclosures of which are incorporated herein by reference) disclose ketolide derivatives of formula (I):

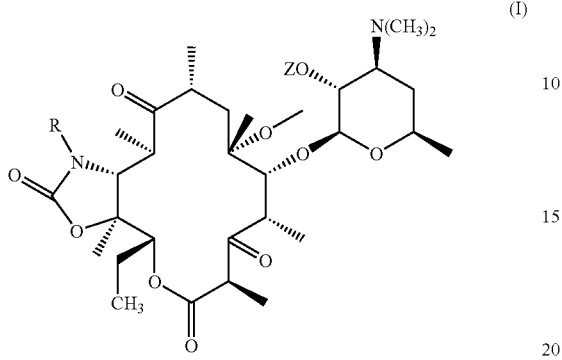

Presented herein are novel substituted pyridyl ketolide derivatives. The inventors have unexpectedly discovered that substituted pyridine side chains impart improved pharmacokinetic properties relative to the unsubstituted pyridyl ketolide derivatives, thus providing a better therapeutic index and better dosing regimen.

There exists a continuing medical need to identify new ketolide derivatives that possess improved antibacterial activity, less potential for developing resistance, activity against Gram-negative bacteria, increased selectivity against target microorganisms, as well as a better safety profile. In an effort to address that need, the inventors herein have prepared chemical derivatives of ketolides to obtain analogs having modified and/or improved pharmacokinetic profiles over ketolide compounds known in the art.

SUMMARY OF THE INVENTION

The present invention provides novel ketolide derivatives having novel pyridyl substituents. The present invention also provides useful common intermediates, methods for their synthesis, and methods of use of such compounds for the treatment and/or prophylaxis of diseases, especially bacterial infections.

In one embodiment, the present invention provides a compound having the formula (A):

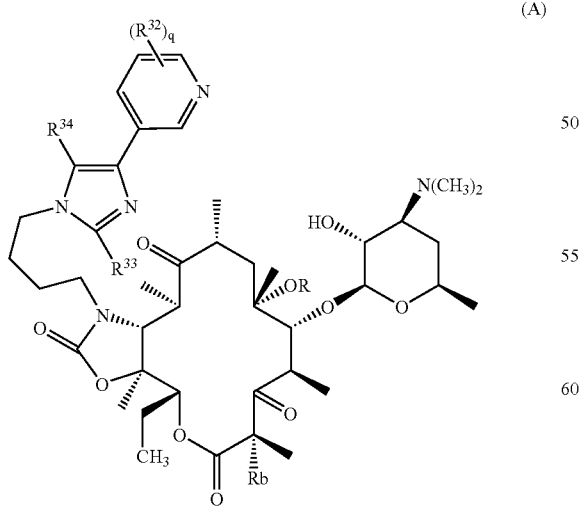

or a pharmaceutically acceptable salt, ester or prodrug thereof, wherein

A) R is selected from the group consisting of
  (1) hydrogen;
  (2) methyl substituted with a moiety selected from the group consisting of
    (a) —CN,
    (b) —F,
    (c) —$CO_2R^{10}$, wherein $R^{10}$ is $C_1$–$C_3$-alkyl or aryl substituted with $C_1$–$C_3$-alkyl, or heteroaryl substituted with $C_1$–$C_3$-alkyl,
    (d) —$S(O)_nR^{10}$—, wherein n is 0, 1, or 2 and $R^{10}$ is as previously defined,
    (e) —NH—C(O)$R^{10}$, wherein $R^{10}$ is as previously defined,
    (f) —NH—C(O)$NR^{11}R^{12}$, wherein $R^{11}$ and $R^{12}$ are independently selected from hydrogen, $C_1$–$C_3$-alkyl, $C_1$–$C_3$-alkyl substituted with aryl, substituted aryl, heteroaryl, and substituted heteroaryl,
    (g) aryl,
    (h) substituted aryl,
    (i) heteroaryl, and
    (j) substituted heteroaryl;
  (3) $C_1$–$C_{12}$ alkyl;
  (4) $C_2$–$C_{12}$-alkyl substituted with one or more substituents selected from the group consisting of
    (a) halogen,
    (b) hydroxy,
    (c) $C_1$–$C_3$-alkoxy,
    (d) $C_1$–$C_3$-alkoxy-$C_1$–$C_3$-alkoxy,
    (e) oxo,
    (f) —O—$SO_2$—(substituted $C_1$–$C_6$-alkyl),
    (g) —$N_3$,
    (h) —CHO,
    (i) —$NR^{13}R^{14}$, wherein $R^{13}$ and $R^{14}$ are selected from the group consisting of
      (i) hydrogen,
      (ii) $C_1$–$C_{12}$-alkyl,
      (iii) substituted $C_1$–$C_{12}$-alkyl,
      (iv) $C_2$–$C_{12}$-alkenyl,
      (v) substituted $C_2$–$C_{12}$-alkenyl,
      (vi) $C_2$–$C_{12}$-alkynyl,
      (vii) substituted $C_2$–$C_{12}$-alkynyl,
      (viii) aryl,
      (ix) $C_3$–$C_8$-cycloalkyl,
      (x) substituted $C_3$–$C_8$-cycloalkyl,
      (xi) substituted aryl,
      (xii) $C_3$–$C_{12}$-heterocycloalkyl,
      (xiii) substituted $C_3$–$C_{12}$-heterocycloalkyl,
      (xiv) $C_1$–$C_{12}$-alkyl substituted with aryl,
      (xv) $C_1$–$C_{12}$-alkyl substituted with substituted aryl,
      (xvi) $C_1$–$C_{12}$-alkyl substituted with $C_3$–$C_{12}$-heterocycloalkyl,
      (xvii) $C_1$–$C_{12}$-alkyl substituted with substituted $C_3$–$C_{12}$-heterocycloalkyl,
      (xviii) $C_1$–$C_{12}$-alkyl substituted with $C_3$–$C_8$-cycloalkyl,
      (xix) $C_1$–$C_{12}$-alkyl substituted with substituted $C_3$–$C_8$-cycloalkyl,
      (xx) heteroaryl,
      (xxi) substituted heteroaryl,
      (xxii) $C_1$–$C_{12}$-alkyl substituted with heteroaryl, and
      (xxiii) $C_1$–$C_{12}$-alkyl substituted with substituted heteroaryl; or $R^{13}$ and $R^{14}$ are taken together with the atom to which they are attached to form a 3- to 10-membered heterocycloalkyl ring which may optionally be substituted with one or more substituents independently selected from the group consisting of
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(viii) $C_1$–$C_3$-alkoxy-$C_1$–$C_3$-alkyl;
(j) —$CO_2R^{10}$, wherein $R^{10}$ is as previously defined,
(k) —$C(O)NR^{11}R^{12}$, wherein $R^{11}$ and $R^{12}$ are as previously defined,
(l) =N—O—$R^{10}$, wherein $R^{10}$ is as previously defined,
(m) —CN,
(n) —O—$S(O)_nR^{10}$ wherein n is 0, 1, or 2 and $R^{10}$ is as previously defined,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) $C_3$–$C_{12}$-heterocycloalkyl,
(w) substituted $C_3$–$C_{12}$-heterocycloalkyl,
(x) —NH—$C(O)R^{10}$, wherein $R^{10}$ is as previously defined,
(y) —NH—$C(O)NR^{11}R^{12}$, wherein $R^{11}$ and $R^{12}$ are as previously defined,
(z) =N—$NR^{13}R^{14}$, wherein $R^{13}$ and $R^{14}$ are as previously defined,
(aa) =N—$R^9$, wherein $R^9$ is selected from the group consisting of:
(i) $C_1$–$C_{12}$-alkyl optionally substituted with a substituent selected from the group consisting of
(a) aryl,
(b) substituted aryl,
(c) heteroaryl, and
(d) substituted heteroaryl,
(ii) aryl,
(iii) substituted aryl,
(iv) heteroaryl,
(v) substituted heteroaryl, and
(vi) $C_3$–$C_{12}$-heterocycloalkyl,
(bb) =N—NH—$C(O)R^{10}$, wherein $R^{10}$ is as previously defined, and
(cc) =N—NH—$C(O)NR^{11}R^{12}$, wherein $R^{11}$ and $R^{12}$ are as previously defined;
(5) $C_3$-alkenyl substituted with a moiety selected from the group consisting of
(a) hydrogen,
(b) halogen,
(c) —CHO,
(d) —$CO_2R^{10}$, wherein $R^{10}$ is as previously defined,
(e) —$C(O)NR^{11}R^{12}$, wherein $R^{11}$ and $R^{12}$ are as previously defined,
(f) —$C(O)R^9$, wherein $R^9$ is previously defined,
(g) —CN,
(h) aryl,
(i) substituted aryl,
(j) heteroaryl,
(k) substituted heteroaryl,
(l) —$C_3$–$C_8$-Cycloalkyl, and
(m) —$C_1$–$C_{12}$-alkyl substituted with heteroaryl;
(6) $C_4$–$C_{10}$-alkenyl;

(7) $C_4$–$C_{10}$-alkenyl substituted with one or more substituents selected from the group consisting of
(a) halogen,
(b) —$C_1$–$C_3$-alkoxy,
(c) oxo,
(d) —CHO,
(e) —$CO_2R^{10}$, wherein $R^{10}$ is as previously defined,
(f) —$C(O)NR^{11}R^{12}$, wherein $R^{11}$ and $R^{12}$ are as previously defined,
(g) —$NR^{13}R^{14}$, wherein $R^{13}$ and $R^{14}$ are as previously defined,
(h) =N—O—$R^{10}$, wherein $R^{10}$ is as previously defined,
(i) —CN,
(j) —O—$S(O)_nR^{10}$, wherein n is 0, 1, or 2 and $R^{10}$ is as previously defined,
(k) aryl,
(l) substituted aryl,
(m) heteroaryl,
(n) substituted heteroaryl,
(o) —$C_3$–$C_8$-cycloalkyl,
(p) —$C_1$–$C_{12}$-alkyl substituted with substituted heteroaryl,
(q) —NH—$C(O)R^{10}$, wherein $R^{10}$ is as previously defined,
(r) —NH—$C(O)NR^{12}R^{12}$, wherein $R^{11}$ and $R^{12}$ are as previously defined,
(s) =N—$NR^{13}R^{14}$, wherein $R^{13}$ and $R^{14}$ are as previously defined,
(t) =N—$R^9$, wherein $R^9$ is as previously defined,
(u) =N—NH—$C(O)R^{10}$, wherein $R^{10}$ is as previously defined, and
(v) =N—NH—$C(O)NR^{11}R^{12}$, wherein $R^{11}$ and $R^{12}$ are as previously defined;
(8) $C_3$–$C_{10}$-alkynyl;
(9) $C_3$–$C_{10}$-alkynyl substituted with one or more substituents selected from the group consisting of
(a) $C_1$–$C_{12}$-trialkylsilyl,
(b) aryl,
(c) substituted aryl,
(d) heteroaryl, and
(e) substituted heteroaryl; and
(10) $C(O)NR^7R^8$, wherein $R^7$ and $R^8$ are independently selected from hydrogen, $C_1$–$C_{12}$-alkyl, and substituted $C_1$–$C_{12}$-alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH, —N($C_1$–$C_6$-alkyl)-, —N(aryl)-, —N(aryl–$C_1$–$C_6$-alkyl-)-, —N(substituted aryl–$C_1$–$C_6$-alkyl-)-, —N(heteroaryl)-, —N(heteroaryl–$C_1$–$C_6$-alkyl-)-, —N(substituted heteroaryl–$C_1$–$C_6$-alkyl-)-, and —S— or —$S(O)_n$— wherein n is 1 or 2;
B) Rb is hydrogen, halogen, $C_1$–$C_{12}$ alkyl, substituted $C_1$–$C_{12}$-alkyl, or $C_1$–$C_{12}$-alkyl further substituted with one or more halogen groups;
C) Each $R^{32}$ is independently selected from the group consisting of a free, salified, esterified and amidified
(1) carboxyl, hydroxyl, halogen, —$NO_2$, —CN, $C_1$–$C_{12}$-alkyl, $C_3$–$C_{12}$-cycloalkyl, $C_2$–$C_{12}$-alkenyl, $C_2$–$C_{12}$-alkynyl, O-alkyl, O-alkenyl, O-alkynyl, S-alkyl, S-alkenyl, S-alkynyl, N-alkyl, N-alkenyl, and N-alkynyl of up to 12 carbon atoms optionally substituted by one or more halogens;

(2) —NR²¹ (R²²),
  wherein R²¹ and R²² are individually hydrogen or C₁–C₁₂-alkyl;
(3) —C(O)R²³,
  wherein R²³ is C₁–C₁₂-alkyl; and
(4) optionally substituted heteroaryl, O-aryl, S-aryl, and O-substituted-C₁–C₁₂ alkyl, or S-substituted-C₁–C₁₂ alkyl;
D) q is 0, 1, 2, 3, or 4; and
E) R³³ and R³⁴ are independently selected from the group consisting of hydrogen, halogen, C₁–C₁₂ alkyl, and substituted C₁–C₁₂-alkyl;
  with the proviso that when q is 0, then R³³ and R³⁴ are not both hydrogen.

The present invention also provides pharmaceutical compositions that comprise a therapeutically effective amount of a compound as defined above in combination with a pharmaceutically acceptable carrier.

The invention further provides a method of treating bacterial infections in a patient in need thereof comprising administering a therapeutically effective amount of a compound of the invention as defined above to the patient, together with a pharmaceutically acceptable carrier. Patients include mammals such as humans, cats, or dogs.

The invention also provides for the use of a compound of the invention as described above in the manufacture of a medicament for the treatment or prophylaxis of bacterial infections.

DETAILED DESCRIPTION OF THE INVENTION

Abbreviations

Abbreviations which have been used in the descriptions of the scheme and the examples that follow are: Ac for acetyl; AcOH for acetic acid; AIBN for azobisisobutyronitrile; Bu₃SnH for tributyltin hydride; CDI for carbonyldiimidazole; DBU for 1,8-diazabicyclo[5.4.0]undec-7-ene; DCM for dichloromethane; DEAD for diethylazodicarboxylate; DMF for dimethylformamide; DMP for 2,2-dimethoxypropane DMSO for dimethylsulfoxide; DPPA for diphenylphosphoryl azide; Et for ethyl; Et₃N for triethylamine; EtOAc for ethyl acetate; Et₂O for diethyl ether; EtOH for ethanol; HOAc for acetic acid; LiHMDS or LiN(TMS)₂ for lithium bis(trimethylsilyl)amide; MCPBA for meta-chloroperbenzoic acid; Me for methyl; MeOH for methanol; MsCl for methanesulfonyl chloride; NaHMDS or NaN(TMS)₂ for sodium bis(trimethylsilyl)amide; NMO for N-methylmorpholine N-oxide; SOCl₂ for thionyl chloride; PPTS for pyridium p-toluene sulfonate; Py for pyridine; TEA for triethylamine; THF for tetrahydrofuran; TMSCl for trimethylsilyl chloride; TMSCF₃ for trimethyl(trifluoromethyl)-silane; TPP for triphenylphosphine; TPAP for tetra-n-propylammonium perruthenate; DMAP for 4-dimethylamino pyridine, TsOH for p-toluene sulfonic acid.

In one embodiment, the present invention provides a compound having the formula (A):

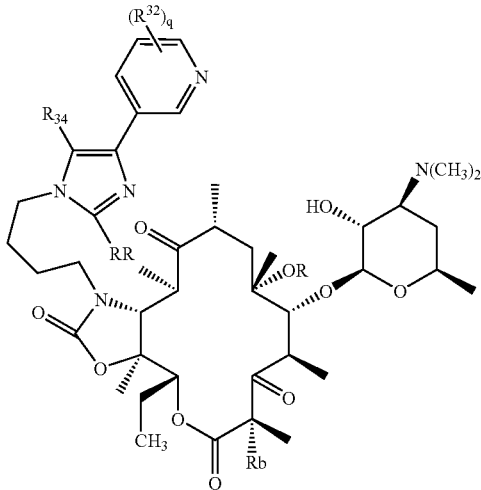

(A)

or a pharmaceutically acceptable salt, ester or prodrug thereof, wherein
A) R is selected from the group consisting of
  (1) hydrogen;
  (2) methyl substituted with a moiety selected from the group consisting of
    (a) —CN,
    (b) —F,
    (c) —CO₂R¹⁰, wherein R¹⁰ is C₁–C₃-alkyl or aryl substituted with C₁–C₃-alkyl, or heteroaryl substituted with C₁–C₃-alkyl,
    (d) —S(O)$_n$R¹⁰—, wherein n is 0, 1, or 2 and R¹⁰ is as previously defined,
    (e) —NH—C(O)R¹⁰, wherein R¹⁰ is as previously defined,
    (f) —NH—C(O)NR¹¹R¹², wherein R¹¹ and R¹² are independently selected from hydrogen, C₁–C₃-alkyl, C₁–C₃-alkyl substituted with aryl, substituted aryl, heteroaryl, and substituted heteroaryl,
    (g) aryl,
    (h) substituted aryl,
    (i) heteroaryl, and
    (j) substituted heteroaryl;
  (3) C₁–C₁₂ alkyl;
  (4) C₂–C₁₂-alkyl substituted with one or more substituents selected from the group consisting of
    (a) halogen,
    (b) hydroxy,
    (c) C₁–C₃-alkoxy,
    (d) C₁–C₃-alkoxy-C₁–C₃-alkoxy,
    (e) oxo,
    (f) —O—SO₂-(substituted C₁–C₆-alkyl),
    (g) —N₃,
    (h) —CHO,
    (i) —NR¹³R¹⁴, wherein R¹³ and R¹⁴ are selected from the group consisting of
      (i) hydrogen,
      (ii) C₁–C₁₂-alkyl,
      (iii) substituted C₁–C₁₂-alkyl,
      (iv) C₂–C₁₂-alkenyl,
      (v) substituted C₂–C₁₂-alkenyl, (vi) $C_2$–$C_{12}$-alkynyl,
(vii) substituted $C_2$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) $C_3$–$C_{12}$-heterocycloalkyl,
(xiii) substituted $C_3$–$C_{12}$-heterocycloalkyl,
(xiv) $C_1$–$C_{12}$-alkyl substituted with aryl,
(xv) $C_1$–$C_{12}$-alkyl substituted with substituted aryl,
(xvi) $C_1$–$C_{12}$-alkyl substituted with $C_3$–$C_{12}$-heterocycloalkyl,
(xvii) $C_1$–$C_{12}$-alkyl substituted with substituted $C_3$–$C_{12}$-heterocycloalkyl,
(xviii) $C_1$–$C_{12}$-alkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and
(xxiii) $C_1$–$C_{12}$-alkyl substituted with substituted heteroaryl;
    or $R^{13}$ and $R^{14}$ are taken together with the atom to which they are attached to form a 3- to 10-membered heterocycloalkyl ring which may optionally be substituted with one or more substituents independently selected from the group consisting of
(i) halogen,
(ii) hydroxy,
(iii) $C_1$–$C_3$-alkoxy,
(iv) $C_1$–$C_3$-alkoxy–$C_1$–$C_3$-alkoxy,
(v) oxo,
(vi) $C_1$–$C_3$-alkyl,
(vii) halo-$C_1$–$C_3$-alkyl, and
(viii) $C_1$–$C_3$-alkoxy–$C_1$–$C_3$-alkyl;
(j) —$CO_2R^{10}$, wherein $R^{10}$ is as previously defined,
(k) —$C(O)NR^{11}R^{12}$, wherein $R^{11}$ and $R^{12}$ are as previously defined,
(l) =N—O—$R^{10}$, wherein $R^{10}$ is as previously defined,
(m) —CN,
(n) —O—$S(O)_nR^{10}$ wherein n is 0, 1, or 2 and $R^{10}$ is as previously defined,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) $C_3$–$C_{12}$-heterocycloalkyl,
(w) substituted $C_3$–$C_{12}$-heterocycloalkyl,
(x) —NH—$C(O)R^{10}$, wherein $R^{10}$ is as previously defined,
(y) —NH—$C(O)NR^{11}R^{12}$, wherein $R^{11}$ and $R^{12}$ are as previously defined,
(z) =N—$NR^{13}R^{14}$, wherein $R^{13}$ and $R^{14}$ are as previously defined,
(aa) =N—$R^9$, wherein $R^9$ is selected from the group consisting of:
  (i) $C_1$–$C_{12}$-alkyl optionally substituted with a substituent selected from the group consisting of
    (a) aryl,
    (b) substituted aryl,
    (c) heteroaryl, and
    (d) substituted heteroaryl,
  (ii) aryl,
  (iii) substituted aryl,
  (iv) heteroaryl,
  (v) substituted heteroaryl, and
  (vi) $C_3$–$C_{12}$-heterocycloalkyl,
(bb) =N—NH—$C(O)R^{10}$, wherein $R^{10}$ is as previously defined, and
(cc) =N—NH—$C(O)NR^{11}R^{12}$, wherein $R^{11}$ and $R^{12}$ are as previously defined;
(5) $C_3$-alkenyl substituted with a moiety selected from the group consisting of
(a) hydrogen,
(b) halogen,
(c) —CHO,
(d) —$CO_2R^{10}$, wherein $R^{10}$ is as previously defined,
(e) —$C(O)NR^{11}R^{12}$, wherein $R^{11}$ and $R^{12}$ are as previously defined,
(f) —$C(O)R^9$, wherein $R^9$ is as previously defined,
(g) —CN,
(h) aryl,
(i) substituted aryl,
(j) heteroaryl,
(k) substituted heteroaryl,
(l) —$C_3$–$C_8$-cycloalkyl, and
(m) —$C_1$–$C_{12}$-alkyl substituted with heteroaryl;
(6) $C_4$–$C_{10}$-alkenyl;
(7) $C_4$–$C_{10}$-alkenyl substituted with one or more substituents selected from the group consisting of
(a) halogen,
(b) —$C_1$–$C_3$-alkoxy,
(c) oxo,
(d) —CHO,
(e) —$CO_2R^{10}$, wherein $R^{10}$ is as previously defined,
(f) —$C(O)NR^{11}R^{12}$, wherein $R^{11}$ and $R^{12}$ are as previously defined,
(g) —$NR^{13}R^{14}$, wherein $R^{13}$ and $R^{14}$ are as previously defined,
(h) =N—O—$R^{10}$, wherein $R^{10}$ is as previously defined,
(i) —CN,
(j) —O—$S(O)_nR^{10}$, wherein n is 0, 1, or 2 and $R^{10}$ is as previously defined,
(k) aryl,
(l) substituted aryl,
(m) heteroaryl,
(n) substituted heteroaryl,
(o) —$C_3$–$C_8$-cycloalkyl,
(p) —$C_1$–$C_{12}$-alkyl substituted with substituted heteroaryl,
(q) —NH—$C(O)R^{10}$, wherein $R^{10}$ is as previously defined,
(r) —NH—$C(O)NR^{11}R^{12}$, wherein $R^{11}$ and $R^{12}$ are as previously defined,
(s) =N—$NR^{13}R^{14}$, wherein $R^{13}$ and $R^{14}$ are as previously defined,
(t) =N—$R^9$, wherein $R^9$ is as previously defined,
(u) =N—NH—$C(O)R^{10}$, wherein $R^{10}$ is as previously defined, and
(v) =N—NH—$C(O)NR^{11}R^{12}$, wherein $R^{11}$ and $R^{12}$ are as previously defined;
(8) $C_3$–$C_{10}$-alkynyl;
(9) $C_3$–$C_{10}$-alkynyl substituted with one or more substituents selected from the group consisting of
(a) $C_1$–$C_{12}$-trialkylsilyl,
(b) aryl, (c) substituted aryl,
(d) heteroaryl, and
(e) substituted heteroaryl; and
(10) C(O)NR$^7$R$^8$, wherein R$^7$ and R$^8$ are independently selected from hydrogen, C$_1$–C$_{12}$-alkyl, and substituted C$_1$–C$_{12}$-alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH, —N(C$_1$–C$_6$-alkyl)-, —N(aryl)-, —N(aryl-C$_1$–C$_6$-alkyl-)-, —N(substituted aryl-C$_1$–C$_6$-alkyl-)-, —N(heteroaryl)-, —N(heteroaryl-C$_1$–C$_6$-alkyl-)-, —N(substituted heteroaryl-C$_1$–C$_6$-alkyl-)-, and —S— or —S(O)$_n$— wherein n is 1 or 2;

B) Rb is hydrogen, halogen, C$_1$–C$_{12}$ alkyl, substituted C$_1$–C$_{12}$-alkyl, or C$_1$–C$_{12}$-alkyl further substituted with one or more halogen groups;

C) Each R$^{32}$ is independently selected from the group consisting of a free, salified, esterified and amidified
(1) carboxyl, hydroxyl, halogen, —NO$_2$, —CN, C$_1$–C$_{12}$-alkyl, C$_3$–C$_{12}$-cycloalkyl, C$_2$–C$_{12}$-alkenyl, C$_2$–C$_{12}$-alkynyl, O-alkyl, O-alkenyl, O-alkynyl, S-alkyl, S-alkenyl, S-alkynyl, N-alkyl, N-alkenyl, and N-alkynyl of up to 12 carbon atoms optionally substituted by one or more halogens;
(2) —NR$^{21}$(R$^{22}$),
wherein R$^{21}$ and R$^{22}$ are individually hydrogen or C$_1$–C$_{12}$-alkyl;
(3) —C(O)R$^{23}$,
wherein R$^{23}$ is C$_1$–C$_{12}$-alkyl; and
(4) optionally substituted heteroaryl, O-aryl, S-aryl, and O-substituted-C$_1$–C$_{12}$ alkyl, or S-substituted-C$_1$–C$_{12}$ alkyl;

D) q is 0, 1, 2, 3, or 4; and

E) R$^{33}$ and R$^{34}$ are independently selected from the group consisting of hydrogen, halogen, C$_1$–C$_{12}$ alkyl, and substituted C$_1$–C$_{12}$-alkyl;
with the proviso that when q is 0, then R$^{33}$ and R$^{34}$ are not both hydrogen.

In some embodiments, the present invention provides compound of formula (A) above, wherein
A) R is methyl;
B) Rb is hydrogen or halogen;
C) Each R$^{32}$ is independently selected from the group consisting of halogen, C$_1$–C$_{12}$-alkyl, C$_1$–C$_{12}$-alkoxy, C$_1$–C$_{12}$-alkylalkoxy, amino, and —NR$^{21}$(R$^{22}$); and
D) R$^{33}$ and R$^{34}$ are independently selected from the group consisting of hydrogen and C$_1$–C$_{12}$-alkyl.

In some embodiments, the invention provides compounds of formula A wherein R is methyl.

In still other embodiments, the invention provides compounds of formula A wherein Rb is fluorine.

In some embodiments, the invention provides compounds of formula A wherein at least one of R$^{32}$ is 2-chloro, 6-chloro, 2-fluoro, or 6-fluoro.

In some embodiments, the invention provides compounds of formula A wherein R$^{32}$ is methyl. In yet other embodiments, the invention provides compounds of formula A wherein at least one of R$^{32}$ is 5-methyl or 6-methyl.

In some further embodiments, the invention provides compounds of formula A wherein at least one of R$^{32}$ is methoxy or ethoxy. In some particular embodiments, the invention provides compounds of formula A wherein at least one of R$^{32}$ is 4-methoxy, 6-methoxy, or 4-ethoxy.

In still some further embodiments, the invention provides compounds of formula A wherein at least one of R$^{32}$ is amino, methylamino, or dimethylamino. In some particular embodiments, the invention provides compounds of formula A wherein at least one of R$^{32}$ is 6-amino, 6-methylamino, or 6-dimethylamino.

In other embodiments, the invention provides compounds of formula A wherein R$^{33}$ is methyl.

In still other embodiments, the invention provides compounds of formula A wherein R$^{34}$ is methyl.

In another embodiment, the present invention provides compounds having the structure of the following formula (B):

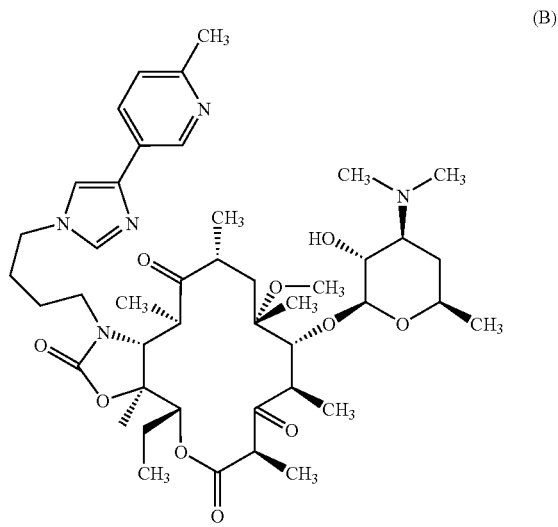

(B)

or a pharmaceutically acceptable salt, ester or prodrug thereof.

In another embodiment, the present invention provides compounds having the structure of the following formula (C):

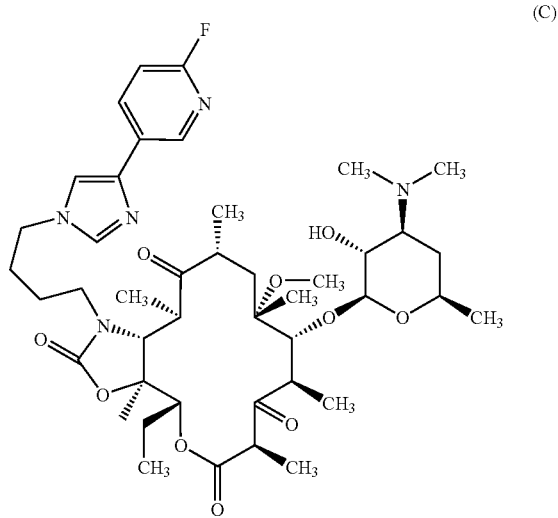

(C)

or a pharmaceutically acceptable salt, ester or prodrug thereof.

In another embodiment, the present invention provides compounds having the structure of the following formula (D):

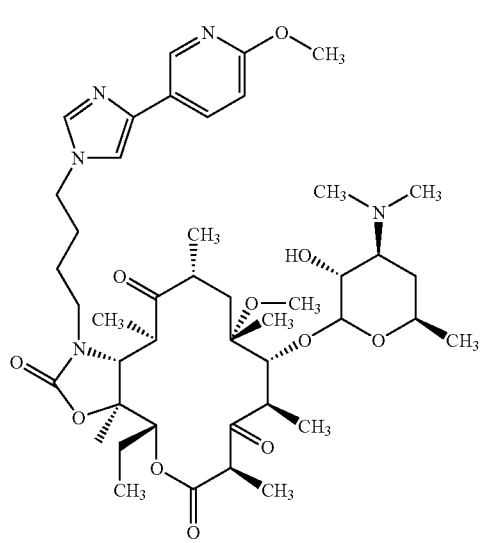

or a pharmaceutically acceptable salt, ester or prodrug thereof.

In another embodiment, the present invention provides compounds having the structure of the following formula (E):

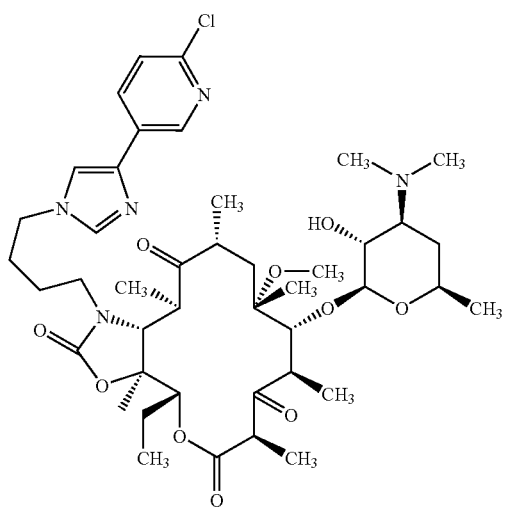

or a pharmaceutically acceptable salt, ester or prodrug thereof.

In another embodiment, the present invention provides compounds having the structure of the following formula (F):

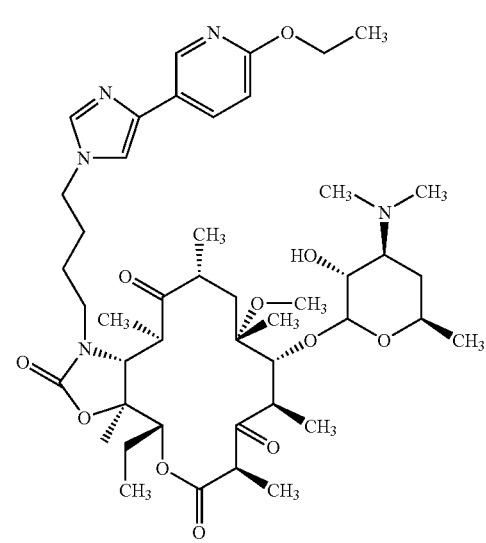

or a pharmaceutically acceptable salt, ester or prodrug thereof.

In another embodiment, the present invention provides compounds having the structure of the following formula (G):

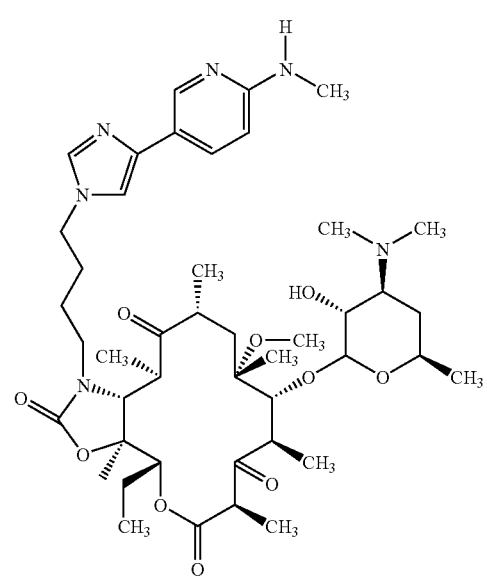

or a pharmaceutically acceptable salt, ester or prodrug thereof.

In another embodiment, the present invention provides compounds having the structure of the following formula (H):

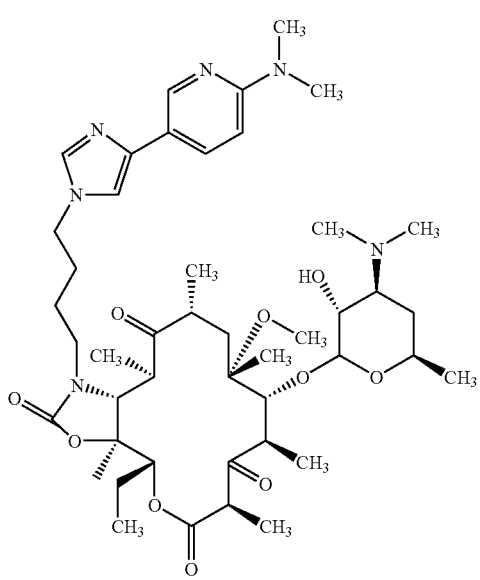

(H)

or a pharmaceutically acceptable salt, ester or prodrug thereof.

In another embodiment, the present invention provides compounds having the structure of the following formula (I):

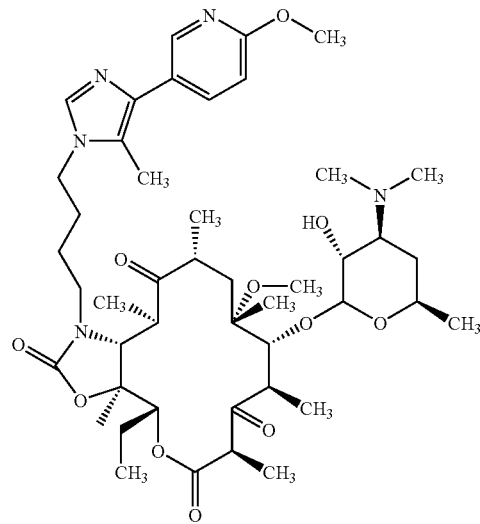

(I)

or a pharmaceutically acceptable salt, ester or prodrug thereof.

In another embodiment, the present invention provides compounds having the structure of the following formula (J):

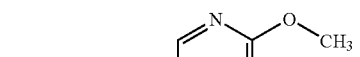
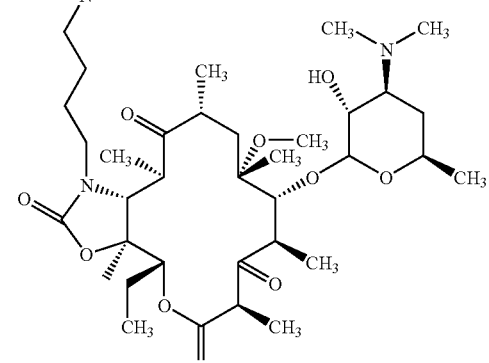

(J)

or a pharmaceutically acceptable salt, ester or prodrug thereof.

In another embodiment, the present invention provides compounds having the structure of the following formula (K):

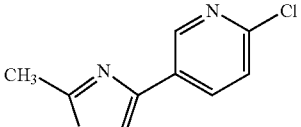
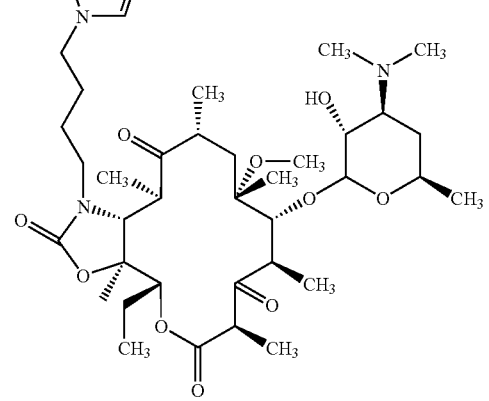

(K)

or a pharmaceutically acceptable salt, ester or prodrug thereof.

In another embodiment, the present invention provides compounds having the structure of the following formula (L):

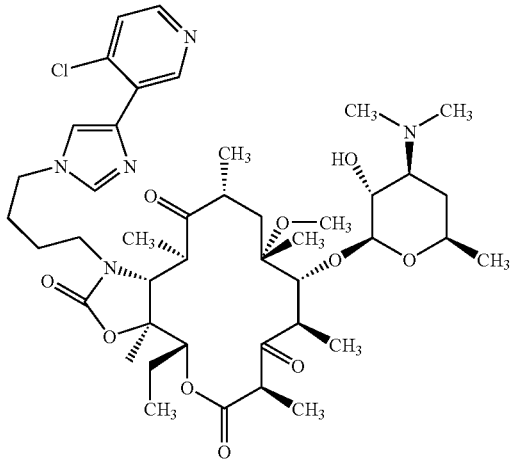

or a pharmaceutically acceptable salt, ester or prodrug thereof.

In another embodiment, the present invention provides compounds having the structure of the following formula (M):

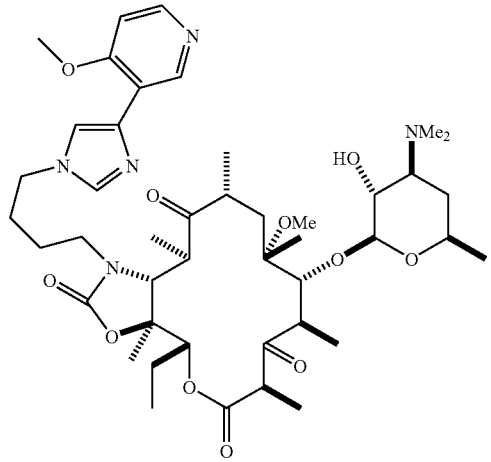

or a pharmaceutically acceptable salt, ester or prodrug thereof.

In another embodiment, the present invention provides compounds having the structure of the following formula (N):

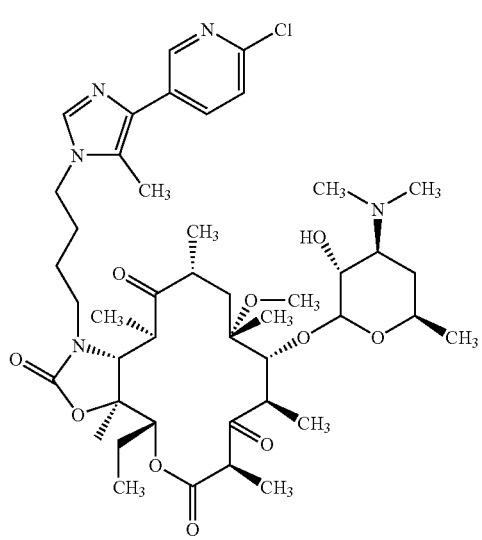

or a pharmaceutically acceptable salt, ester or prodrug thereof.

In another embodiment, the present invention provides compounds having the structure of the following formula (O):

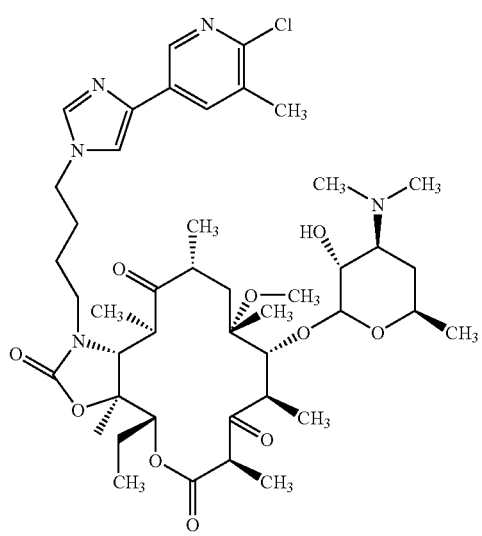

or a pharmaceutically acceptable salt, ester or prodrug thereof.

In another embodiment, the present invention provides compounds having the structure of the following formula (P):

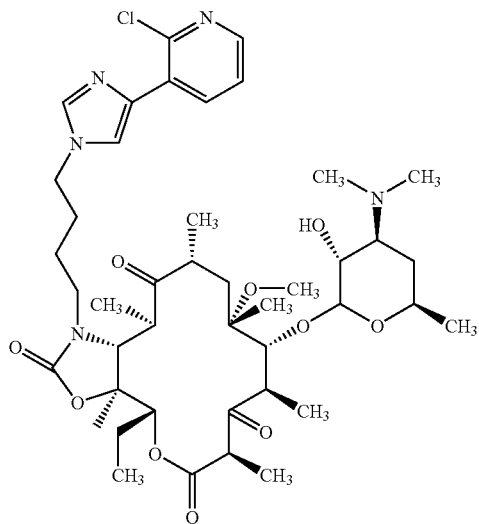

or a pharmaceutically acceptable salt, ester or prodrug thereof.

In another embodiment, the present invention provides compounds having the structure of the following formula (Q):

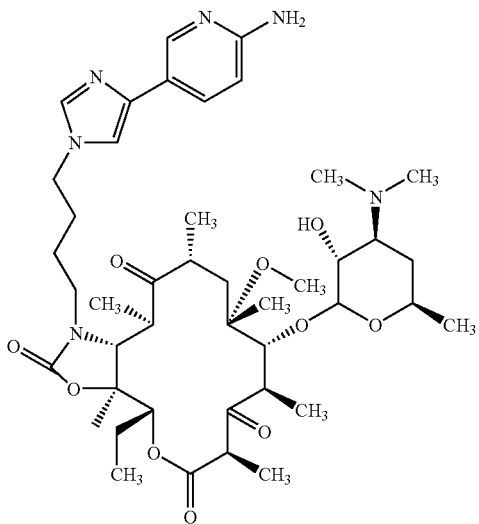

or a pharmaceutically acceptable salt, ester or prodrug thereof.

In some embodiments, the invention provides
q is 1, $R^{33}$ is hydrogen, $R^{34}$ is hydrogen, and $R^{32}$ is 6-methyl;
q is 1, $R^{33}$ is hydrogen, $R^{34}$ is hydrogen, and $R^{32}$ is 6-fluoro;
q is 1, $R^{33}$ is hydrogen, $R^{34}$ is hydrogen, and $R^{32}$ is 6-chloro;
q is 1, $R^{33}$ is hydrogen, $R^{34}$ is hydrogen, and $R^{32}$ is 6-methoxy;
q is 1, $R^{33}$ is hydrogen, $R^{34}$ is hydrogen, and $R^{32}$ is 6-ethoxy;
q is 1, $R^{33}$ is hydrogen, $R^{34}$ is hydrogen, and $R^{32}$ is 6-methoxy;
q is 1, $R^{33}$ is hydrogen, $R^{34}$ is hydrogen, and $R^{32}$ is 6-methylamino;
q is 1, $R^{33}$ is hydrogen, $R^{34}$ is hydrogen, and $R^{32}$ is 6-amino;
q is 1, $R^{33}$ is hydrogen, $R^{34}$ is hydrogen, and $R^{32}$ is 4-methoxy;
q is 1, $R^{33}$ is hydrogen, $R^{34}$ is hydrogen, and $R^{32}$ is 2-chloro;
q is 1, $R^{33}$ is hydrogen, $R^{34}$ is hydrogen, and $R^{32}$ is 2-methoxy;
q is 2, $R^{33}$ is hydrogen, $R^{34}$ is hydrogen, one of $R^{32}$ is 5-methyl and the other of $R^{32}$ is 6-chloro;
q is 1, $R^{33}$ is methyl, $R^{34}$ is hydrogen, and $R^{32}$ is 6-methoxy;
q is 1, $R^{33}$ is methyl, $R^{34}$ is hydrogen, and $R^{32}$ is 6-chloro;
q is 1, $R^{33}$ is hydrogen, $R^{34}$ is methyl, and $R^{32}$ is 6-methoxy; and
q is 1, $R^{33}$ is hydrogen, $R^{34}$ is methyl, and $R^{32}$ is 6-chloro.

In another embodiment, the invention provides of making a compound of formula A, comprising reacting a compound having the following structure:

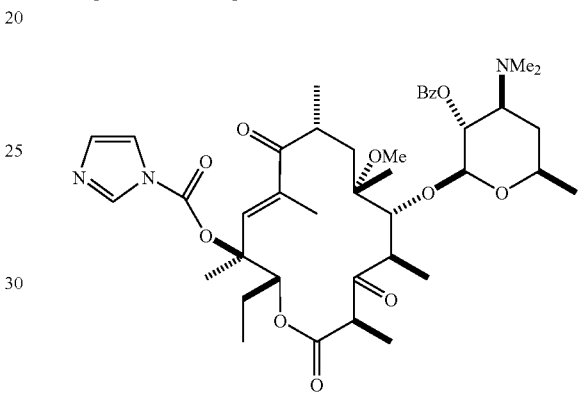

with an amine selected from the group consisting of 4-[4-(6-methyl-pyridin-3-yl)-imidazol-1-yl]-butylamine, 4-[4-(6-fluoro-pyridin-3-yl)-imidazol-1-yl]-butylamine, 4-[4-(6-methoxy-pyridin-3-yl)-imidazol-1-yl]-butylamine, 4-[4-(6-chloro-pyridin-3-yl)-imidazol-1-yl]-butylamine, 4-[4-(6-ethoxy-pyridin-3-yl)-imidazol-1-yl]-butylamine, {5-[1-(4-aminobutyl)imidazol-4-yl](2-pyridyl)}methylamine, {5-[1-(4-aminobutyl)imidazol-4-yl](2-pyridyl)}dimethylamine, 4-[4-(6-methoxy(3-pyridyl))-5-methylimidazolyl]butylamine, 4-[4-(6-methoxy(3-pyridyl))-2-methylimidazolyl]butylamine, 4-[4-(6-chloro-(3-pyridyl))-2-methylimidazolyl]butylamine, 4-[4-(4-chloro-3-pyridyl)imidazolyl]butylamine, 4-[4-(4-methoxy-3-pyridyl)imidazolyl]butylamine, 4-[4-(6-chloro (3-pyridyl))-5-methylimidazolyl]butylamine, 4-[4-(6-chloro-5-methyl-3-pyridyl)imidazolyl]butylamine, 4-[4-(2-chloro-3-pyridyl)imidazolyl]butylamine, and 5-[1-(4-amino-butyl)-1H-imidazol-4-yl]-pyridin-2-ylamine under conditions sufficient to form a cyclized carbamate compound; and removing the benzoyl group.

In yet another embodiment, the invention provides for a pharmaceutical composition comprising the compounds presented herein, pharmaceutically acceptable salts, esters, or prodrugs thereof, and a pharmaceutically acceptable carrier.

In yet another embodiment, the invention provides for a method of treating bacterial infection in a patient in need thereof comprising administering to said patient a therapeutically effecting amount of a pharmaceutical composition comprising a therapeutically effective amount of a compound presented herein, or a pharmaceutically acceptable salt, ester, or prodrug thereof, and a pharmaceutically acceptable carrier. In one embodiment, the patient is a mammal. In another embodiment the patient is a human.

In still another embodiment, the invention also provides for the use of the compounds presented herein in the manufacture of a medicament for the treatment or prophylaxis of bacterial infections.

As used throughout this specification and the appended claims, the following terms have the meanings specified.

The term "alkyl" refers to saturated, straight- or branched-chain hydrocarbon groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Alkyl also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

The terms "C$_1$–C$_3$-alkyl", "C$_1$–C$_6$-alkyl", and "C$_1$–C$_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of C$_1$–C$_3$-alkyl radicals include methyl, ethyl, propyl, and isopropyl, examples of C$_1$–C$_6$-alkyl radicals include, but are not limited to, methyl, ethyl, propyl, isopropyl, n-butyl, tert-butyl, neopentyl and n-hexyl. Examples of C$_1$–C$_{12}$-alkyl radicals include, but are not limited to, all the foregoing examples as well as n-heptyl, n-octyl, n-nonyl, n-decyl, n-undecyl and n-docecyl.

The term "C$_1$–C$_6$-alkoxy" as used herein refers to a C$_1$–C$_6$-alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy, and n-hexoxy.

The term "C$_2$–C$_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl, 1-methyl-2-buten-1-yl, and the like.

The term "C$_2$–C$_{12}$-alkynyl" as used herein refers to a monovalent group derived from a hydrocarbon moiety containing from two to twelve carbon atoms and having at least one carbon-carbon triple bond by the removal of a single hydrogen atom. Representative alkynyl groups include ethynyl, propynyl and the like.

The term 14-member macrolide antibiotics used herein include the natural products erythromycin, narbomycin, lakamycin, and oleandomycin, as well as derivatives such as roxithromycin, clarithromycin, dirithromycin, flurithromycin, and the ketolides (telithromycin, HMR 3004, TE-802, TE-810, ABT 773).

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "C$_1$–C$_3$-alkylamino" as used herein refers to one or two C$_1$–C$_3$-alkyl groups, as previously defined, attached to the parent molecular moiety through a nitrogen atom. Examples of C$_1$–C$_3$-alkylamino include, but are not limited to methylamino, dimethylamino, ethylamino, diethylamino, and propylamino.

The term "oxo" denotes a group wherein two hydrogen atoms on a single carbon atom in an alkyl group as defined above are replaced with a single oxygen atom (i.e. a carbonyl group).

The term "aryl" as used herein refers to a mono- or bicyclic carbocyclic ring system having one or two aromatic rings including, but not limited to, phenyl, naphthyl, tetrahydronaphthyl, indanyl, indenyl and the like. Representative aryl groups comprise from 3 to 12 carbon atoms. Preferable aryl groups include, but are not limited to, aryl groups of C$_3$–C$_{12}$, such as C$_4$–C$_{10}$ and C$_6$–C$_8$. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "$C_3$–$C_{12}$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl.

The terms "halo" and "halogen" as used herein refer to an atom selected from fluorine, chlorine, bromine and iodine.

The term "alkylamino" refers to a group having the structure —NHR' wherein R' is alkyl, as previously defined. Examples of alkylamino include, but are not limited to, methylamino, ethylamino, iso-propylamino.

The term "dialkylamino" refers to a group having the structure —NR'R" wherein R' and R" are independently selected from alkyl, as previously defined. Additionally, R' and R" taken together may optionally be —$(CH_2)_k$— where k is an integer of from 2 to 6. Examples of dialkylamino include, but are not limited to, dimethylamino, diethylamino, diethylaminocarbonyl, methylethylamino, methylpropylamino, and piperidino.

The term "haloalkyl" denotes an alkyl group, as defined above, having one, two, or three halogen atoms attached thereto and is exemplified by such groups as chloromethyl, bromoethyl, trifluoromethyl and the like.

The term "alkoxycarbonyl" represents an ester group; i.e. an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —$CO_2H$.

The term "carboxamide" as used herein refers to a group of formula —CONHR'R" wherein R' and R" are independently selected from hydrogen or alkyl, or R' and R" taken together may optionally be —$(CH_2)_k$—, wherein k is an integer of from 2 to 6.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl. Representative heteroaryl groups comprise from 3 to 12 carbon atoms. Preferable heteroaryl groups include, but are not limited to, aryl groups of $C_3$–$C_{12}$, such as $C_4$–$C_{10}$ and $C_6$–$C_8$. Representative examples of heteroaryl moieties include, but not limited to, pyridin-3-yl-1H-imidazol-1-yl, phenyl-1H-imidazol-1-yl, 3H-imidazo[4,5-b]pyridin-3-yl, quinolin-4-yl, 4-pyridin-3-yl-1H-imidazol-1-yl, quinolin-4-yl, quinolin-2-yl, 2-methyl-4-pyridin-3-yl-1H-imidazol-1-yl, 5-methyl-4-pyridin-3-yl-1H-imidazol-1-yl, 1H-imidazo[4,5-b]pyridin-1-yl, pyridin-3-ylmethyl, 3H-imidazo[4,5-b]pyridin-3-yl, 4-pyrimidin-5-yl-1H-imidazol-1-yl, 4-pyrazin-2-yl-1H-imidazol-1-yl, 4-pyridin-3-yl-1H-imidazol-1-yl, 4-pyridin-4-yl-1H-imidazol-1-yl, 4-(6-methylpyridin-3-yl)-1H-imidazol-1-yl, 4-(6-fluoropyridin-3-yl)-1H-imidazol-1-yl, 5-(3-aminophenyl)-1,3-thiazol-2-yl, 3-pyridin-3-ylphenoxy, 4-pyridin-3-ylphenoxy, 3H-imidazo[4,5-b]pyridin-3-yl, 4-phenyl-1H-imidazol-1-yl, 1H-pyrrolo[3,2-b]pyridin-1-yl, quinolin-3-yl, 2-methylquinolin-4-yl, trifluoromethyl)quinolin-4-yl, 8-(trifluoromethyl)-quinolin-4-yl, 2-phenoxyethoxy, 4-pyridin-3-ylphenoxy, 3-pyridin-3-ylphenoxy, 5-phenyl-1,3-thiazole, 5-(2,4-difluorophenyl)-1,3-thiazol-2-yl, 5-(3-aminophenyl)-1,3-thiazol-2-yl, (3,3'-bipyridin-5-ylmethyl)(methyl)amino, (6-methylpyridin-3-yl)-1H-imidazol-1-yl, methyl(quinolin-3-ylmethyl)amino, 3-phenylisoxazol-5-yl, 3-(4-methylphenyl)isoxazol-5-yl and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, Protective Groups in Organic Synthesis, 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reaction during synthetic procedures and to be selectively removable. The use of ketone-protecting groups is well known in the art for protecting groups against undesirable reaction during a synthetic procedure and many such protecting groups are known, cf., for example, T. H. Greene and P. G. M. Wuts, Protective Groups in Organic Synthesis, 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

The term "protected-hydroxy" refers to a hydroxy group protected with a hydroxy protecting group, as defined above, including benzoyl (Bz), acetyl (Ac), trimethylsilyl (TMS), triethylsilyl (TES), methoxymethyl groups, for example.

The term "substituted aryl" as used herein refers to an aryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 microns. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1–5 microns. Predominantly in this application means that at least 70% but preferably more than 90% of all generated aerosol particles are within 1–5 micron range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream nebulizers (Medic-Aid Ltd., West Sussex, England), Pari LC and Pari LC Star jet nebulizers (Pari Respiratory Equipment, Inc., Richmond, Va.), and Aerosonic (DeVilbiss Medizinische Produkte (Deutschland) GmbH, Heiden, Germany) and UltraAire (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

The foregoing may be better understood by reference to the following examples which are presented for illustration and not to limit the scope of the inventive concepts.

DESCRIPTION OF THE PREFERRED EMBODIMENTS

The following examples are provided for illustrative purposes and are not to be construed to limit the scope of the claims in any manner whatsoever.

EXAMPLE 1

Methyl Imidazolyl Carbamate Ketolide Enone

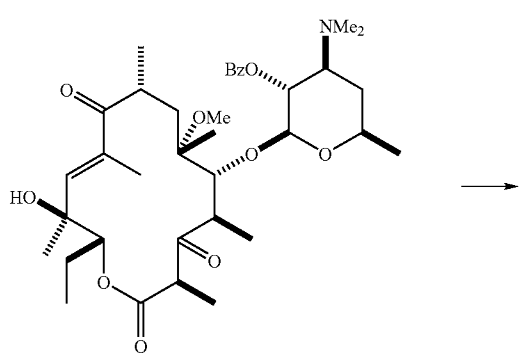

-continued

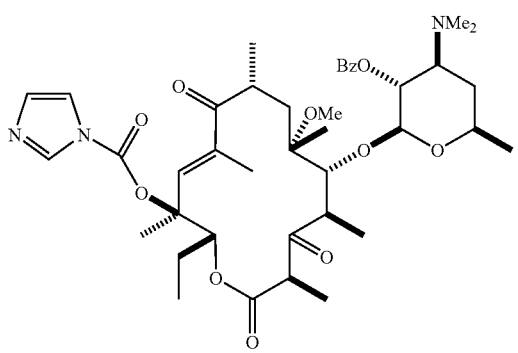

A 0.2M solution of a methyl ketolide enone-$C_{12}$-ol (Registry Number: 190839-65-7, 1.00 eq) and 1,1-carbonyldiimidazole (2.00 eq) in tetrahydrofuran is cooled to −15° C. Sodium hydride (60% dispersion in mineral oil, 105 mg, 2.63 mmol, 1.2 eq) is added. The mixture is stirred at −15° C. for 15 min and at ambient temperature for an additional 45 min. The reaction is diluted with ethyl acetate (100 ml) and quenched with saturated aqueous sodium bicarbonate (20 ml). The layers are separated. The organic layer is washed with water (2×20 ml) and brine (20 ml), dried over sodium sulfate, filtered, and concentrated. This procedure yields crude methyl imidazolyl carbamate (Bz=benzoyl, PhC(=O)—).

EXAMPLE 2

Pyridyl-Substituted Amines

EXAMPLE 2(A)

Synthesis of 4-IODO-1-IRITYL-1H-IMIDAZOLE

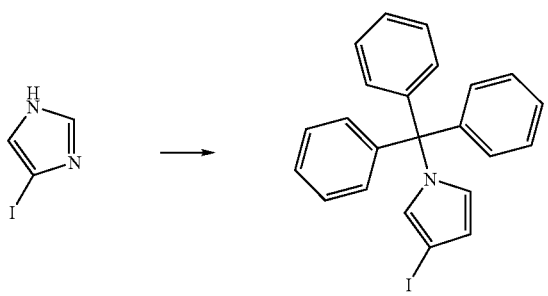

To a solution of 4-iodoimidazole (50 g, 258 mmoles) in DMF (500 ml) was added triethyl amine (37.7 ml, 270.6 mmoles) and than triphenylmethyl chloride (69.7 g, 250 mmoles). After stirring at room temperature for 48 hours, the solution was poured into ice water (2.5 L). The solid was filtered and pumped on for several hours to yield the crude compound. Ethyl ether (200 ml) was added to the crude compound and the solution was filtered to yield 4-iodo-1-trityl-1H-imidazole (104.1, 93%) as a white solid. MH⁺ (437).

EXAMPLE 2(B)

4-[4-(6-METHYL-3-PYRIDYL)IMIDAZOLYL]BUTYLAMINE

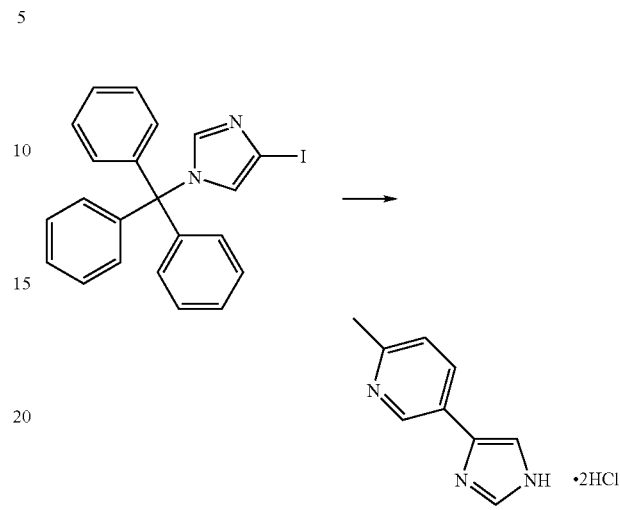

A. 5-(1H-imidazol-4-yl)-2-methyl-pyridine. To a solution of 4-iodo-1-trityl-1H-imidazole (15.0 g, 34 mmoles) in THF (150 ml) at room temperature was added ethylmagnesium bromide (41 ml, 40.7 mmoles) under dry conditions. After stirring for 90 minutes, zinc chloride (5.6 g, 40.7 mmoles) was added to the reaction mixture. After stirring for another 90 minutes, tetrakis(triphenylphosphine)palladium (4.0 g, 3.43 mmoles) and 5-bromo-2-methylpyridine (7.0 g, 40.7 mmoles) were added to the reaction mixture. Following that, the reaction mixture was heated in a 70° C. oil bath overnight. Upon cooling, the reaction was diluted with dichloromethane and washed with an EDTA buffer (at approimate pH 9) (2×300 ml), NaCl (sat.) (300 ml), dried over sodium sulfate, filtered, and concentrated. The crude product was dissolved in ethanol (250 ml) and concentrated HCl (13.6 ml) was added to the solution at room temperature. The reaction mixture was heated in a 50° C. oil bath for 2 hours. Upon cooling, the reaction was filtered and washed with ethyl ether (25 ml) to yield 5-(1H-imidazol-4-yl)-2-methyl-pyridine (5.815 g, 63%). MH⁺(160).

2-[4-(6-Methyl-pyridin-3-yl)-imidazol-1-ylmethyl]-isoindole-1,3-dione

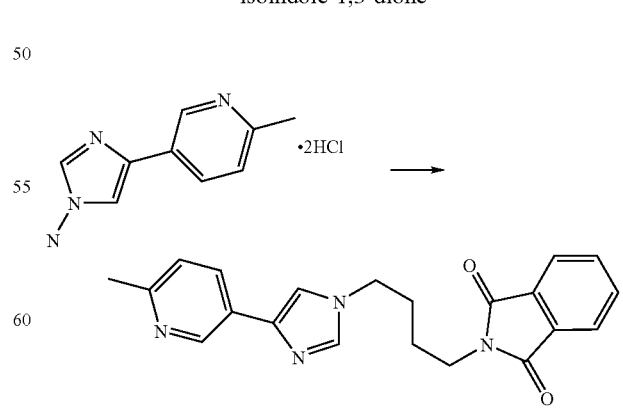

B. 2-[4-(6-Methyl-pyridin-3-yl)-imidazol-1-ylmethyl]-isoindole-1,3-dione. To a solution of 5-(1H-Imidazol-4-yl)-

2-methyl-pyridine (2.185 g, 9.46 mmoles) in DMF (20 ml) was added potassium carbonate (6.54 g, 47.3 mmoles) at room temperature under dry conditions. After heating the reaction mixture in an 80° C. oil bath for 1 hour, N-(4-bromobutyl)phthalimide (10.63 g, 37.8 mmoles) was added to the mixture. The solution was left stirring in an 80° C. oil bath for 24 hours. Upon cooling, the reaction was filtered and the solid was washed with ethyl acetate (25 ml). The filtrate was diluted with ethyl acetate and washed with NH$_4$Cl (sat.) (50 ml), H$_2$O (50 ml), NaCl (sat.) (75 ml), dried over sodium sulfate, filtered, and concentrated. The crude product was purified by flash 40 chromatography using an initial solvent gradient of 99% DCM, 1% MeOH, and 0.1% TEA (1 L), then a solvent gradient of 97% DCM, 3% MeOH, and 0.1% TEA (1 L) to yield 2-[4-(6-Methyl-pyridin-3-yl)-imidazol-1-ylmethyl]-isoindole-1,3-dione (1.275 g, 37%). MH$^+$(361).

4-[4-(6-methyl-3-pyridyl)imidazolyl]butylamine

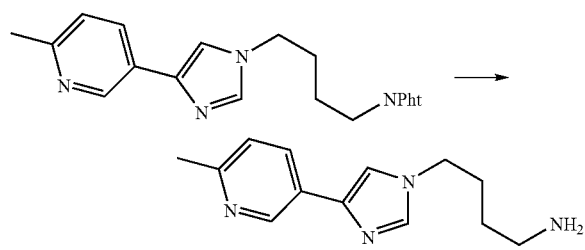

C. 4-[4-(6-methyl-3-pyridyl)imidazolyl]butylamine. To a solution of 2-[4-(6-methyl-pyridin-3-yl)-imidazol-1-ylmethyl]-isoindole-1,3-dione (1.5 g, 4.17 mmoles) in ethanol (42 ml) was added hydrazine (0.26 ml, 8.33 mmoles). After heating the reaction mixture in a 65° C. oil bath for 15 hours, the solution was cooled, filtered, and concentrated. The resulting oil was taken up in dichloromethane (150 ml) and was washed with 1M NaOH (15 ml). The aqueous layer was extracted further with dichloromethane (2×150 ml), the combined organics were dried over MgSO$_4$, filtered and concentrated yielding 4-[4-(6-methyl-3-pyridyl)imidazolyl] butylamine (917 mg, 95%). MH$^+$(231).

EXAMPLE 2(C)

4-[4-(6-FLUORO-3-PYRIDYL)IMIDAZOLYL]
BUTYLAMINE

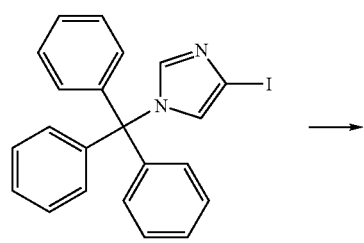

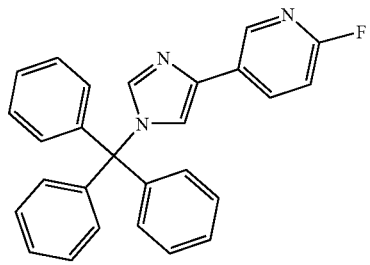

A. 2-fluoro-5-(1-trityl-1H-imidazol-4-yl)-pyridine. To a solution of 4-iodo-1-trityl-1H-imidazole (10.0 g, 23 mmoles) in THF (100 ml) at room temperature was added ethylmagnesium bromide (28 ml, 27.5 mmoles) under dry conditions. After stirring for 90 minutes, zinc chloride (3.8 g, 27.5 mmoles) was added to the reaction mixture. After stirring for another 90 minutes, tetrakis(triphenylphosphine) palladium (2.6 g, 2.3 mmoles) and 5-bromo-2-fluoropyridine (5.0 g, 27.5 mmoles) were added to the reaction mixture. Following that, the reaction mixture was heated in a 70° C. oil bath overnight. Upon cooling, the reaction was diluted with dichloromethane and washed with an EDTA buffer (at approximate pH 9) (2×300 ml), NaCl (sat.) (300 ml), dried over sodium sulfate, filtered, and concentrated. The crude product was purified by flash 40 chromatography using an initial solvent gradient of 99.5% DCM, 0.5% MeOH, and 0.1% TEA (1 L), then a solvent gradient of 99% DCM, 1% MeOH, and 0.1% TEA (1 L) to yield 2-fluoro-5-(1-trityl-1H-imidazol-4-yl)-pyridine (6.4 g, 69%). MH$^+$ (406).

2-fluoro-5-(1H-imidazol-4-yl)-pyridine

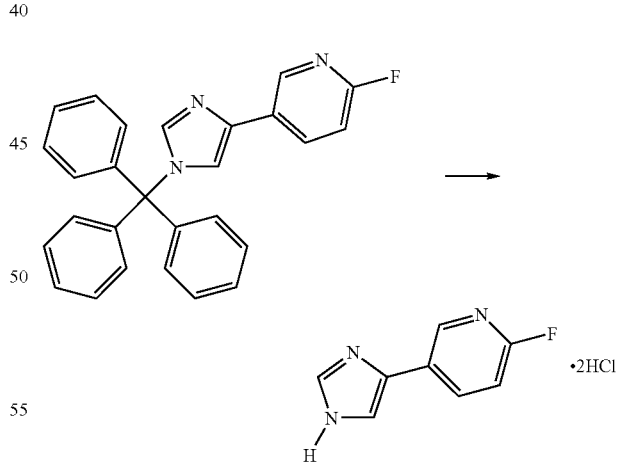

B. 2-fluoro-5-(1H-imidazol-4-yl)-pyridine. To a solution of 2-fluoro-5-(1-trityl-1H-imidazol-4-yl)-pyridine (6.4 g, 15.8 mmoles) in ethanol (100 ml) was added concentrated HCl (7 ml) at room temperature. The reaction mixture was heated in a 50° C. oil bath for 90 minutes. Upon cooling, the reaction was concentrated in vacuo to about half the original amount of solvent. Ethyl ether (75 ml) was added to the mixture and the product precipitated slowly. After 90 minutes, the resulting solid 2-fluoro-5-(1H-imidazol-4-yl)-pyridine (1.72 g, 46%) was collected by filtration. MH+(164).

2-{4-[4-(6-fluoro-pyridin-3-yl)-imidazol-1-ylm-ethyl]-butyl}-isoindole-1,3-dione

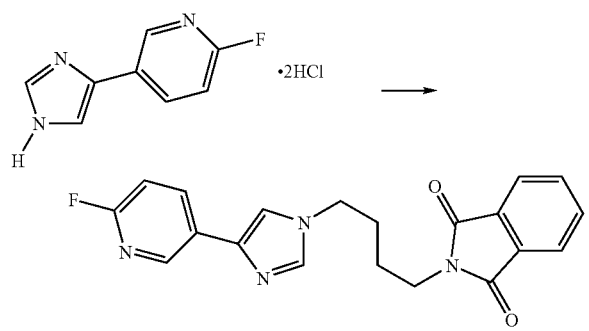

C. 2-{4-[4-(6-fluoro-pyridin-3-yl)-imidazol-1-ylmethyl]-butyl}-isoindole-1,3-dione. To a solution of 2-fluoro-5-(1H-imidazol-4-yl)-pyridine (1.72 g, 7.3 mmoles) in DMF (15 ml) was added potassium carbonate (5.0 g, 36.4 mmoles) at room temperature under dry conditions. After heating the reaction mixture in a 80° C. oil bath for 1 hour, N-(4-bromobutyl)phthalimide (8.2 g, 29.2 mmoles) was added to the mixture. The solution was left stirring in an 80° C. oil bath for 24 hours. Upon cooling, the reaction was filtered and the solid was washed with ethyl acetate (25 ml). The filterate was diluted with ethyl acetate and washed with NH4Cl (sat.) (50 ml), H2O (50 ml), NaCl (sat.) (75 ml), dried over sodium sulfate, filtered, and concentrated. The crude product was purified by flash 40 chromatography using an initial solvent gradient of 99% DCM, 1% MeOH, and 0.1% TEA (1 L), then a solvent gradient of 97% DCM, 3% MeOH, and 0.1% TEA (1 L) to yield 2-{4-[4-(6-fluoro-pyridin-3-yl)-imidazol-1-ylmethyl]-butyl}-isoindole-1,3-dione (1.476 g, 55%). MH+(365).

4-[4-(6-fluoro-3-pyridyl)imidazolyl]butylamine

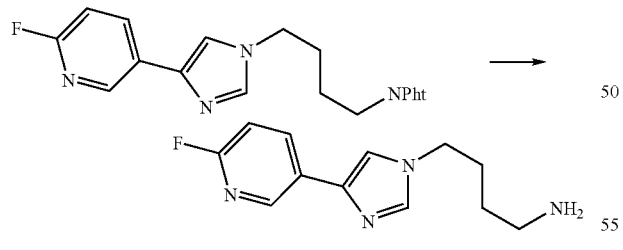

D. 4-[4-(6-fluoro-3-pyridyl)imidazolyl]butylamine. To a solution of 2-[4-(6-fluoro-pyridin-3-yl)-imidazol-1-ylm-ethyl]-isoindole-1,3-dione (1.12 g, 3.07 mmoles) in ethanol (31 ml) was added hydrazine (0.2 ml, 6.14 mmoles). After heating the reaction mixture in a 65° C. oil bath for 15 hours, the solution was cooled, filtered and concentrated. The resulting oil was taken up in dichloromethane (150 ml) and was washed with 1M NaOH (15 ml). The aqueous layer was extracted further with dichloromethane (2×150 ml), the combined organics were dried over MgSO4, filtered and concentrated yielding 4-[4-(6-fluoro-3-pyridyl)imidazolyl]butylamine (717 mg, 99%). MH+(235).

EXAMPLE 2(D)

4-[4-(6-METHOXY-3-PYRIDYL)IMIDAZOLYL]BUTYLAMINE

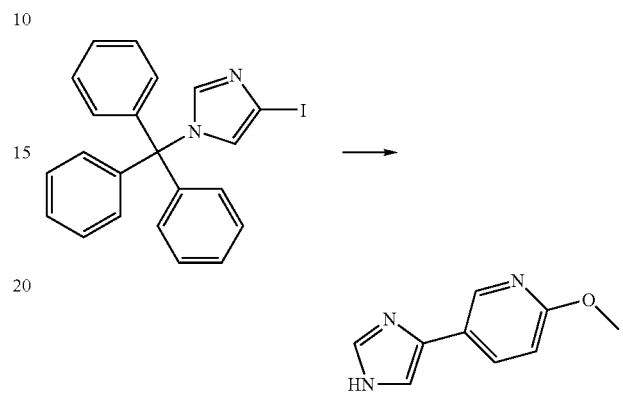

A. 5-imidazol-4-yl-2-methoxypyridine. To a solution of 4-iodo-1-trityl-1H-imidazole (25 g, 57.2 mmoles) in THF (150 ml) at room temperature was added ethylmagnesium bromide (69 ml, 68.7 mmoles) under dry conditions. After stirring for 90 minutes, zinc chloride (9.4 g, 68.6 mmoles) was added to the reaction mixture. After stirring for another 90 minutes, tetrakis(triphenylphosphine)palladium (6.6 g, 5.72 mmoles) and 5-bromo-2-methoxypyridine (8.9 ml, 68.7 mmoles) were added to the reaction mixture. Following that, the reaction mixture was heated in a 70° C. oil bath overnight. Upon cooling, the reaction was diluted with dichloromethane (500 ml) and washed with a 30% NaOH solution containing an added 20 g of EDTA (3×200 ml), with NaCl (sat.) (200 ml), dried over MgSO4, filtered, and concentrated. To the crude material was added dichloromethane (200 ml) and trifluoroactetic acid (40 ml, 410 mmoles). After standing for 6 hours, the reaction was concentrated and pumped on overnight. The crude material was purified by flash chromatography using 0–5% MeOH/CH2Cl2 with 0.1% triethylamine yielding 5-imidazol-4-yl-2-methoxypyridine (7.0 g, 70%). MH+(176).

2-{4-[4-(6-methoxy-pyridin-3-yl)-imidazol-1-yl]-butyl}-isoindole-1,3-dione

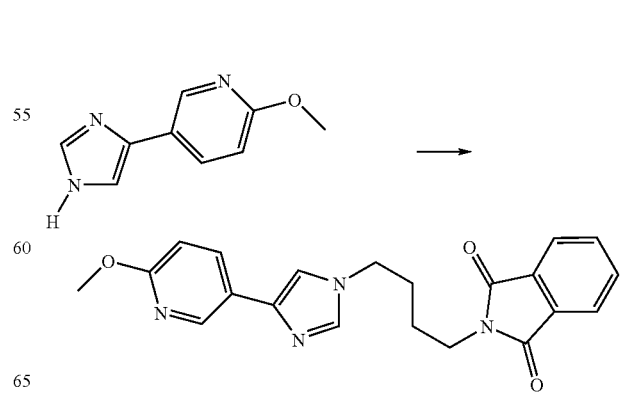

B. 2-{4-[4-(6-methoxy-pyridin-3-yl)-imidazol-1-yl]-butyl}-isoindole-1,3-dione. To a solution of 5-(1H-imidazol-4-yl)-2-methoxy-pyridine (6.7 g, 38.3 mmoles) in DMF (80 ml) was added potassium carbonate (26.5 g, 192 mmoles) and N-(4-bromobutyl)phthalimide (43.0 g, 153 mmoles) at room temperature under dry conditions. The solution was left stirring at room temperature for 36 hours. The reaction was filtered and the solid was washed with ethyl acetate (25 ml). The filtrate was diluted with ethyl acetate and washed with NH₄Cl (sat.) (50 ml), H₂O (50 ml), NaCl (sat.) (75 ml), dried over sodium sulfate, filtered, and concentrated. The crude product was purified by flash 40 chromatography using an initial solvent gradient of 99% DCM, 1% MeOH, and 0.1% TEA (1 L), then a solvent gradient of 97% DCM, 3% MeOH, and 0.1% TEA (1 L) to yield 2-{4-[4-(6-methoxy-pyridin-3-yl)-imidazol-1-yl]-butyl}-isoindole-1,3-dione (10.09 g, 70%). MH+(377).

4-[4-(6-methoxy-3-pyridyl)imidazolyl]butylamine

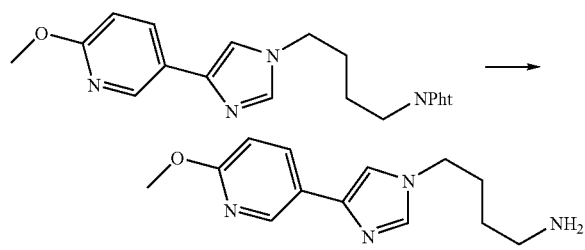

C. 4-[4-(6-methoxy-3-pyridyl)imidazolyl]butylamine. To a solution of 2-[4-(6-methoxy-pyridin-3-yl)-imidazol-1-ylmethyl]-isoindole-1,3-dione (10 g, 26.6 mmoles) in ethanol (265 ml) was added hydrazine (1.67 ml, 53.2 mmoles). After heating the reaction mixture in a 60° C. oil bath for 15 hours, the solution was cooled, filtered and concentrated. The resulting oil was taken up in dichloromethane (400 ml) and was washed with 1M NaOH (50 ml). The aqueous layer was extracted further with dichloromethane (2×400 ml), the combined organics were dried over MgSO₄, filtered and concentrated yielding 4-[4-(6-methoxy-3-pyridyl)imidazolyl]butylamine (6.46 g, 98%). MH⁺(247).

EXAMPLE 2(E)

4-[4-(6-CHLORO-3-PYRIDYL)IMIDAZOLYL]BUTYLAMINE

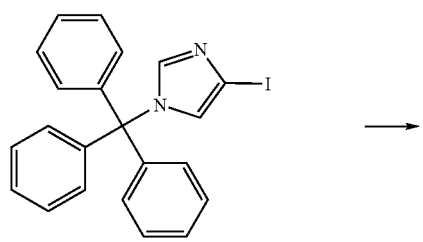

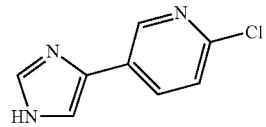

A. 5-(1H-imidazol-4-yl)-2-chloro-pyridine. To a solution of 4-iodo-1-trityl-1H-imidazole (72.8 g, 166 mmoles) in THF (400 ml) at room temperature was added ethylmagnesium bromide (200 ml, 200 mmoles) under dry conditions. After stirring for 90 minutes, zinc chloride (27.2 g, 200 mmoles) was added to the reaction mixture. After stirring for another 90 minutes, tetrakis(triphenylphosphine)palladium (20 g, 16.6 mmoles) and 5-bromo-2-chloropyridine (38.48 g, 200 mmoles) were added to the reaction mixture. Following that, the reaction mixture was heated in a 70° C. oil bath overnight. Upon cooling, the reaction was diluted with dichloromethane (1 L) and washed with a 30% NaOH solution containing an added 40 g of EDTA (3×400 ml), with NaCl (sat.) (300 ml), dried over MgSO₄, filtered, and concentrated. To the crude material was added dichloromethane (600 ml) and trifluoroactetic acid (180 ml). After standing for 1 hour, the reaction was concentrated and pumped on overnight. To the resulting oily tar was added 1M HCl (100 ml) and the mixture was sonicated for 30 minutes and than filtered. The aqueous filtrate was washed with diethyl ether (400 ml). The ether layer was back extracted with 1M HCl (2×20 ml). The combined aqueous layers were washed with diethyl ether (2×200 ml). The aqueous layer was cooled in an ice bath and the pH was adjusted by addition of a 30% NaOH solution until the pH was around 9–10. The resulting solid was filtered, rinsed with cold water (20 ml), rinsed with diethyl ether (20 ml), and pumped on yielding 5-(1H-imidazol-4-yl)-2-chloro-pyridine (12.90 g, 43%). MH⁺(180).

2-{4-[4-(6-chloro-pyridin-3-yl)-imidazol-1-yl]-butyl}-isoindole-1,3-dione

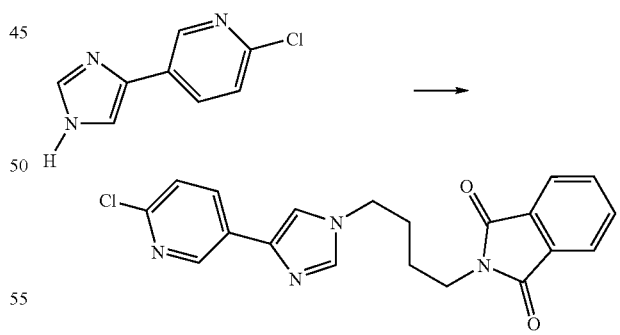

B. 2-{4-[4-(6-chloro-pyridin-3-yl)-imidazol-1-yl]-butyl}-isoindole-1,3-dione. To a solution of 5-(1H-imidazol-4-yl)-2-chloro-pyridine (15.14 g, 84.1 mmoles) in DMF (336 ml) was added potassium carbonate (58.1 g, 420.6 mmoles) and N-(4-bromobutyl)phthalimide (59.3 g, 210.3 mmoles) at room temperature under dry conditions. The solution was left stirring at room temperature for 48 hours. The reaction was filtered and the resulting clear solution was dumped onto ice (1.5 L). The precipitate was filtered and rinsed with water (2×500 ml) and was pumped on for 1 hour. The material was than rinsed with diethyl ether (15×500 ml) and than was pumped on to yield 2-{4-[4-(6-chloro-pyridin-3-yl)-imidazol-1-yl]-butyl}-isoindole-1,3-dione (25.16 g, 78%). MH$^+$(381).

4-[4-(6-chloro-3-pyridyl)imidazolyl]butylamine

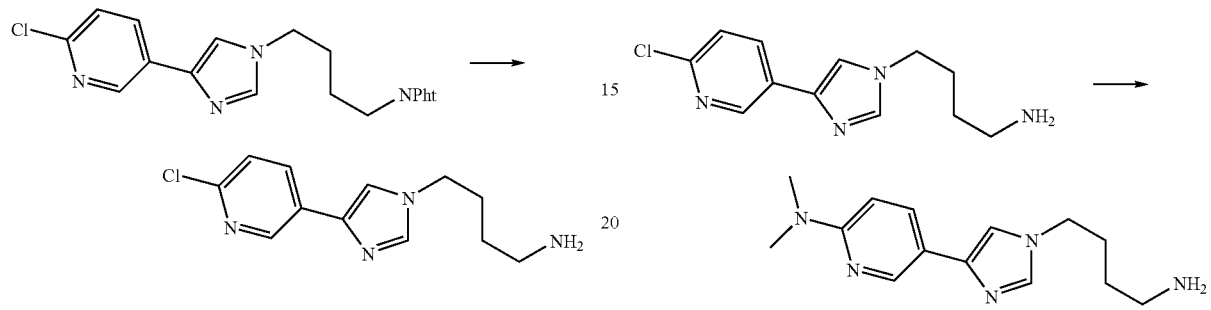

C. 4-[4-(6-chloro-3-pyridyl)imidazolyl]butylamine. To a solution of 2-[4-[4-(6-chloro-pyridin-3-yl)-imidazol-1-ylmethyl]-isoindole-1,3-dione (13.9 g, 36.6 mmoles) in ethanol (365 ml) was added hydrazine (2.3 ml, 73.16 mmoles). After heating the reaction mixture in a 65° C. oil bath for 15 hours, the solution was cooled, filtered, and concentrated. The resulting oil was taken up in dichloromethane (600 ml) and was washed with 1M NaOH (100 ml). The aqueous layer was extracted further with dichloromethane (3×400 ml), the combined organics were dried over MgSO$_4$, filtered, and concentrated yielding 4-[4-(6-chloro-3-pyridyl)imidazolyl] butylamine (7.83 g, 85.6%). MH$^+$(251).

EXAMPLE 2(F)

4-[4-(6-ETHOXY-3-PYRIDYL)IMIDAZOLYL]BUTYLAMINE

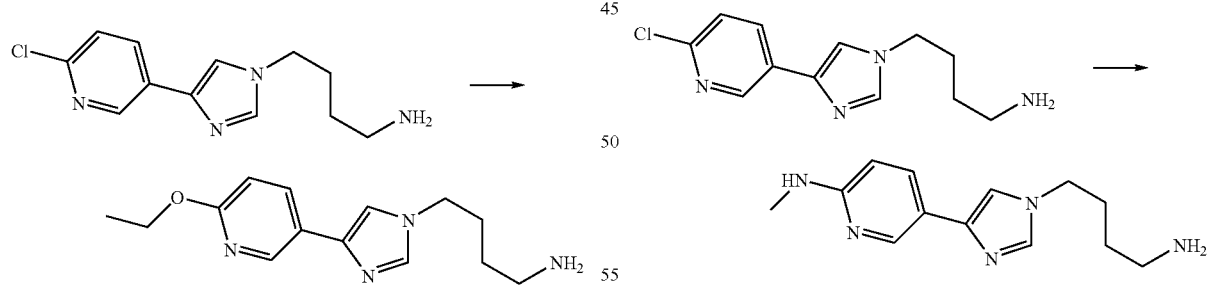

To a solution of 4-[4-(6-chloro-3-pyridyl)imidazolyl]butylamine (825 mg, 3.3 mmoles) in ethanol (15 ml) was added sodium ethoxide (2.24 g, 33 mmoles). The reaction mixture was heated in a sealed vessel in a 130° C. oil bath for 48 hours; upon cooling more sodium ethoxide was added (1.0 g) and the closed vessel was heated at 150° C. for 48 hours more. Upon cooling the reaction mixture was concentrated and than was taken up in dichloromethane (200 ml) and was washed with water (50 ml). The aqueous layer was extracted further with dichloromethane (2×200 ml), the combined organics were dried over MgSO$_4$, filtered, and concentrated yielding 4-[4-(6-ethoxy-3-pyridyl)imidazolyl]butylamine (747 mg, 87%). MH$^+$(261).

EXAMPLE 2(G)

{5-[1-(4-AMINOBUTYL)IMIDAZOL-4-YL](2-PYRIDYL)}DIMETHYLAMINE

To a solution of 4-[4-(6-chloro-3-pyridyl)imidazolyl]butylamine (1.0 g, 4.0 mmoles) was added dimethylamine, 5.6M in ethanol (15 ml, 84 mmoles). The reaction mixture was heated in a sealed vessel in a 150° C. oil bath for 73 hours. Upon cooling the reaction mixture was concentrated and then was taken up in dichloromethane (200 ml) and was washed with 1M NaOH (20 ml). The aqueous layer was extracted further with dichloromethane (2×200 ml), the combined organics were dried over MgSO$_4$, filtered, and concentrated yielding {5-[1-(4-aminobutyl)imidazol-4-yl](2-pyridyl)}dimethylamine (1.04 mg, 100%). MH$^+$(260).

EXAMPLE 2(H)

{5-[1-(4-AMINOBUTYL)IMIDAZOL-4-YL](2-PYRIDYL)}METHYLAMINE

To a solution of 4-[4-(6-chloro-3-pyridyl)imidazolyl]butylamine (1.0 g, 4.0 mmoles) was added methylamine, 8.0M in ethanol (15 ml, 120 mmoles). The reaction mixture was heated in a sealed vessel in a 150° C. oil bath for 73 hours. Upon cooling the reaction mixture was concentrated and then was taken up in dichloromethane (200 ml) and was washed with 1M NaOH (20 ml). The aqueous layer was extracted further with dichloromethane (2×200 ml), the combined organics were dried over MgSO$_4$, filtered, and concentrated yielding {5-[1-(4-aminobutyl)imidazol-4-yl](2-pyridyl)}methylamine (766 mg, 78%). MH$^+$(246).

EXAMPLE 2(I)

4-[4-(6-CHLORO-3-PYRIDYL)IMIDAZOLYL] BUTYLAMINE

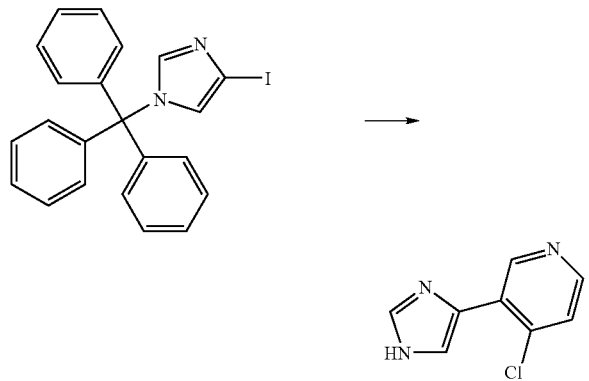

A. 4-chloro-3-(1H-imidazol-4-yl)-pyridine. To a solution of 4-iodo-1-trityl-1H-imidazole (13 g, 30.3 mmoles) in THF (150 ml) at room temperature was added ethylmagnesium bromide (43 ml, 33 mmoles) under dry conditions. After stirring for 90 minutes, zinc chloride (4.5 g, 33 mmoles) was added to the reaction mixture. After stirring for another 90 minutes, tetrakis(triphenylphosphine)palladium (3.5 g, 3 mmoles) and 5-bromo-2-chloropyridine (7.0 g, 36 mmoles) were added to the reaction mixture. Following that, the reaction mixture was heated in a 70° C. oil bath overnight. Upon cooling, the reaction was diluted with dichloromethane and washed with an EDTA buffer (at approximate pH 9) (300 ml), NaCl (sat.) (150 ml), dried over sodium sulfate, filtered, and concentrated. To the crude material in DCM (250 ml) at room temperature was added trifluoroacetic acid (60 ml, 780 mmoles). After stirring for 90 minutes, the excess TFA and DCM were removed in vacuo. The crude product was left under high vacuum pump overnight. To the crude product was added 60 ml of 3N HCl and the mixture was left in the sonicator for 120 minutes. Once recovered from the sonicator, the mixture was filtered and the aqueous solution was washed with diethyl ether until the organic phase was no more UV active. The aqueous solution was cooled to 0° C. and 30% NaOH solution was added until an approximate pH 7–8 was obtained. The obtained solid product was filtered and dried over night under high vacuum pump to yield 4-chloro-3-(1H-imidazol-4-yl)-pyridine (3.32 g, 61%). MH$^+$(180).

2-{4-[4-(4-chloro-3-pyridyl)imidazolyl]butyl}isoindole-1,3-dione

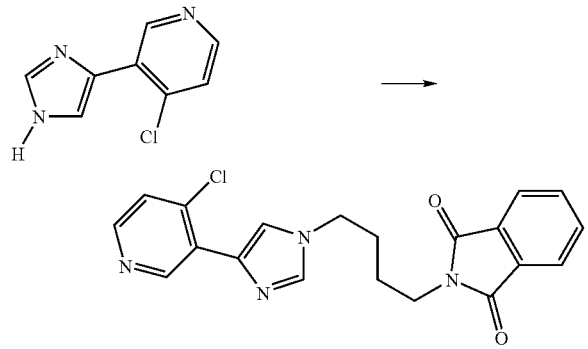

B. 2-{4-[4-(4-chloro-3-pyridyl)imidazolyl]butyl}isoindole-1,3-dione. To a solution of 4-(4-chloro-3-pyridyl)imidazole (3.32 g, 18.54 mmoles) in DMF (74 ml) was added potassium carbonate (12.8 g, 92.7 mmoles) and N-(4-bromobutyl) phthalimide (10.5 g, 37.1 mmoles) at room temperature under dry conditions. The solution was left stirring at room temperature for 96 hours. The reaction was filtered and the resulting clear solution was dumped onto ice (500 ml). The precipitate was filtered and the solid was dissolved in DCM. The organic solution was dried over sodium sulfate, filtered and concentrated. The crude product was purified by flash chromatography using a solvent gradient of 0–1–3% MeOH in CH2Cl$_2$ with 0.1% TEA to yield 2-{4-[4-(4-chloro-3-pyridyl)imidazolyl]butyl}isoindole-1,3-dione (2.82 g, 40%). MH$^+$(381).

4-[4-(4-chloro-3-pyridyl)imidazolyl]butylamine

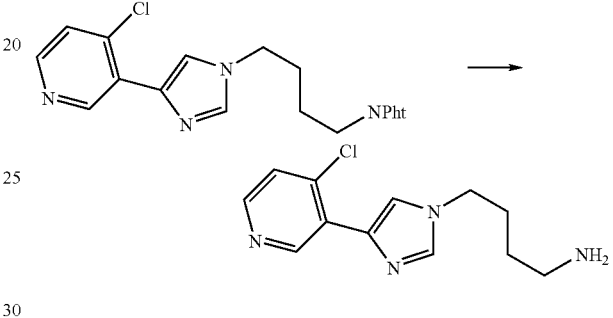

C. 4-[4-(6-chloro-3-pyridyl)imidazolyl]butylamine. To a solution of 2-[4-(4-chloro-pyridin-3-yl)-imidazol-1-ylmethyl]-isoindole-1,3-dione (2.82 g, 7.42 mmoles) in ethanol (75 ml) was added hydrazine (0.58 ml, 18.6 mmoles). After heating the reaction mixture in a 65° C. oil bath for 15 hours, the solution was cooled, filtered, and concentrated. The resulting oil was taken up in dichloromethane (200 ml) and was washed with 1M NaOH (250 ml). The aqueous layer was extracted further with dichloromethane (2×200 ml), the combined organics were dried over MgSO$_4$, filtered, and concentrated yielding 4-[4-(4-chloro-3-pyridyl)imidazolyl]butylamine (1.74 g, 94%). MH$^+$(251).

EXAMPLE 2(J)

4-[4-(4-METHOXY-3-PYRIDYL)IMIDAZOLYL] BUTYLAMINE

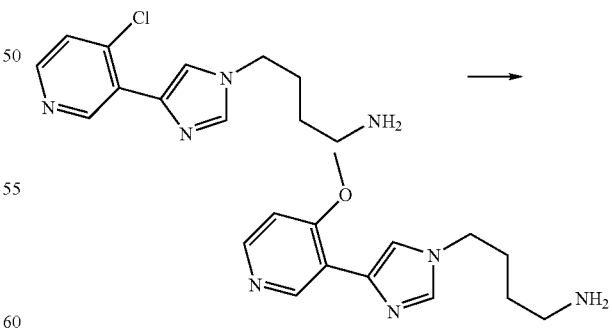

To a solution of 4-[4-(4-chloro-3-pyridyl)imidazolyl]butylamine (400 mg, mmoles) was added sodium methoxide, 5.3 M in methanol (10 ml, 53 mmoles). The reaction mixture was heated at 70° C. for 2 hours. Upon cooling the reaction mixture was concentrated to around 4 ml and then was taken up in dichloromethane (125 ml) and was washed with water (20 ml). The aqueous layer was extracted further with dichloromethane (125 ml), the combined organics were dried over MgSO$_4$, filtered, and concentrated yielding 4-[4-(4-methoxy-3-pyridyl)imidazolyl]butylamine (379 mg, 96%). MH$^+$(247).

EXAMPLE 2(K)

4-[4-(2-CHLORO-3-PYRIDYL)IMIDAZOLYL]BUTYLAMINE

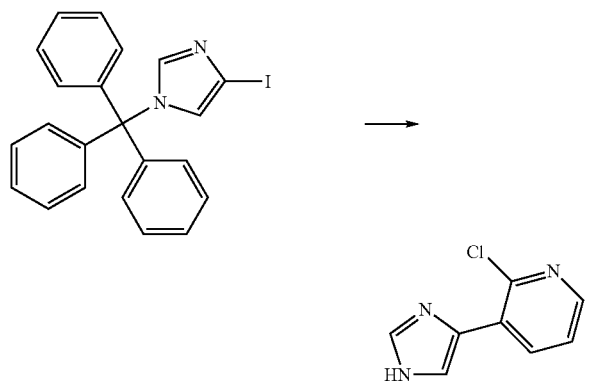

A. 4-(2-chloro-3-pyridyl)imidazole. To a solution of 4-iodo-1-trityl-1H-imidazole (25 g, 57.3 mmoles) in THF (285 ml) at room temperature was added ethylmagnesium bromide (69 ml, 68.8 mmoles) under dry conditions. After stirring for 90 minutes, zinc chloride (9.37 g, 68.8 mmoles) was added to the reaction mixture. After stirring for another 90 minutes, tetrakis(triphenylphosphine)palladium (5 g, 4.3 mmoles) and 3-bromo-2-chloropyridine (13.2 g, 68.8 mmoles) were added to the reaction mixture. Following that, the reaction mixture was heated in a 70° C. oil bath overnight. Upon cooling, the reaction was diluted with dichloromethane (1 L) and washed with a 30% NaOH solution containing an added 40 g of EDTA (3×400 ml), with NaCl (sat.) (300 ml), dried over MgSO$_4$, filtered, and concentrated. To the crude material was added dichloromethane (200 ml) and trifluoroactetic acid (60 ml). After standing for 1 hour, the reaction was concentrated and pumped on overnight. To the resulting oily tar was added 1M HCl (60 ml) and the mixture was sonicated for 30 minutes and than filtered. The aqueous filtrate was washed with diethyl ether (2×100 ml). The aqueous layer was cooled in an ice bath and the pH was adjusted by addition of a 30% NaOH solution until the pH was approximately 9–10. The resulting solid was filtered, rinsed with cold water (20 ml), rinsed with diethyl ether (20 ml), and pumped on yielding 4-(2-chloro-3-pyridyl)imidazole (8.43 g, 82%). MH$^+$(180).

2-{4-[4-(2-chloro-3-pyridyl)imidazolyl]butyl}isoindole-1,3-dione

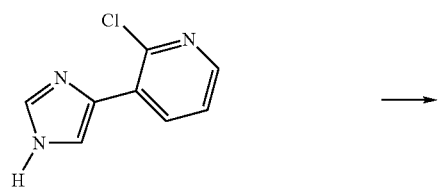

-continued

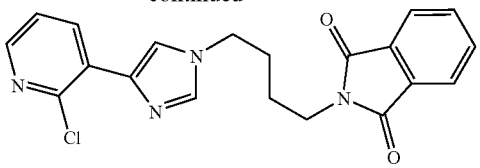

B. 2-{4-[4-(2-chloro-3-pyridyl)imidazolyl]butyl}isoindole-1,3-dione. To a solution of 4-(2-chloro-3-pyridyl)imidazole (8.43 g, 47.1 mmoles) in DMF (188 ml) was added potassium carbonate (32.6 g, 235.5 mmoles) and N-(4-bromobutyl)phthalimide (26.6 g, 94.2 mmoles) at room temperature under dry conditions. The solution was left stirring at room temperature for 72 hours. The reaction was filtered and the resulting clear solution was dumped onto ice (500 ml). The precipitate was filtered and the solid was dissolved in DCM. The organic solution was dried over sodium sulfate, filtered, and concentrated. The crude product was purified by flash chromatography using a solvent gradient of 0–1–3% MeOH in CH2Cl$_2$ with 0.1% TEA to yield 2-{4-[4-(2-chloro-3-pyridyl)imidazolyl]butyl}isoindole-1,3-dione (3.47 g, 19%). MH$^+$(381).

4-[4-(2-chloro-3-pyridyl)imidazolyl]butylamine

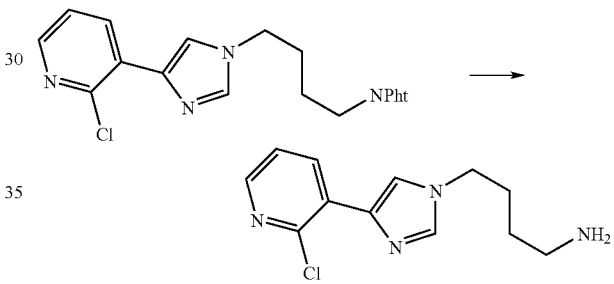

C. 4-[4-(2-chloro-3-pyridyl)imidazolyl]butylamine. To a solution of 2-{4-[4-(2-chloro-3-pyridyl)imidazolyl]butyl}isoindole-1,3-dione (2.0 g, 5.26 mmoles) in ethanol (53 ml) was added hydrazine (0.5 ml, 15.8 mmoles). After heating the reaction mixture in a 80° C. oil bath for 2.5 hours, the solution was cooled, filtered, and concentrated. The resulting oil was taken up in dichloromethane (400 ml) and was washed with 1M NaOH (20 ml). The aqueous layer was extracted further with dichloromethane (2×200 ml), the combined organics were dried over MgSO$_4$, filtered and concentrated yielding 4-[4-(2-chloro-3-pyridyl)imidazolyl]butylamine (1.09 g, 83%). MH$^+$(251).

EXAMPLE 2(L)

4-[4-(6-CHLORO-5-METHYL-3-PYRIDYL)IMIDAZOLYL]BUTYLAMINE

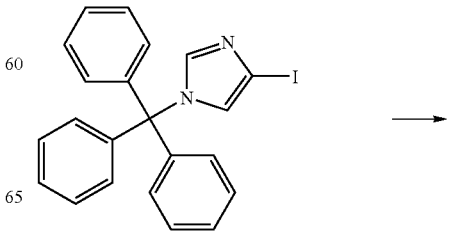

-continued

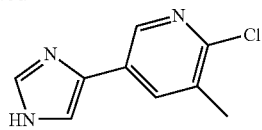

A. 4-(6-chloro-5-methyl-3-pyridyl)imidazole. To a solution of 4-iodo-1-trityl-1H-imidazole (25 g, 57.3 mmoles) in THF (250 ml) at room temperature was added ethylmagnesium bromide (69 ml, 69 mmoles) under dry conditions. After stirring for 90 minutes, zinc chloride (9.4 g, 68.6 mmoles) was added to the reaction mixture. After stirring for another 90 minutes, tetrakis(triphenylphosphine)palladium (6.6 g, 5.72 mmoles) and 5-bromo-3-methyl-2-chloropyridine (14.2 g, 68.6 mmoles) were added to the reaction mixture. Following that, the reaction mixture was heated in a 70° C. oil bath overnight. Upon cooling, the reaction was diluted with dichloromethane and washed with an EDTA buffer (at approximate pH 9) (300 ml), NaCl (sat.) (150 ml), dried over sodium sulfate, filtered, and concentrated. To the crude material in DCM (250 ml) at room temperature was added trifluoroacetic acid (115 ml, 1.5 moles). After stirring for 90 minutes, the excess TFA and DCM were removed in vacuo. The crude product was left under high vacuum pump overnight. To the crude product was added 60 ml of 3N HCl and the mixture was left in the sonicator for 120 minutes. Once recovered from the sonicator, the mixture was filtered and the aqueous solution was washed with diethyl ether until the organic phase was no more UV active. The aqueous solution was cooled to 0° C. and 30% NaOH solution was added until an approximate pH 7–8 was obtained. The obtained solid product was filtered and dried over night under high vacuum pump to yield 2-chloro-5-(1H-imidazol-4-yl)-3-methyl-pyridine (8.156 g, 74%). MH$^+$(194).

2-{4-[4-(6-chloro-5-methyl-pyridin-3-yl)-imidazol-1-yl]-butyl}-isoindole-1,3-dione

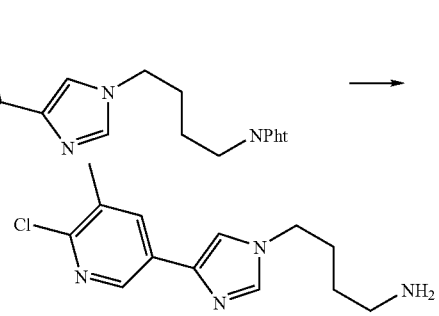

B. 2-{4-[4-(6-Chloro-5-methyl-pyridin-3-yl)-imidazol-1-yl]-butyl}-isoindole-1,3-dione. To a solution of 2-chloro-5-(1H-imidazol-4-yl)-3-methyl-pyridine (8.2 g, 42.3 mmoles) in DMF (80 ml) was added potassium carbonate (29 g, 212 mmoles) and N-(4-bromobutyl)phthalimide (30 g, 106 mmoles) at room temperature under dry conditions. The solution was left stirring at room temperature overnight. The reaction was filtered and the resulting clear solution was dumped onto ice (1 L). The precipitate was filtered and the solid was dissolved in DCM. The organic solution was dried over sodium sulfate, filtered and concentrated. The crude product was purified by flash chromatography using first a solvent gradient of 99% DCM, 1% MeOH, and 0.1% TEA, then 97% DCM, 3% MeOH, and 0.1% TEA to yield 2-{4-[4-(6-chloro-5-methyl-pyridin-3-yl)-imidazol-1-yl]-butyl}-isoindole-1,3-dione (4.0 g, 27%). MH$^+$(395).

4-[4-(6-chloro-5-methyl-3-pyridyl)imidazolyl]butylamine

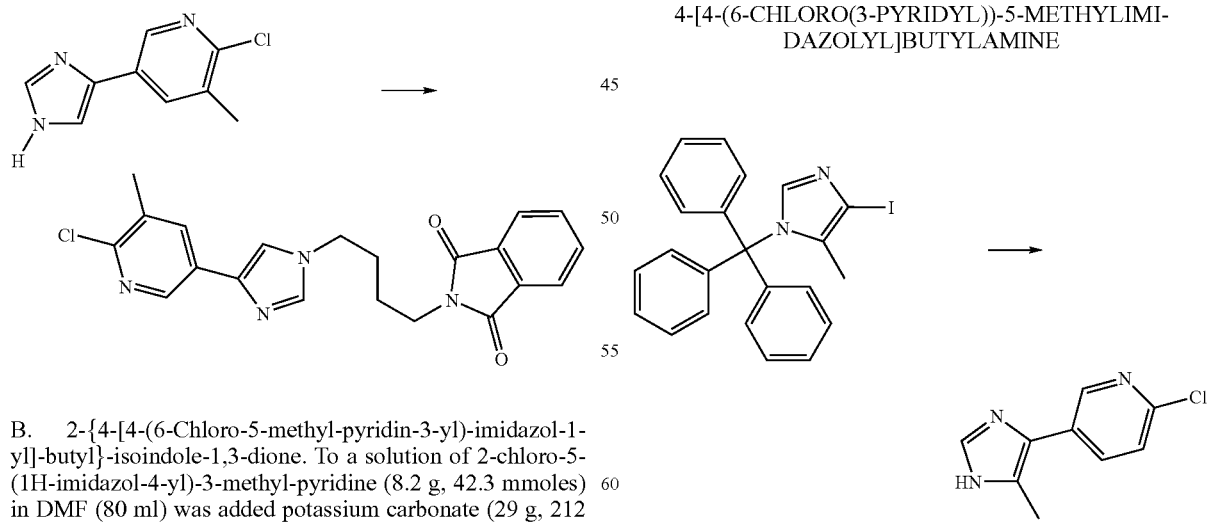

C. 4-[4-(6-chloro-5-methyl-3-pyridyl)imidazolyl]butylamine. To a solution of 2-{4-[4-(6-chloro-5-methyl-pyridin-3-yl)-imidazol-1-yl]-butyl}-isoindole-1,3-dione (3.97 g, 10.07 mmoles) in ethanol (100 ml) was added hydrazine (0.95 ml, 30.22 mmoles). After heating the reaction mixture in a 80° C. oil bath for 3 hours, the solution was cooled, filtered, and concentrated. The resulting oil was taken up in dichloromethane (400 ml) and was washed with 1M NaOH (20 ml). The aqueous layer was extracted further with dichloromethane (3×200 ml), the combined organics were dried over MgSO$_4$, filtered, and concentrated yielding 4-[4-(6-chloro-5-methyl-3-pyridyl)imidazolyl]butylamine (2.14 g, 86%). MH$^+$(265).

EXAMPLE 2(M)

4-[4-(6-CHLORO(3-PYRIDYL))-5-METHYLIMIDAZOLYL]BUTYLAMINE

A. 2-Chloro-5-(5-methyl-1H-imidazol-4-yl)-pyridine. To a solution of 4-iodo-5-methyl-1-trityl-1H-imidazole (25.0 g, 56 mmoles) in THF (250 ml) at room temperature was added ethylmagnesium bromide (61 ml, 61 mmoles) under dry conditions. After stirring for 90 minutes, zinc chloride (8.3 g, 6 mmoles) was added to the reaction mixture. After stirring for another 90 minutes, tetrakis(triphenylphosphine) palladium (6.0 g, 61 mmoles) and 5-bromo-2-chloropyridine (12.8 g, 66.7 mmoles) were added to the reaction mixture. Following that, the reaction mixture was heated in a 70° C. oil bath overnight. Upon cooling, the reaction was filtered and the filtrate was diluted with dichloromethane (500 ml) and washed with an EDTA buffer (at approximate pH 9) (300 ml), NaCl (sat.) (300 ml), dried over sodium sulfate, filtered, and concentrated. To a solution of crude 2-chloro-5-(5-methyl-1-trityl-1H-imidazol-4-yl)-pyridine (24 g, 55.6 mmoles) in DCM (250 ml) at room temperature was added trifluoroacetic acid (60 ml, 780 moles). After stirring for 90 minutes, the excess TFA and DCM were removed in vacuo. The crude product was left under high vacuum pump overnight. To the crude product was added 60 ml of 3N HCl and the mixture was left in the sonicator for 120 minutes. Once recovered from the sonicator, the mixture was filtered and the aqueous solution was washed with diethyl ether until the organic phase was no more UV active. The aqueous solution was cooled to 0° C. and 30% NaOH solution was added until an approximate pH 7–8 was obtained. The obtained solid product was filtered and dried over night under high vacuum pump to yield 2-chloro-5-(5-methyl-1H-imidazol-4-yl)-pyridine (5.56 g, 52%). MH$^+$(194).

2-{4-[4-(6-chloro(3-pyridyl))-5-methylimidazolyl]butyl}-isoindole-1,3-dione

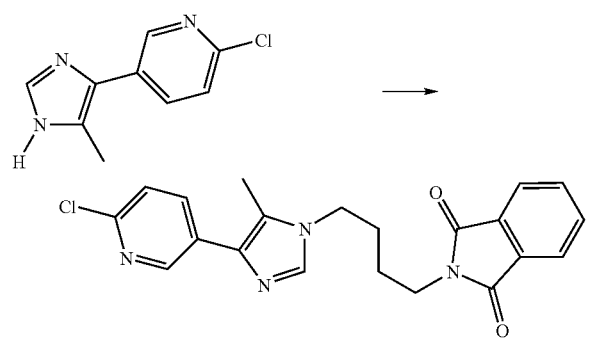

B. 2-{4-[4-(6-chloro(3-pyridyl))-5-methylimidazolyl]butyl}-isoindole-1,3-dione. To a solution of 4-(6-chloro(3-pyridyl))-5-methylimidazole (2.22 g, 11.44 mmoles) in DMF (45 ml) was added potassium carbonate (7.9 g, 57.2 mmoles) and N-(4-bromobutyl)phthalimide (6.5 g, 22.9 mmoles) at room temperature under dry conditions. The solution was left stirring at room temperature for 48 hours. The reaction was filtered and the resulting clear solution was dumped onto ice (300 ml). The precipitate was filtered and the solid was dissolved in DCM. The organic solution was dried over sodium sulfate, filtered, and concentrated. The crude product was purified by flash chromatography using first a solvent gradient of 99% DCM, 1% MeOH, and 0.1% TEA, then 97% DCM, 3% MeOH, and 0.1% TEA to yield 2-{4-[4-(6-chloro(3-pyridyl))-5-methylimidazolyl]butyl}-isoindole-1,3-dione (415 mg, 9%). MH$^+$(396).

4-[4-(6-chloro(3-pyridyl))-5-methylimidazolyl]butylamine

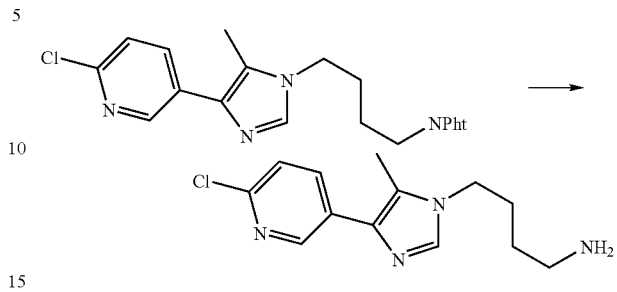

C. 4-[4-(6-chloro(3-pyridyl))-5-methylimidazolyl]butylamine. To a solution of 2-{4-[4-(6-chloro(3-pyridyl))-5-methylimidazolyl]butyl}isoindole-1,3-dione (405 g, 1.05 mmoles) in ethanol (10 ml) was added hydrazine (0.14 ml, 4.2 mmoles). After heating the reaction mixture in a 65° C. oil bath for 15 hours, the solution was cooled, filtered, and concentrated. The resulting oil was taken up in dichloromethane (100 ml) and was washed with 1M NaOH (5 ml). The aqueous layer was extracted further with dichloromethane (3×100 ml), the combined organics were dried over MgSO$_4$, filtered, and concentrated yielding 4-[4-(6-chloro(3-pyridyl))-5-methylimidazolyl]butylamine (214 mg, 76%). MH$^+$(266).

EXAMPLE 2(N)

4-[4-(6-METHOXY(3-PYRIDYL))-5-METHYLIMIDAZOLYL]BUTYLAMINE

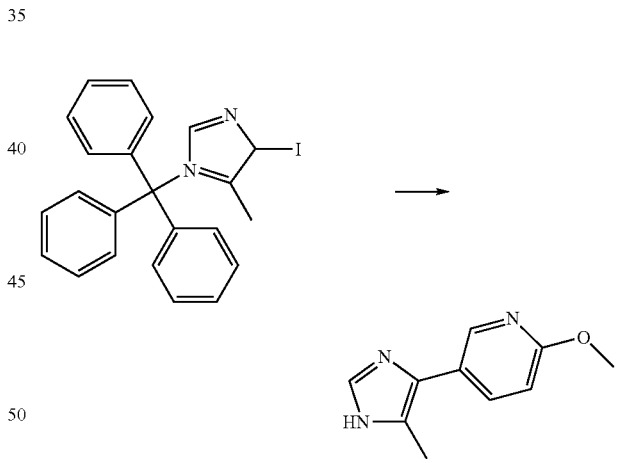

A. 2-methoxy-5-(5-methylimidazol-4-yl)pyridine. To a solution of 4-iodo-5-methyl-1-trityl-1H-imidazole (25.0 g, 56 mmoles) in THF (250 ml) at room temperature was added ethylmagnesium bromide (61 ml, 61 mmoles) under dry conditions. After stirring for 90 minutes, zinc chloride (8.3 g, 6 mmoles) was added to the reaction mixture. After stirring for another 90 minutes, tetrakis(triphenylphosphine) palladium (6.0 g, 61 mmoles) and 5-bromo-2-methoxypyridine (8.62 ml, 66.7 mmoles) were added to the reaction mixture. Following that, the reaction mixture was heated in a 65° C. oil bath overnight. Upon cooling, the reaction was diluted with dichloromethane (1 L) and washed with a 30% NaOH+10% EDTA solution (3×200 ml), washed with NaCl (sat.) (300 ml), dried over sodium sulfate, filtered, and concentrated. To the crude material (16.1 g) in dichloromethane (250 ml) at room temperature was added trifluoroacetic acid (27.8 ml, 373.3 moles). After stirring for 24 hours, the excess TFA and DCM were removed in vacuo. The crude product was left under high vacuum pump overnight. To the crude product was added 60 ml of 3N HCl and the mixture was sonicated for 120 minutes. Once recovered from the sonicator, the mixture was filtered and the aqueous solution was washed with diethyl ether until the organic phase was no longer UV active. The aqueous solution was cooled to 0° C. and 30% NaOH solution was added until an approximate pH 7–8 was obtained. The obtained solid product was filtered and dried over night under high vacuum pump to yield 2-methoxy-5-(5-methylimidazol-4-yl)pyridine (3.9 g, 55%). MH$^+$(190).

2-{4-[4-(6-methoxy(3-pyridyl))-5-methylimidazolyl]butyl}-isoindole-1,3-dione

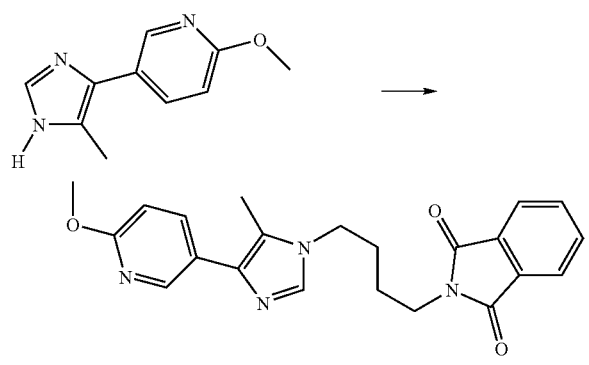

B. 2-{4-[4-(6-methoxy(3-pyridyl))-5-methylimidazolyl]butyl}-isoindole-1,3-dione. To a solution of sodium hydride, 60% dispersion (1.8 g, 44.75 mmoles) in DMF (9 ml) at 0° C. was added a solution of 2-methoxy-5-(5-methylimidazol-4-yl)pyridine (3.4 g, 17.9+mmoles) in DMF (18 ml) dropwise. A solution of N-(4-bromobutyl)phthalimide (7.6 g, 26.9 mmoles) in DMF (12 ml) was than added. The reaction was held at 0° C. for 22 hours, at which time it was dumped onto ice (400 g). The precipitate was filtered and the solid was dissolved in DCM. The organic solution was dried over sodium sulfate, filtered and concentrated. The crude product was purified by flash chromatography using a solvent gradient of 0–1–3% MeOH in CH$_2$Cl$_2$ with 0.1% TEA to yield 2-{4-[4-(6-methoxy(3-pyridyl))-5-methylimidazolyl]butyl}-isoindole-1,3-dione (1.6 g, 24%). MH$^+$(391).

4-[4-(6-methoxy(3-pyridyl))-5-methylimidazolyl]butylamine

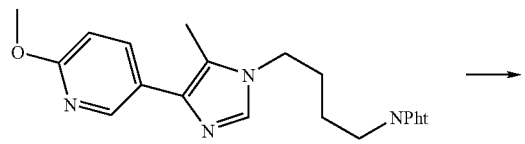

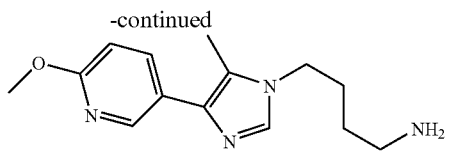

C. 4-[4-(6-methoxy(3-pyridyl))-5-methylimidazolyl]butylamine. To a solution of 2-{4-[4-(6-methoxy(3-pyridyl))-5-methylimidazolyl]butyl} isoindole-1,3-dione (664 mg, 1.7 mmoles) in ethanol (17 ml) was added hydrazine (0.16 ml, 5.1 mmoles). After heating the reaction mixture in a 80° C. oil bath for 3 hours, the solution was cooled, filtered, and concentrated. The resulting oil was taken up in dichloromethane (100 ml) and was washed with 1M NaOH (15 ml). The aqueous layer was extracted further with dichloromethane (2×100 ml), the combined organics were dried over MgSO$_4$, filtered, and concentrated yielding 4-[4-(6-methoxy(3-pyridyl))-5-methylimidazolyl]butylamine (287 mg, 65%). MH$^+$(261).

EXAMPLE 2(N)

4-[4-(6-METHOXY(3-PYRIDYL))-2-METHYLIMIDAZOLYL]BUTYLAMINE

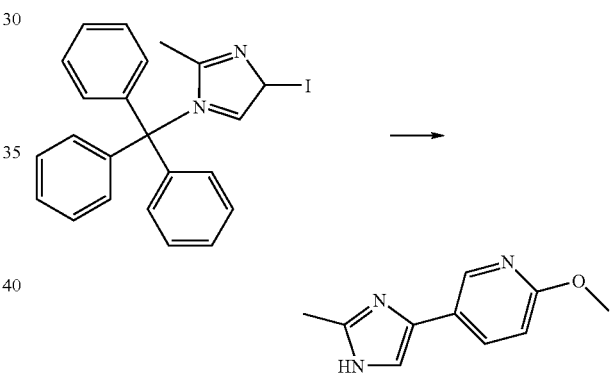

A. 2-methoxy-5-(2-methylimidazol-4-yl)pyridine. To a solution of 4-iodo-2-methyl-1-trityl-1H-imidazole (31.5 g, 70 mmoles) in THF (300 ml) at room temperature was added ethylmagnesium bromide (84 ml, 84 mmoles) under dry conditions. After stirring for 90 minutes, zinc chloride (11.44 g, 84 mmoles) was added to the reaction mixture. After stirring for another 90 minutes, tetrakis(triphenylphosphine)palladium (8.1 g, 7.0 mmoles) and 5-bromo-2-methoxypyridine (10.9 ml, 84 mmoles) were added to the reaction mixture. Following that, the reaction mixture was heated in a 65° C. oil bath overnight. Upon cooling, the reaction was diluted with dichloromethane (1 L) and washed with a 30% NaOH+10% EDTA solution (3×200 ml), washed with NaCl (sat.) (300 ml), dried over sodium sulfate, filtered, and concentrated. To the crude material in dichloromethane (250 ml) at room temperature was added trifluoroacetic acid (27.8 ml, 373.3 moles). After stirring for 24 hours, the excess TFA and DCM were removed in vacuo. The crude product was left under high vacuum pump overnight. To the crude product was added 60 ml of 3N HCl and the mixture was sonicated for 120 minutes. Once recovered from the sonicator, the mixture was filtered and the aqueous solution was washed with diethyl ether until the organic phase was no longer UV active. The aqueous solution was cooled to 0° C. and 30% NaOH solution was added until an approximate pH 7–8 was obtained. The obtained solid product was filtered and dried over night under high vacuum pump to yield 2-methoxy-5-(2-methylimidazol-4-yl)pyridine (5.0 g, 38%). MH⁺(190).

2-{4-[4-(6-methoxy(3-pyridyl))-2-methylimidazolyl]butyl}-isoindole-1,3-dione

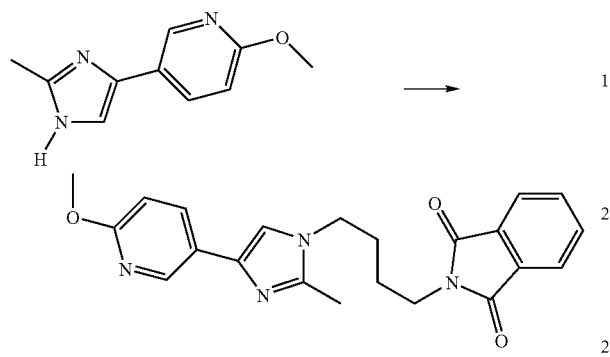

B. 2-{4-[4-(6-methoxy(3-pyridyl))-2-methylimidazolyl]butyl}-isoindole-1,3-dione. To a solution of 2-methoxy-5-(2-methylimidazol-4-yl)pyridine (5.0 g, 26.4 mmoles) in DMF (100 ml) was added potassium carbonate (18.3 g, 132 mmoles) and N-(4-bromobutyl)phthalimide (8.97 g, 31.7 mmoles) at room temperature under dry conditions. The solution was left stirring at room temperature for 72 hours. The reaction was filtered and the resulting clear solution was dumped onto ice (1 L). The precipitate was filtered and rinsed with water (2×200 ml) and was pumped on for 1 hour. The material was than rinsed with diethyl ether (7×200 ml) and than was pumped on to yield to yield 2-{4-[4-(6-methoxy(3-pyridyl))-2-methylimidazolyl]butyl}-isoindole-1,3-dione (4.1 g, 48%). MH⁺(391).

4-[4-(6-methoxy(3-pyridyl))-2-methylimidazolyl]butylamine

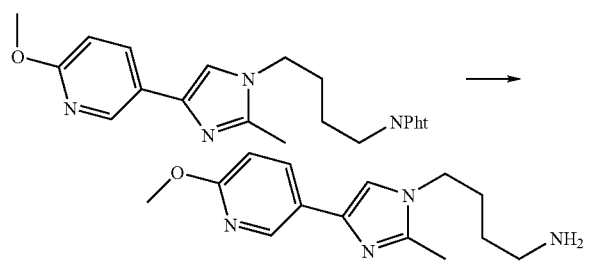

C. 4-[4-(6-methoxy(3-pyridyl))-2-methylimidazolyl]butylamine. To a solution of 2-{4-[4-(6-methoxy(3-pyridyl))-2-methylimidazolyl]butyl}-isoindole-1,3-dione (900 mg, 2.3 mmoles) in ethanol (23 ml) was added hydrazine (0.22 ml, 6.9 mmoles). After heating the reaction mixture in a 80° C. oil bath for 3 hours, the solution was cooled, filtered, and concentrated. The resulting oil was taken up in dichloromethane (100 ml) and was washed with 1M NaOH (15 ml). The aqueous layer was extracted further with dichloromethane (2×100 ml), the combined organics were dried over MgSO₄, filtered, and concentrated yielding 4-[4-(6-methoxy(3-pyridyl))-2-methylimidazolyl]butylamine (600 mg, 100%). MH⁺(261).

EXAMPLE 2(P)

4-[4-(6-CHLORO(3-PYRIDYL))-2-METHYLIMIDAZOLYL]BUTYLAMINE

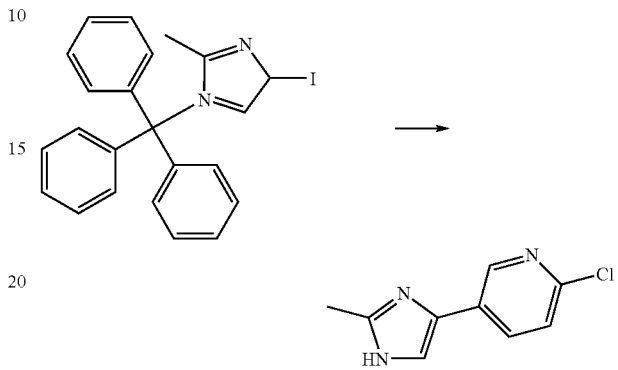

A. 2-chloro-5-(2-methylimidazol-4-yl)pyridine. To a solution of 4-iodo-2-methyl-1-trityl-1H-imidazole (25.9 g, 57.6 mmoles) in THF (20 ml) at room temperature was added ethylmagnesium bromide (69 ml, 69 mmoles) under dry conditions. After stirring for 90 minutes, zinc chloride (9.4 g, 69 mmoles) was added to the reaction mixture. After stirring for another 90 minutes, tetrakis(triphenylphosphine)palladium (6.66 g, 5.76 mmoles) and 5-bromo-2-chloropyridine (13.3 g, 69.0 mmoles) were added to the reaction mixture. Following that, the reaction mixture was heated in a 65° C. oil bath overnight. Upon cooling, the reaction was diluted with dichloromethane (1 L) and washed with a 30% NaOH+10% EDTA solution (3×200 ml), washed with NaCl (sat.) (300 ml), dried over sodium sulfate, filtered and concentrated. To the crude material (16.1 g) in dichloromethane (250 ml) at room temperature was added trifluoroacetic acid (27.8 ml, 373.3 mmoles). After stirring for 24 hours, the excess TFA and DCM were removed in vacuo. The crude product was left under high vacuum pump overnight. To the crude product was added 60 ml of 3N HCl and the mixture was sonicated for 120 minutes. Once recovered from the sonicator, the mixture was filtered and the aqueous solution was washed with diethyl ether until the organic phase was no longer UV active. The aqueous solution was cooled to 0° C. and 30% NaOH solution was added until an approximate pH 7–8 was obtained. The obtained solid product was filtered and dried over night under high vaucum pump to yield 2-chloro-5-(2-methylimidazol-4-yl)pyridine (3.5 g, 31%). MH⁺(194).

2-{4-[4-(6-chloro(3-pyridyl))-2-methylimidazolyl]butyl}-isoindole-1,3-dione

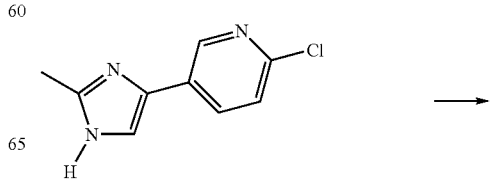

-continued

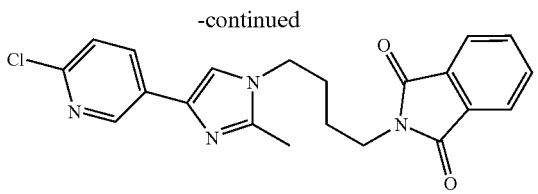

B. 2-{4-[4-(6-chloro(3-pyridyl))-2-methylimidazolyl]butyl}-isoindole-1,3-dione. To a solution of 2-chloro-5-(2-methylimidazol-4-yl)pyridine (3.5 g, 18 mmoles) in DMF (50 ml) was added potassium carbonate (12.4 g, 90 mmoles) and N-(4-bromobutyl)phthalimide (15.4 g, 54 mmoles) at room temperature under dry conditions. The solution was left stirring at room temperature for 48 hours. The reaction was filtered and the resulting clear solution was dumped onto ice (0.5 L). The precipitate was filtered and rinsed with water (2×200 ml) and was pumped on for 1 hour. The crude product was rinsed with diethyl ether (4×200 ml) and was purified than by flash chromatography using a solvent gradient of 0–1–3% MeOH in $CH_2Cl_2$ with 0.1% TEA to yield 2-{4-[4-(6-chloro(3-pyridyl))-2-methylimidazolyl]butyl}-isoindole-1,3-dione (4.3 g, 61%). $MH^+$(395).

4-[4-(6-chloro(3-pyridyl))-2-methylimidazolyl]butylamine

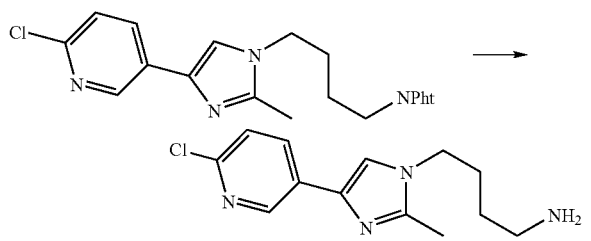

C. 4-[4-(6-chloro(3-pyridyl))-2-methylimidazolyl]butylamine. To a solution of 2-{4-[4-(6-chloro(3-pyridyl))-2-methylimidazolyl]butyl}-isoindole-1,3-dione (1.0 g, 2.54 mmoles) in ethanol (25 ml) was added hydrazine (0.24 ml, 7.6 mmoles). After heating the reaction mixture in a 80° C. oil bath for 3 hours, the solution was cooled, filtered, and concentrated. The resulting oil was taken up in dichloromethane (100 ml) and was washed with 1M NaOH (15 ml). The aqueous layer was extracted further with dichloromethane (2×100 ml), the combined organics were dried over $MgSO_4$, filtered, and concentrated yielding 4-[4-(6-chloro(3-pyridyl))-5-methylimidazolyl]butylamine (500 mg, 75%). $MH^+$(265).

EXAMPLE 2(Q)

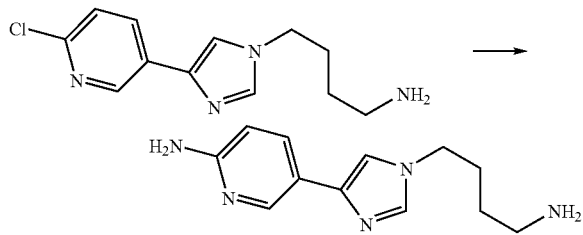

5-[1-(4-amino-butyl)-1H-imidazol-4-yl]-pyridin-2-ylamine is made by treating 4-[4-(6-fluor-3-pyridyl)imidazolyl]butylamine with $NH_3$ saturated ethanol in a sealed bomb at 160*C for 16 hours.

EXAMPLE 3

COMPOUND B

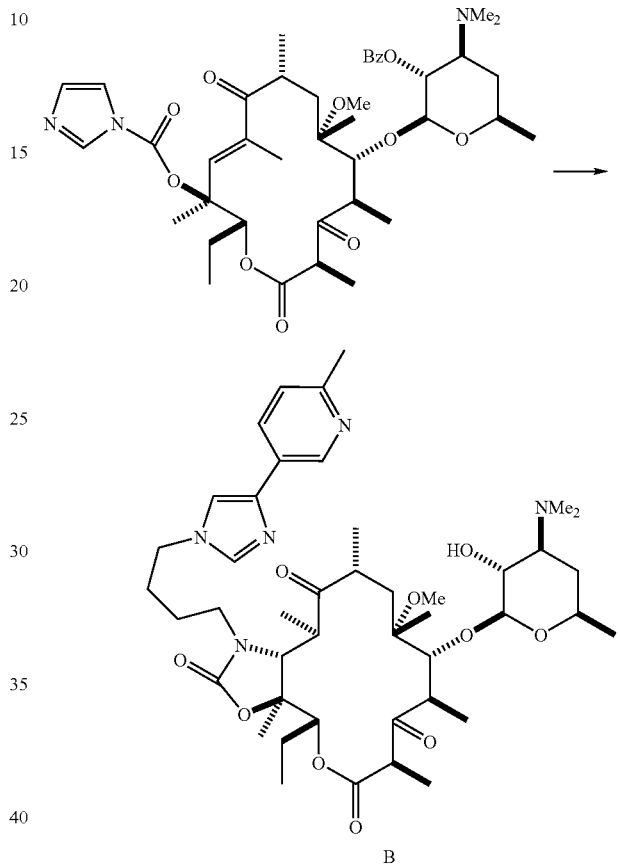

Following Procedure A, as described below, with a methyl imidazolyl carbamate ketolide and 4-[4-(6-methyl-pyridin-3-yl)-imidazol-1-yl]-butylamine yields compound B.

Procedure A: A 0.25M solution of a methyl imidazolyl carbamate ketolide (1 eq.) and 4-[4-(6-methyl-pyridin-3-yl)-imidazol-1-yl]-butylamine (2.0 equivalents) in 10:1 acetonitrile:water was heated in a 65° C. oil bath for 12 hours. Upon cooling the reaction was diluted with ethyl acetate and washed with $NaHCO_3$ (sat.) (3×), NaCl (sat.) (1×), dried over $MgSO_4$, filtered, and concentrated. A 0.05M solution of the crude material in methanol was heated at 65° C. for 16 hours. The material is concentrated and purified by RP HPLC and/or silica chromatography. $^1H$ NMR (CDCl3, referenced at 7.26 ppm on 300 MHz NMR): 8.84 (1H, d), 7.98 (1H, dd), 7.52 (1H, d) 7.27 (1H, d), 7.14 (1H, d), 4.92(1H, dd), 4.30 (1H, d), 4.22 (1H, d), 7.98 (1H, dd), 3.84 (1H, q), 3.6–3.8 (2H, m), 3.54 (1H, s), 3.5–3.6 (1H, m), 3.24 (1H, dd), 3.04–3.16 (4H, m), 2.6 (4H, bs), 2.54 (3H, s), 2.38 (6H, s), 1.8–2.0 (4H, m), 1.5–1.76 (4H, m) 1.5 (3H, s), 1.24–1.4 (14H, m), 1.18 (3H, d), 1.0 (3H, d), 0.84 (3H, t).

EXAMPLE 4

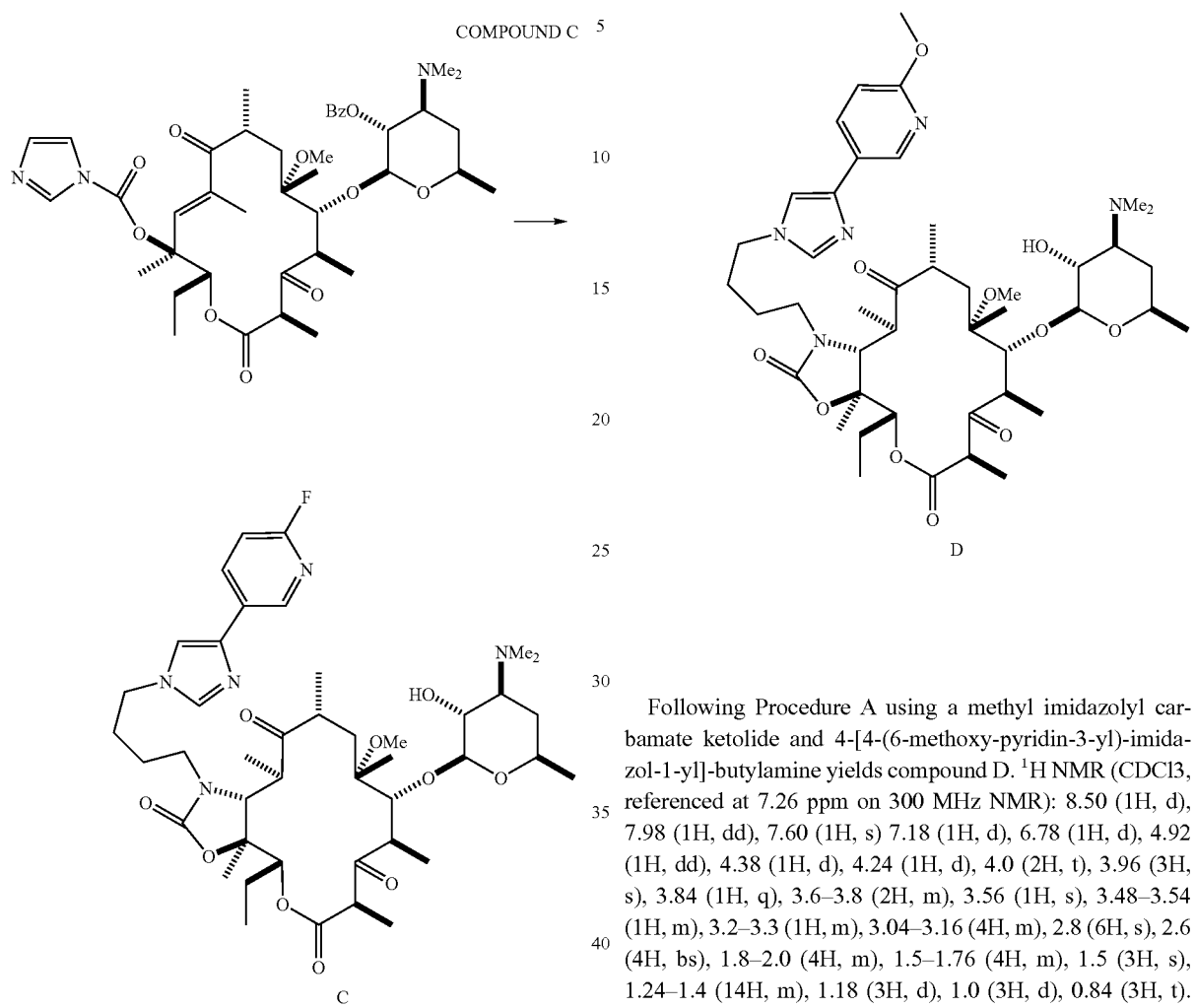

Following Procedure A using a methyl imidazolyl carbamate ketolide and 4-[4-(6-fluoro-pyridin-3-yl)-imidazol-1-yl]-butylamine yields Compound C.

EXAMPLE 5

Following Procedure A using a methyl imidazolyl carbamate ketolide and 4-[4-(6-methoxy-pyridin-3-yl)-imidazol-1-yl]-butylamine yields compound D. $^1$H NMR (CDCl3, referenced at 7.26 ppm on 300 MHz NMR): 8.50 (1H, d), 7.98 (1H, dd), 7.60 (1H, s) 7.18 (1H, d), 6.78 (1H, d), 4.92 (1H, dd), 4.38 (1H, d), 4.24 (1H, d), 4.0 (2H, t), 3.96 (3H, s), 3.84 (1H, q), 3.6–3.8 (2H, m), 3.56 (1H, s), 3.48–3.54 (1H, m), 3.2–3.3 (1H, m), 3.04–3.16 (4H, m), 2.8 (6H, s), 2.6 (4H, bs), 1.8–2.0 (4H, m), 1.5–1.76 (4H, m), 1.5 (3H, s), 1.24–1.4 (14H, m), 1.18 (3H, d), 1.0 (3H, d), 0.84 (3H, t).

EXAMPLE 6

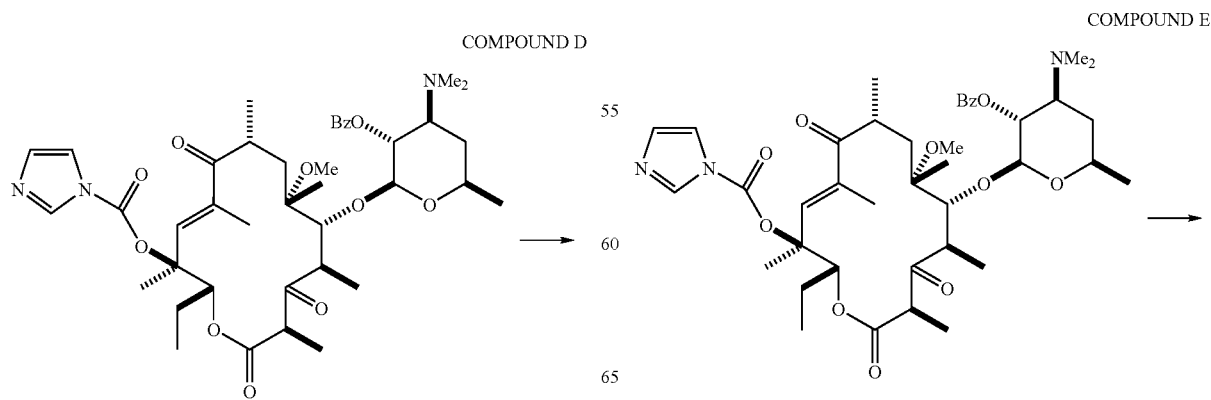

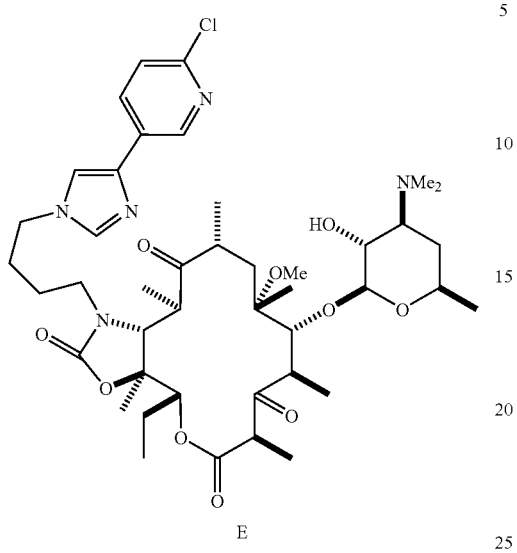

E

Following Procedure A using a methyl imidazolyl carbamate ketolide and 4-[4-(6-chloro-pyridin-3-yl)-imidazol-1-yl]-butylamine yields compound E. ¹H NMR (CDCl3, referenced at 7.26 ppm on 300 MHz NMR): 8.52 (1H, d), 8.04 (1H, dd), 7.52 (1H, s) 7.32(1H, d), 7.28(1H, d), 4.90(1H, dd), 4.28(1H, d), 4.22(1H, d), 4.0 (2H, t), 3.84 (1H, q), 3.6–3.8 (2H, m), 3.54 (1H, s), 3.50–3.54 (1H, m), 3.0–3.20 (4H, m), 2.6 (4H, bs), 2.44 (1H, m), 2.24 (6H, s), 1.8–2.0 (4H, m), 1.5–1.7 (5H, m), 1,46 (3H, s), 1.24–1.4 (10H, m), 1.22 (3H, d), 1.18 (3H, d), 1.0 (3H, d), 0.84 (3H, t).

EXAMPLE 7

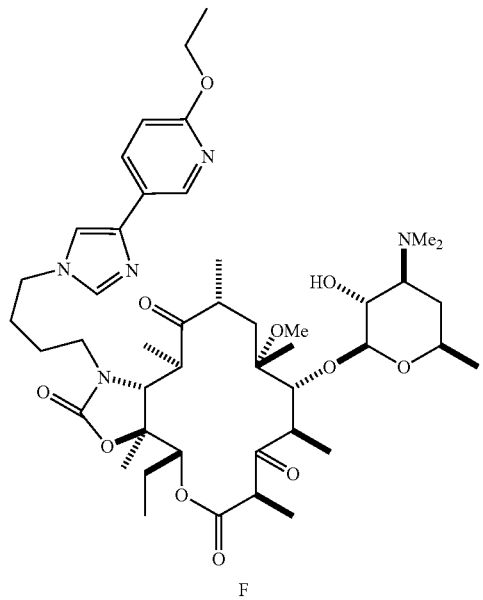

F

Following Procedure A using a methyl imidazolyl carbamate ketolide and 4-[4-(6-ethoxy-pyridin-3-yl)-imidazol-1-yl]-butylamine yields compound F.

EXAMPLE 8

COMPOUND F                    COMPOUND G

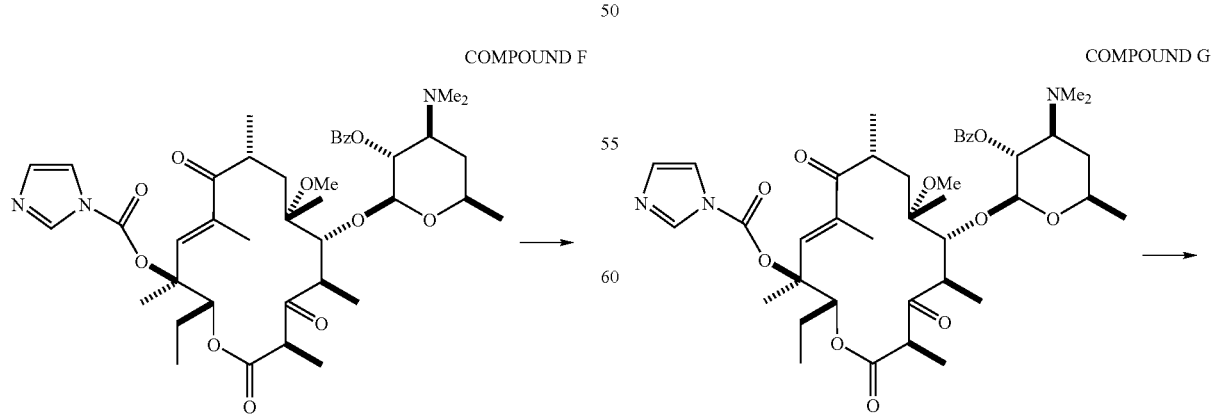

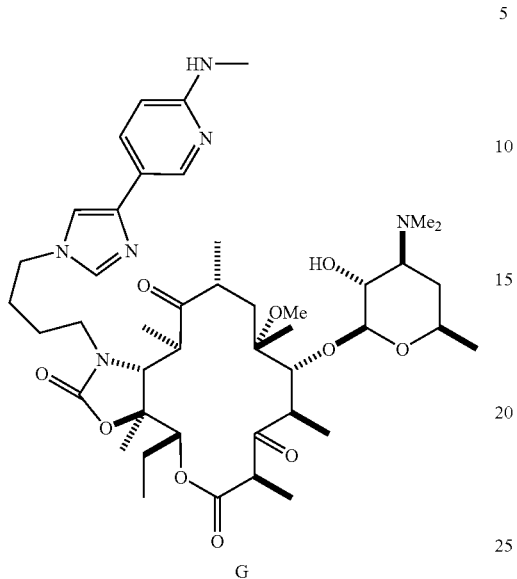
G
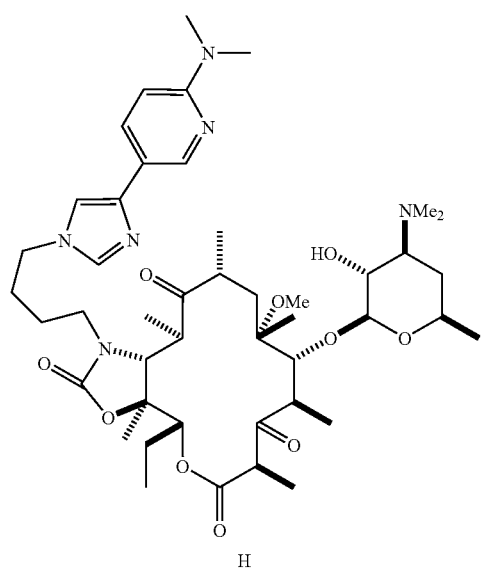
H
Following Procedure A using a methyl imidazolyl carbamate ketolide and {5-[1-(4-aminobutyl)imidazol-4-yl](2-pyridyl)}methylamine yields compound G.
Following Procedure A using a methyl imidazolyl carbamate ketolide and {5-[1-(4-aminobutyl)imidazol-4-yl](2-pyridyl)}dimethylamine yields compound H.
EXAMPLE 9
EXAMPLE 10
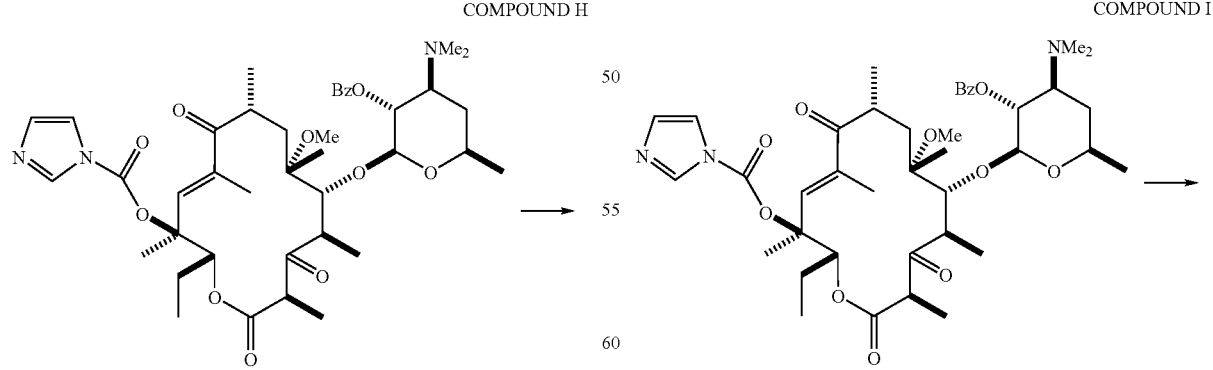
COMPOUND H
COMPOUND I

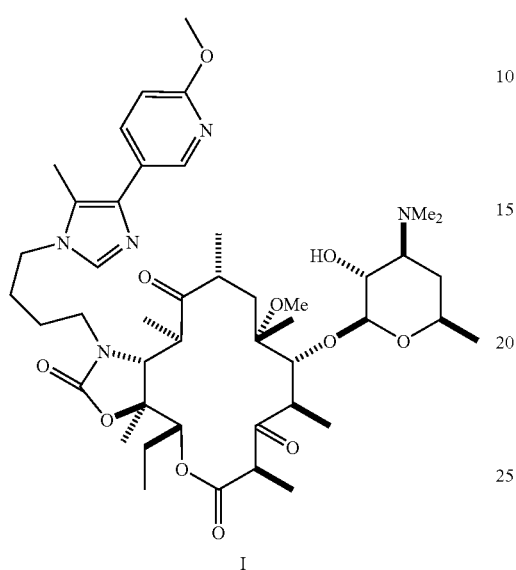
I
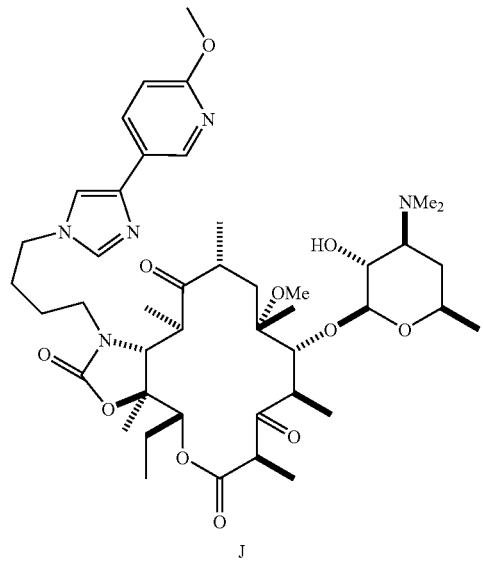
J
Following Procedure A using a methyl imidazolyl carbamate ketolide and 4-[4-(6-methoxy(3-pyridyl))-5-methylimidazolyl]butylamine yields compound I.
Following Procedure A using a methyl imidazolyl carbamate ketolide and 4-[4-(6-methoxy(3-pyridyl))-2-methylimidazolyl]butylamine yields compound J.
EXAMPLE 11
EXAMPLE 12
COMPOUND J
COMPOUND K
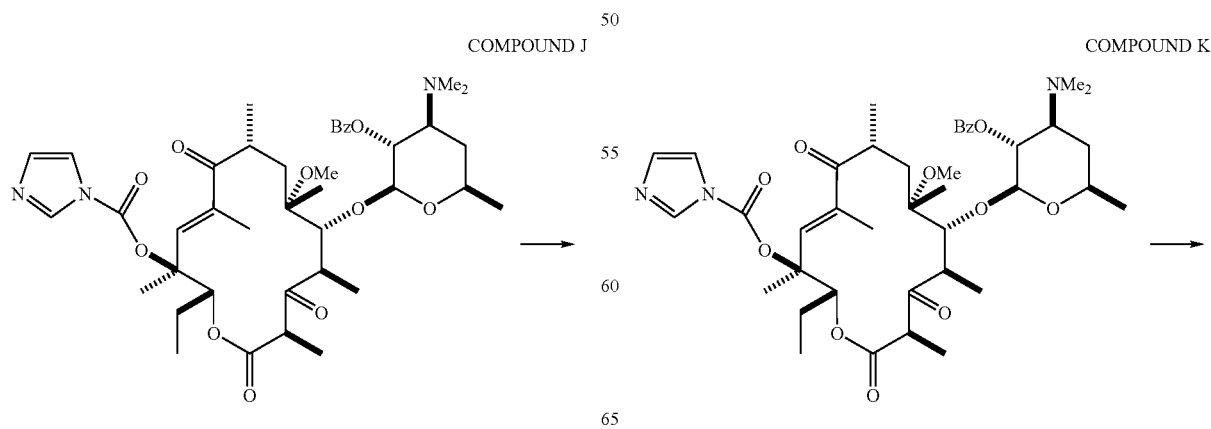

-continued

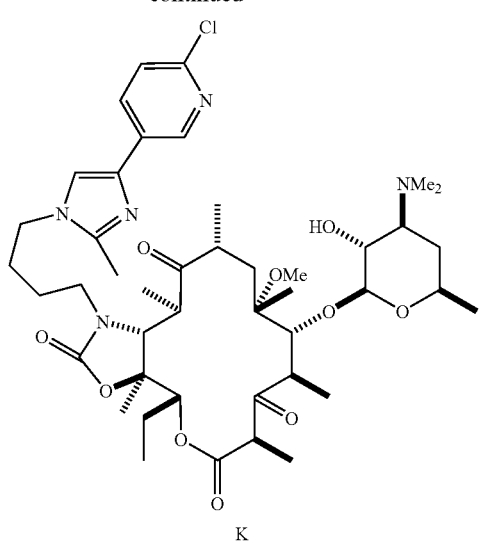

K

Following Procedure A using a methyl imidazolyl carbamate ketolide and 4-[4-(6-chloro-(3-pyridyl))-2-methylimidazolyl]butylamine yields compound K.

EXAMPLE 13

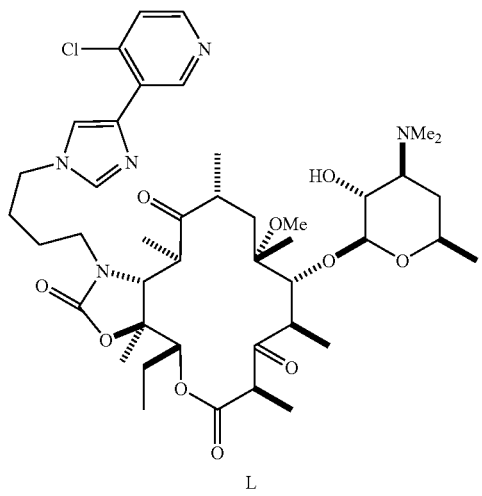

L

Following Procedure A using a methyl imidazolyl carbamate ketolide and 4-[4-(4-chloro-3-pyridyl)imidazolyl]butylamine yields compound L.

EXAMPLE 14

COMPOUND M

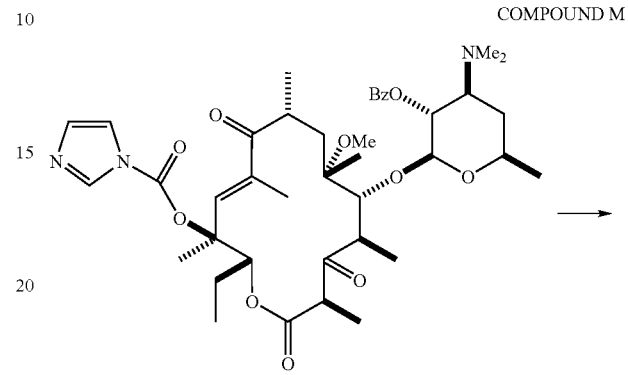

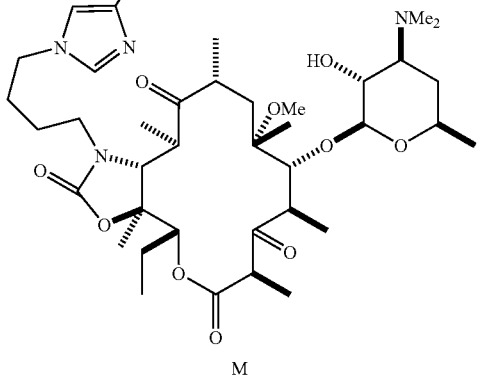

M

Following Procedure A using a methyl imidazolyl carbamate ketolide and 4-[4-(4-methoxy-3-pyridyl)imidazolyl]butylamine yields compound M.

EXAMPLE 15

COMPOUND N

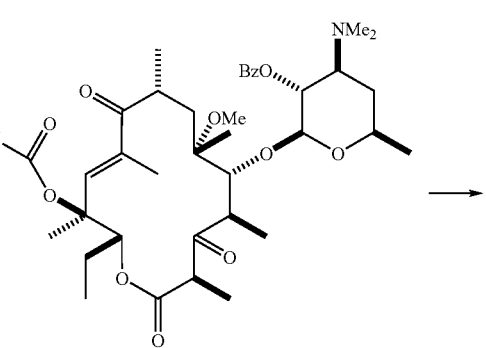

-continued

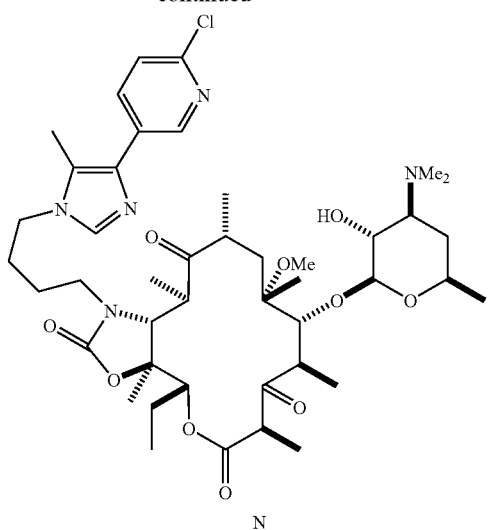

N

Following Procedure A using a methyl imidazolyl carbamate ketolide and 4-[4-(6-chloro(3-pyridyl))-5-methylimidazolyl]butylamine yields compound N.

EXAMPLE 16

COMPOUND O

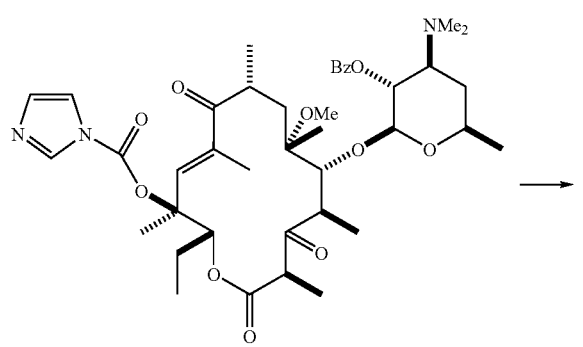

O

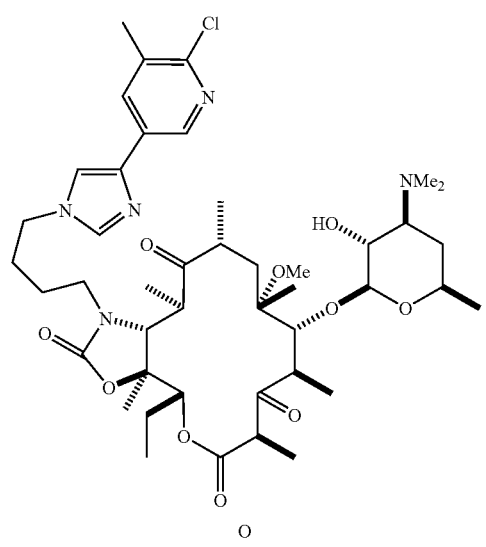

Following Procedure A using a methyl imidazolyl carbamate ketolide and 4-[4-(6-chloro-5-methyl-3-pyridyl)imidazolyl]butylamine yields compound O.

EXAMPLE 17

COMPOUND P

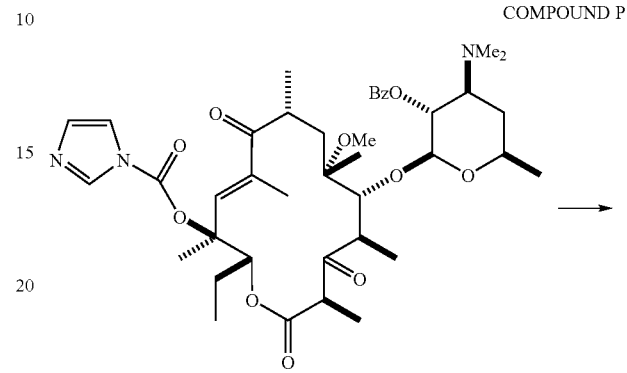

P

Following Procedure A using a methyl imidazolyl carbamate ketolide and 4-[4-(2-chloro-3-pyridyl)imidazolyl]butylamine yields compound P.

EXAMPLE 18

COMPOUND Q

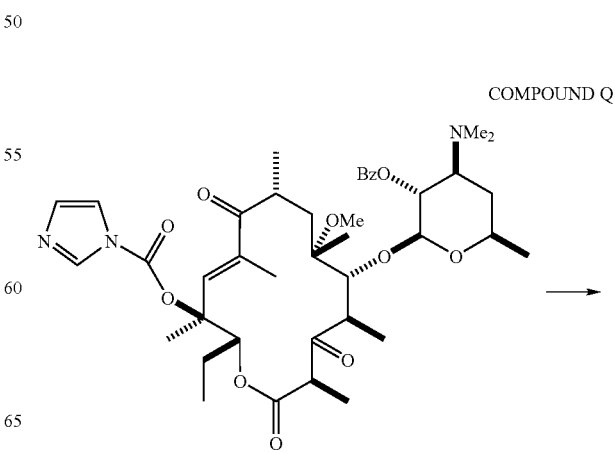

-continued

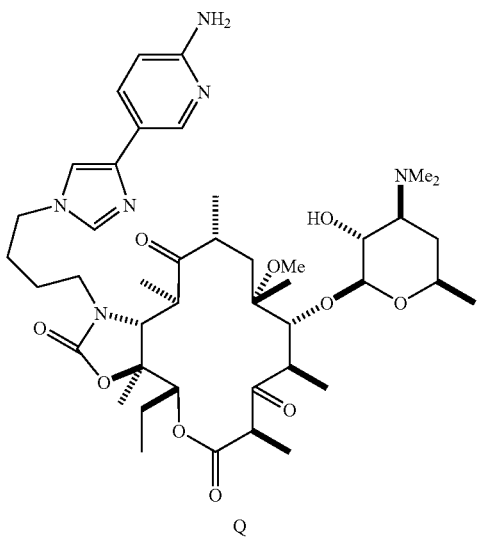

Q

Following Procedure A using a methyl imidazolyl carbamate ketolide and 5-[1-(4-amino-butyl)-1H-imidazol-4-yl]-pyridin-2-ylamine yields compound Q.

EXAMPLE 19

Antibacterial Activity

Representative compounds of the present invention are assayed in vitro for antibacterial activity against representative bacterial isolates listed in Table 1 as follows:

Strains. The bacterial isolates listed in Table 1 are cultivated from −70° C. frozen stocks by two consecutive overnight passages (P1, P2) at 35° C. on 5% blood agar (Remel, Lenexa, Kans.). Chocolate agar (Remel) is used for *Haemophilus influenzae*. *H. influenzae* and *Streptococcus pneumoniae* are incubated in 5–10% $CO_2$.

TABLE 1

| Strains | Strain ID |
| --- | --- |
| *S. epidermidis* Step__14990 | A |
| *S. epidermidis* Step__f50654 Pen S | B |
| *E. faecalis* Enfa__29212 | C |
| *S. pyogenes* Stpy__8668 | D |
| *S. pneumoniae* Stpn__49619 | E |
| *S. pneumoniae* Stpn__297–749 Pen R | F |
| *S. pneumoniae* Stpn__280–962 Pen S | G |
| *S. pneumoniae* Stpn__Erm 6849 | H |
| *S. pneumoniae* Stpn__Erm S 4297 | I |
| *S. pneumoniae* Stpn__Mef 5654 | J |
| *S. pneumoniae* Stpn__Mef S 3427 | K |
| *H. influenzae* Hain__49247 | L |
| *E. coli* Esco__25922 | M |

Drug Stock Preparation. To determine the amount of solvent to be used to give the desired final concentration, the formula "weight obtained in mg/final concentration in mg/ml" will be used. It will give the amount of solvent in ml needed to be added to give the desired concentration. For example, if 2.5 mg/ml is the desired concentration and the weight of compound is 13.7 mg, then the amount of solvent to be added is 3.94 ml (13.7 mg/2.5 mg/ml=3.94 ml). Methanol is used as the solvent to dissolve the test compounds. Further dilution of stock is done in sterile, deioinzed water. Drug stocks are kept frozen at −70° C., protected from light.

Susceptibility Testing. MICs are determined by the broth microdilution method in accordance with the NCCLS guidelines. In brief, organism suspensions are adjusted to a 0.5 McFarland standard to yield a final inoculum between $3\times10^5$ and $7\times10^5$ CFU/ml. Drug dilutions and inocula are made in sterile, cation adjusted Mueller-Hinton Broth (CAMHB) (Remel) for all but *S. pneumoniae* [CAMHB with 2–5% lysed horse blood (Remel)] and *H. influenzae* [Haemophilus Test Medium (Remel)]. An inoculum volume of 100 μl is added to wells containing 100 μl of broth with 2-fold serial dilutions of drug. All inoculated microdilution trays are incubated in ambient air at 35° C. for 18–24 hours, except for *S. pneumoniae*, and *H. influenzae* (both at 5–10% $CO_2$). Following appropriate incubation, the MIC is determined and the MIC is defined as the lowest concentration of the drug that prevented visible growth.

EXAMPLE 19

In Vivo Pharmacokinetic Studies of Pyridyl Substituted Ketolides

Animal Models. A total of 54 male Sprague-Dawley rats, weighing 200 grams in average, are evaluated for pharmacokinetic studies of representative substituted pyridyl ketolides. Rats are under overnight food restriction and receive water ad libitum. Rats are acclimated for approximately 5 days before antibiotic administration.

Antibiotic Administration. Rats are given bolus administration through intravenous (IV) and oral (PO) routes. Representative substituted pyridyl ketolides and telithromycin, for comparison, are diluted in 0.85% saline to a concentration of 15.0 mg/ml, and the resulting pH is adjusted using 1N acetic acid until the compound is in solution. Approximately 200 μl of the compound solution is administered to the rats. The target dose for IV and PO administration is 5 mg/kg and 15 mg/kg, respectively.

Sample Collection. Plasma and whole lung samples are collected from the rats. Plasma samples are obtained from blood samples by centrifugation at 3000 RPM for 10 min. Heparin is added in the plasma as an anticoagulant. Whole lung samples are homogenized in deionized water. Samples are stored at −80° C. A total of 9 time points are collected in triplicate at 0.083, 0.25, 0.5, 1, 2, 4, 6, 8, and 24 h. Ketolide concentrations in plasma and lung are determined by well-established non-GLP LC-MS-MS methods. PK parameters are estimated from the raw bioanalytical data using WinNolin software (Version 4.0, Pharsight Corporation, CA). The results of this pharmacokinetic assay is shown in Table 2. All representative compounds are compared to telithromycin. These results demonstrate that the representative compounds of the invention exhibit improved pharmacokinetic properties over telithromycin especially with respect to the greater ratio of drug found in the lung compared to that found in plasma.

TABLE 2

| | | PK parameter | | | | | | |
|---|---|---|---|---|---|---|---|---|
| | Dose | AUC, IV | L/P ratio, IV | CL | Vss | t1/2, IV Plasma | t1/2, PO Plasma | F, PO |
| | | | | Unit | | | | |
| | mg/kg | µg·h/mL | — | mL/min/kg | L/kg | h | h | % |
| Telithromycin | IV = 5; PO = 15 | 2.5 | 16 | 100 | 5 | 1.0 | 1.5 | 11 |
| Cmpd B | IV = 5; PO = 15 | 1.7 | 27 | 48 | 6.5 | 1.8 | 3.3 | 54 |
| Cmpd D | IV = 5; PO = 15 | 3.0 | 32 | 25 | 4.3 | 2.1 | — | 100 |
| Cmpd E | IV = 5; PO = 15 | 2.2 | 29 | 38 | 5.6 | 1.6 | 3.3 | 86 |

Abbreviations: IV (intraveneous dosing); L/P (ratio of drug in lung/plasma); L/P ratio, IV (L/P after IV dosing); CL (clearance of the compound from plasma); Vss (volume of distribution); F (% bioavailability); and PO (oral dosing).

While the preferred embodiment of the invention has been illustrated and described, it will be appreciated that various changes can be made therein without departing from the spirit and scope of the invention.

What is claimed is:

1. A compound having the formula (A):

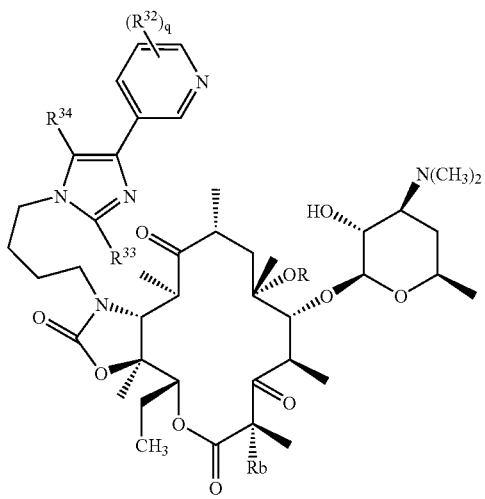

or a pharmaceutically acceptable salt or ester thereof, wherein

A) R is selected from the group consisting of
(1) hydrogen;
(2) methyl substituted with a moiety selected from the group consisting of
 (a) —CN,
 (b) —F,
 (c) —CO$_2$R$^{10}$, wherein R$^{10}$ is C$_1$–C$_3$-alkyl or aryl substituted with C$_1$–C$_3$-alkyl, or heteroaryl substituted with C$_1$–C$_3$-alkyl,
 (d) —S(O)$_n$R$^{10}$—, wherein n is 0, 1, or 2 and R$^{10}$ is as previously defined,
 (e) —NH—C(O)R$^{10}$, wherein R$^{10}$ is as previously defined,
 (f) —NH—C(O)NR$^{11}$R$^{12}$, wherein R$^{11}$ and R$^{12}$ are independently selected from hydrogen, C$_1$–C$_3$-alkyl, C$_1$–C$_3$-alkyl substituted with aryl, substituted aryl, heteroaryl, and substituted heteroaryl,
 (g) aryl,
 (h) substituted aryl,
 (i) heteroaryl, and
 (j) substituted heteroaryl;
(3) C$_1$–C$_{12}$ alkyl;
(4) C$_2$–C$_{12}$-alkyl substituted with one or more substituents selected from the group consisting of
 (a) halogen,
 (b) hydroxy,
 (c) C$_1$–C$_3$-alkoxy,
 (d) C$_1$–C$_3$-alkoxy-C$_1$–C$_3$-alkoxy,
 (e) oxo,
 (f) —O—SO$_2$-(substituted C$_1$–C$_6$-alkyl),
 (g) —N$_3$,
 (h) —CHO,
 (i) —NR$^{13}$R$^{14}$, wherein R$^{13}$ and R$^{14}$ are selected from the group consisting of
  (i) hydrogen,
  (ii) C$_1$–C$_{12}$-alkyl,
  (iii) substituted C$_1$–C$_{12}$-alkyl,
  (iv) C$_2$–C$_{12}$-alkenyl,
  (v) substituted C$_2$–C$_{12}$-alkenyl,
  (vi) C$_2$–C$_{12}$-alkynyl,
  (vii) substituted C$_2$–C$_{12}$-alkynyl,
  (viii) aryl,
  (ix) C$_3$–C$_8$-cycloalkyl,
  (x) substituted C$_3$–C$_8$-cycloalkyl,
  (xi) substituted aryl,
  (xii) C$_3$–C$_{12}$-heterocycloalkyl,
  (xiii) substituted C$_3$–C$_{12}$-heterocycloalkyl,
  (xiv) C$_1$–C$_{12}$-alkyl substituted with aryl,
  (xv) C$_1$–C$_{12}$-alkyl substituted with substituted aryl,
  (xvi) C$_1$–C$_{12}$-alkyl substituted with C$_3$–C$_{12}$-heterocycloalkyl,
  (xvii) C$_1$–C$_{12}$-alkyl substituted with substituted C$_3$–C$_{12}$-heterocycloalkyl,
  (xviii) C$_1$–C$_{12}$-alkyl substituted with C$_3$–C$_8$-cycloalkyl,
  (xix) C$_1$–C$_{12}$-alkyl substituted with substituted C$_3$–C$_8$-cycloalkyl,
  (xx) heteroaryl, (xxi) substituted heteroaryl,
(xxii) $C_1$–$C_{12}$-alkyl substituted with heteroaryl, and
(xxiii) $C_1$–$C_{12}$-alkyl substituted with substituted heteroaryl;
or $R^{13}$ and $R^{14}$ are taken together with the atom to which they are attached to form a 3- to 10-membered heterocycloalkyl ring which may optionally be substituted with one or more substituents independently selected from the group consisting of
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(viii) $C_1$–$C_3$-alkoxy-$C_1$–$C_3$-alkyl;
(j) —$CO_2R^{10}$, wherein $R^{10}$ is as previously defined,
(k) —$C(O)NR^{11}R^{12}$, wherein $R^{11}$ and $R^{12}$ are as previously defined,
(l) =N—O—$R^{10}$, wherein $R^{10}$ is as previously defined,
(m) —CN,
(n) —O—$S(O)_nR^{10}$ wherein n is 0, 1, or 2 and $R^{10}$ is as previously defined,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) $C_3$–$C_{12}$-heterocycloalkyl,
(w) substituted $C_3$–$C_{12}$-heterocycloalkyl,
(x) —NH—$C(O)R^{10}$, wherein $R^{10}$ is as previously defined,
(y) —NH—$C(O)NR^{11}R^{12}$, wherein $R^{11}$ and $R^{12}$ are as previously defined,
(z) =N—$NR^{13}R^{14}$, wherein $R^{13}$ and $R^{14}$ are as previously defined,
(aa) =N—$R^9$, wherein $R^9$ is selected from the group consisting of:
(i) $C_1$–$C_{12}$-alkyl optionally substituted with a substituent selected from the group consisting of
(a) aryl,
(b) substituted aryl,
(c) heteroaryl, and
(d) substituted heteroaryl,
(ii) aryl,
(iii) substituted aryl,
(iv) heteroaryl,
(v) substituted heteroaryl, and
(vi) $C_3$–$C_{12}$-heterocycloalkyl,
(bb) =N—NH—$C(O)R^{10}$, wherein $R^{10}$ is as previously defined, and
(cc) =N—NH—$C(O)NR^{11}R^{12}$, wherein $R^{11}$ and $R^{12}$ are as previously defined;
(5) $C_3$-alkenyl substituted with a moiety selected from the group consisting of
(a) hydrogen,
(b) halogen,
(c) —CHO,
(d) —$CO_2R^{10}$, wherein $R^{10}$ is as previously defined,
(e) —$C(O)NR^{11}R^{12}$, wherein $R^{11}$ and $R^{12}$ are as previously defined,
(f) —$C(O)R^9$, wherein $R^9$ is as previously defined,
(g) —CN,
(h) aryl,
(i) substituted aryl,
(j) heteroaryl,
(k) substituted heteroaryl,
(l) —$C_3$–$C_8$-cycloalkyl, and
(m) —$C_1$–$C_{12}$-alkyl substituted with heteroaryl;
(6) $C_4$–$C_{10}$-alkenyl;
(7) $C_4$–$C_{10}$-alkenyl substituted with one or more substituents selected from the group consisting of
(a) halogen,
(b) —$C_1$–$C_3$-alkoxy,
(c) oxo,
(d) —CHO,
(e) —$CO_2R^{10}$, wherein $R^{10}$ is as previously defined,
(f) —$C(O)NR^{11}R^{12}$, wherein $R^{11}$ and $R^{12}$ are as previously defined,
(g) —$NR^{13}R^{14}$, wherein $R^{13}$ and $R^{14}$ are as previously defined,
(h) =N—O—$R^{10}$, wherein $R^{10}$ is as previously defined,
(i) —CN,
(j) —O—$S(O)_nR^{10}$, wherein n is 0, 1, or 2 and $R^{10}$ is as previously defined,
(k) aryl,
(l) substituted aryl,
(m) heteroaryl,
(n) substituted heteroaryl,
(o) —$C_3$–$C_8$-cycloalkyl,
(p) —$C_1$–$C_{12}$-alkyl substituted with substituted heteroaryl,
(q) —NH—$C(O)R^{10}$, wherein $R^{10}$ is as previously defined,
(r) —NH—$C(O)NR^{11}R^{12}$, wherein $R^{11}$ and $R^{12}$ are as previously defined,
(s) =N—$NR^{13}R^{14}$, wherein $R^{13}$ and $R^{14}$ are as previously defined,
(t) =N—$R^9$, wherein $R^9$ is as previously defined,
(u) =N—NH—$C(O)R^{10}$, wherein $R^{10}$ is as previously defined, and
(v) =N—NH—$C(O)NR^{11}R^{12}$, wherein $R^{11}$ and $R^{12}$ are as previously defined;
(8) $C_3$–$C_{10}$-alkynyl;
(9) $C_3$–$C_{10}$-alkynyl substituted with one or more substituents selected from the group consisting of
(a) $C_1$–$C_{12}$-trialkylsilyl,
(b) aryl,
(c) substituted aryl,
(d) heteroaryl, and
(e) substituted heteroaryl; and
(10) $C(O)NR^7R^8$, wherein $R^7$ and $R^8$ are independently selected from hydrogen, $C_1$–$C_{12}$-alkyl, and substituted $C_1$–$C_{12}$-alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH, —N($C_1$–$C_6$-alkyl)-, —N(aryl)-, —N(aryl-$C_1$–$C_6$-alkyl-)-, —N(substituted aryl-$C_1$–$C_6$-alkyl-)-, —N(heteroaryl)-, —N(heteroaryl-$C_1$–$C_6$-alkyl-)-, —N(substituted heteroaryl-$C_1$–$C_6$-alkyl-)-, and —S— or —$S(O)_n$— wherein n is 1 or 2;
B) Rb is hydrogen, halogen, $C_1$–$C_{12}$ alkyl, substituted $C_1$–$C_{12}$-alkyl, or $C_1$–$C_{12}$-alkyl further substituted with one or more halogen groups;
C) Each $R^{32}$ is independently selected from the group consisting of a free, salified, esterified and amidified (1) carboxyl, hydroxyl, halogen, —NO$_2$, —CN, C$_1$–C$_{12}$-alkyl, C$_3$–C$_{12}$-cycloalkyl, C$_2$–C$_{12}$-alkenyl, C$_2$–C$_{12}$-alkynyl, O-alkyl, O-alkenyl, O-alkynyl, S-alkyl, S-alkenyl, S-alkynyl, N-alkyl, N-alkenyl, and N-alkynyl of up to 12 carbon atoms optionally substituted by one or more halogens;
(2) —NR$^{21}$(R$^{22}$),
wherein R$^{21}$ and R$^{22}$ are individually hydrogen or C$_1$–C$_{12}$-alkyl;
(3) —C(O)R$^{23}$,
wherein R$^{23}$ is C$_1$–C$_{12}$-alkyl; and
(4) optionally substituted heteroaryl, O-aryl, S-aryl, and O-substituted-C$_1$–C$_{12}$ alkyl, or S-substituted-C$_1$–C$_{12}$ alkyl;
D) q is 0, 1, 2, 3, or 4; and
E) R$^{33}$ and R$^{34}$ are independently selected from the group consisting of hydrogen, halogen, C$_1$–C$_{12}$ alkyl, and substituted C$_1$–C$_{12}$-alkyl; with the proviso that when q is 0, then R$^{33}$ and R$^{34}$ are not both hydrogen.

2. The compound of claim 1, wherein
A) R is methyl;
B) Rb is hydrogen or halogen;
C) Each R$^{32}$ is independently selected from the group consisting of halogen, C$_1$–C$_{12}$-alkyl, C$_1$–C$_{12}$-alkoxy, C$_1$–C$_{12}$-alkylalkoxy, amino, and —NR$^{21}$(R$^{22}$); and
D) R$^{33}$ and R$^{34}$ are independently selected from the group consisting of hydrogen and C$_1$–C$_{12}$-alkyl.

3. The compound of claim 1, wherein R is methyl.
4. The compound of claim 1, wherein Rb is fluorine.
5. The compound of claim 1, wherein each R$^{32}$ is independently selected from the group consisting of halogen, C$_1$–C$_{12}$-alkyl, C$_1$–C$_{12}$-alkoxy, C$_1$–C$_{12}$-alkylalkoxy, amino, and —NR$^{21}$(R$^{22}$).
6. The compound of claim 5, wherein at least one of R$^{32}$ is 2-chloro, 6-chloro, 2-fluoro, or 6-fluoro.
7. The compound of claim 5, wherein at least one of R$^{32}$ is methyl.
8. The compound of claim 7, wherein at least one of R$^{32}$ is 5-methyl or 6-methyl.
9. The compound of claim 5, wherein at least one of R$^{32}$ is methoxy or ethoxy.
10. The compound of claim 9, wherein at least one of R$^{32}$ is 4-methoxy, 6-methoxy, 4-ethoxy, or 6-ethoxy.
11. The compound of claim 5, wherein at least one of R$^{32}$ is amino, methylamino, or dimethylamino.
12. The compound of claim 11, wherein as least one of R$^{32}$ is 6-amino, 6-methylamino, or 6-dimethylamino.
13. The compound of claim 1, wherein R$^{33}$ and R$^{34}$ are independently selected from the group consisting of hydrogen and C$_1$–C$_{12}$-alkyl.
14. The compound of claim 13, wherein R$^{33}$ is methyl.
15. The compound of claim 13, wherein R$^{34}$ is methyl.
16. The compound of claim 1 wherein
q is 1, R$^{33}$ is hydrogen, R$^{34}$ is hydrogen, and R$^{32}$ is 6-methyl; or
q is 1, R$^{33}$ is hydrogen, R$^{34}$ is hydrogen, and R$^{32}$ is 6-fluoro; or
q is 1, R$^{33}$ is hydrogen, R$^{34}$ is hydrogen, and R$^{32}$ is 6-chloro; or
q is 1, R$^{33}$ is hydrogen, R$^{34}$ is hydrogen, and R$^{32}$ is 6-methoxy; or
q is 1, R$^{33}$ is hydrogen, R$^{34}$ is hydrogen, and R$^{32}$ is 6-ethoxy; or
q is 1, R$^{33}$ is hydrogen, R$^{34}$ is hydrogen, and R$^{32}$ is 6-amino; or
q is 1, R$^{33}$ is hydrogen, R$^{34}$ is hydrogen, and R$^{32}$ is 6-methylamino; or
q is 1, R$^{33}$ is hydrogen, R$^{34}$ is hydrogen, and R$^{32}$ is 6-dimethylamino; or
q is 1, R$^{33}$ is hydrogen, R$^{34}$ is hydrogen, and R$^{32}$ is 4-chloro; or
q is 1, R$^{33}$ is hydrogen, R$^{34}$ is hydrogen, and R$^{32}$ is 4-methoxy; or
q is 1, R$^{33}$ is hydrogen, R$^{34}$ is hydrogen, and R$^{32}$ is 2-chloro; or
q is 1, R$^{33}$ is hydrogen, R$^{34}$ is hydrogen, and R$^{32}$ is 2-methoxy; or
q is 2, R$^{33}$ is hydrogen, R$^{34}$ is hydrogen, one of R$^{32}$ is 5-methyl and the other of R$^{32}$ is 6-chloro; or
q is 1, R$^{33}$ is methyl, R$^{34}$ is hydrogen, and R$^{32}$ is 6-methoxy; or
q is 1, R$^{33}$ is methyl, R$^{34}$ is hydrogen, and R$^{32}$ is 6-chloro; or
q is 1, R$^{33}$ is hydrogen, R$^{34}$ is methyl, and R$^{32}$ is 6-methoxy; or
q is 1, R$^{33}$ is hydrogen, R$^{34}$ is methyl, and R$^{32}$ is 6-chloro.

17. The compound of claim 1 having the formula (B):

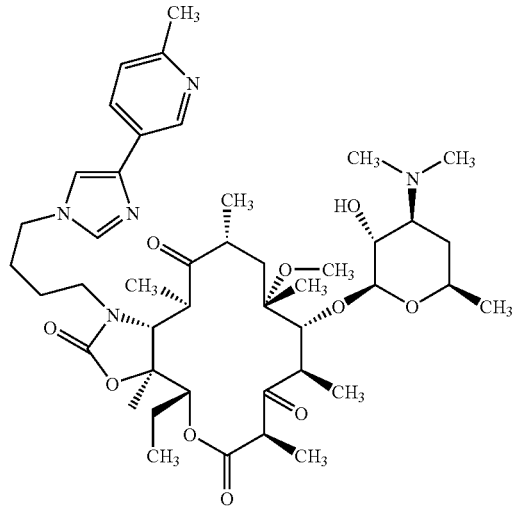

(B)

or a pharmaceutically acceptable salt or ester thereof.

18. The compound of claim 1 having the formula (C):

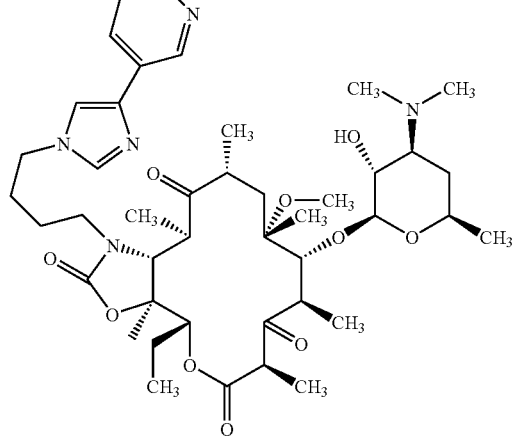

(C)

or a pharmaceutically acceptable salt or ester thereof.

19. The compound of claim 1 having the formula (D):

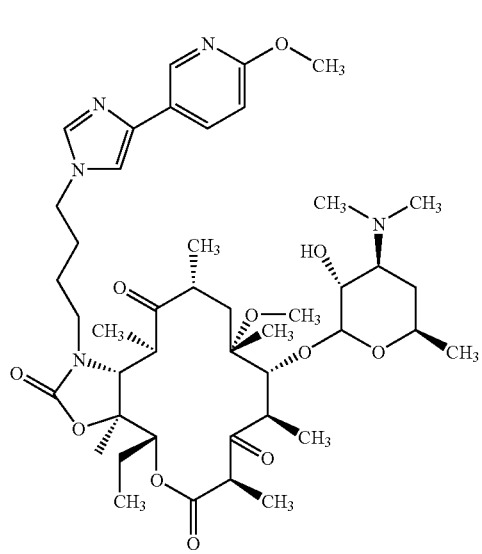

or a pharmaceutically acceptable salt or ester thereof.

20. The compound of claim 1 having the formula (E):

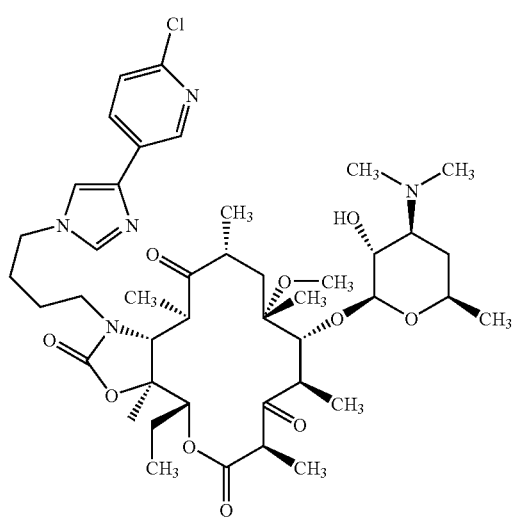

or a pharmaceutically acceptable salt or ester thereof.

21. The compound of claim 1 having the formula (F):

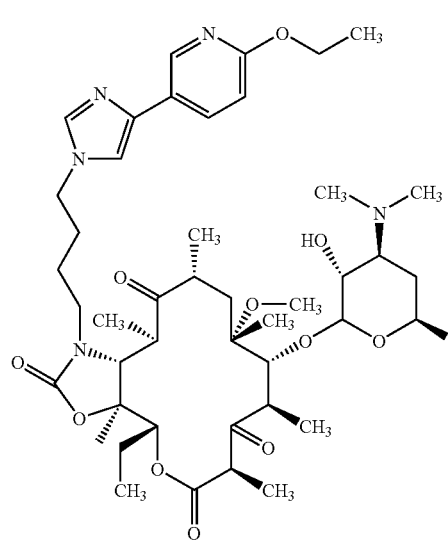

or a pharmaceutically acceptable salt or ester thereof.

22. The compound of claim 1 having the formula (G):

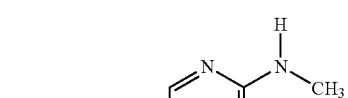

or a pharmaceutically acceptable salt or ester thereof.

23. The compound of claim 1 having the formula (H):

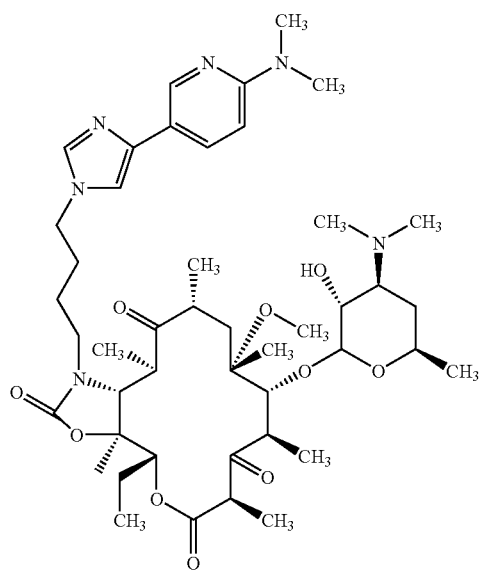

or a pharmaceutically acceptable salt or ester thereof.

24. The compound of claim 1 having the formula (I):

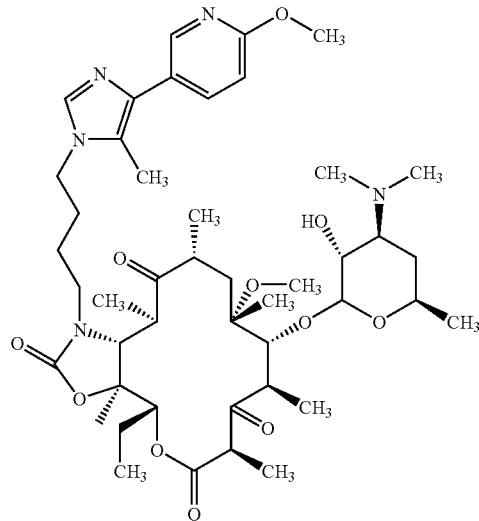

or a pharmaceutically acceptable salt or ester thereof.

25. The compound of claim 1 having the formula (J):

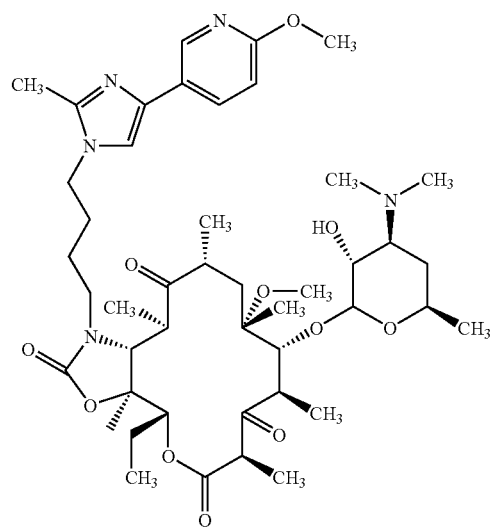

or a pharmaceutically acceptable salt or ester thereof.

26. The compound of claim 1 having the formula (K):

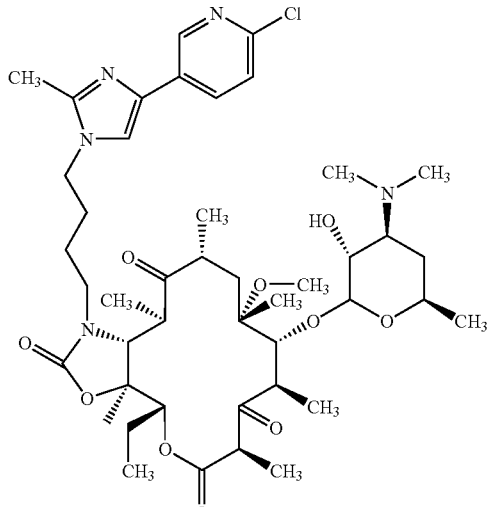

or a pharmaceutically acceptable salt or ester thereof.

27. The compound of claim 1 having the formula (L):

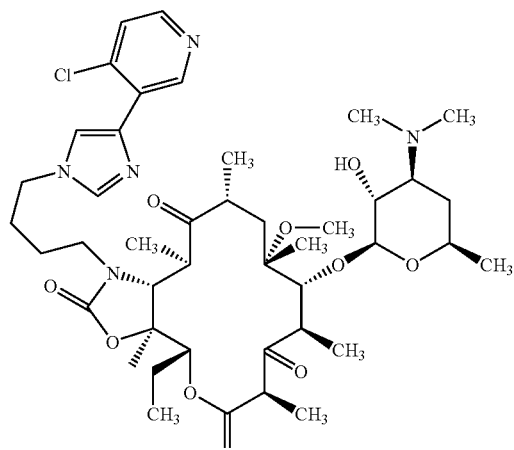

or a pharmaceutically acceptable salt or ester thereof.

28. The compound of claim 1 having the formula (M):

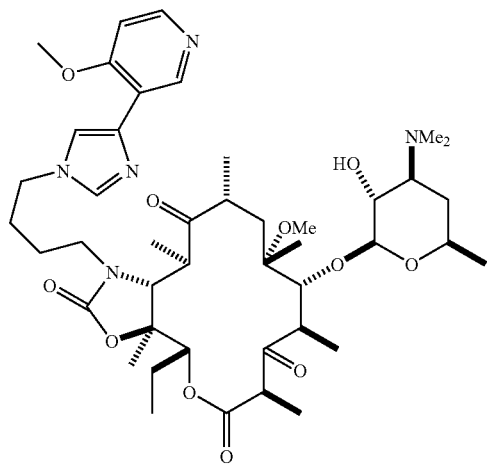

or a pharmaceutically acceptable salt or ester thereof.

29. The compound of claim 1 having the formula (N):

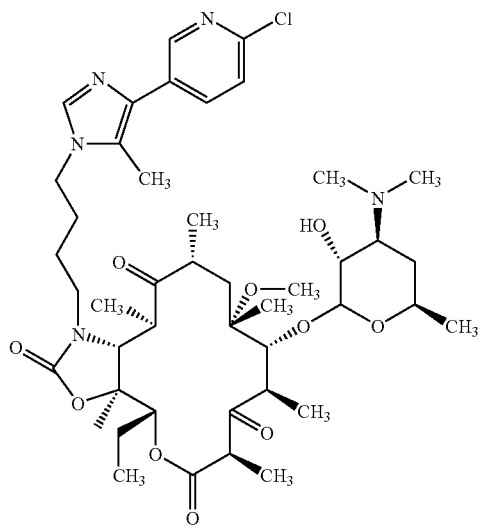

or a pharmaceutically acceptable salt or ester thereof.

30. The compound of claim 1 having the formula (O):

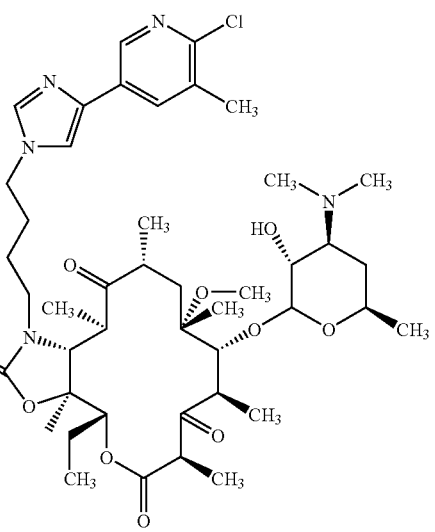

or a pharmaceutically acceptable salt or ester thereof.

31. The compound of claim 1 having the formula (P):

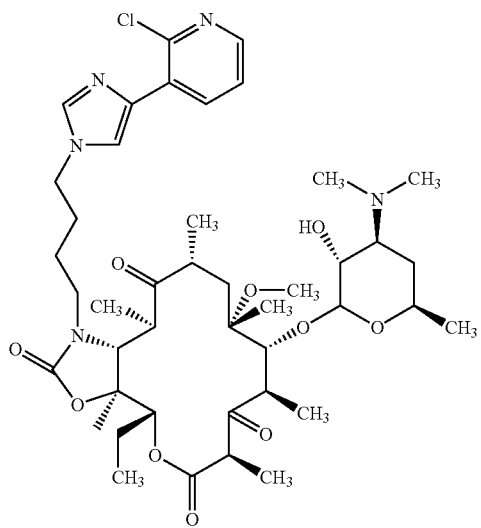

(P)

or a pharmaceutically acceptable salt or ester thereof.

32. The compound of claim 1 having the formula (Q):

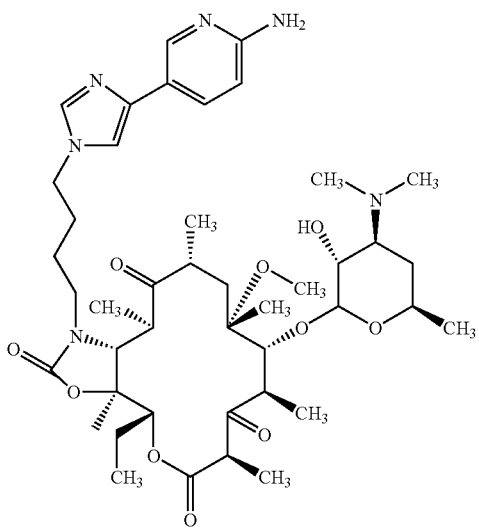

(Q)

or a pharmaceutically acceptable salt or ester thereof.

33. A pharmaceutical composition comprising a therapeutically effective amount of a compound of any one of claims 1, 2, 16, 17, 18, 19, 20, 21, 22, 23, 24, 25, 26, 27, 28, 29, 30, 31, or 32 and a pharmaceutically acceptable carrier.

34. A method of treating bacterial infection in a patient in need thereof comprising administering to said patient a therapeutically effecting amount of a pharmaceutical composition comprising a compound any one of claims 1, 2, 16, 17, 18, 19, 20, 21, 22, 23, 24, 25, 26, 27, 28, 29, 30, 31, or 32 and a pharmaceutically acceptable carrier.

35. A method of making a compound of claim 1, comprising reacting a compound having the following structure:

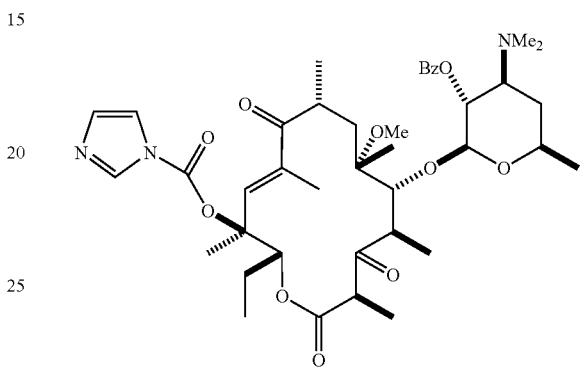

with an amine selected from the group consisting of 4-[4-(6-methyl-pyridin-3-yl)-imidazol-1-yl]-butylamine, 4-[4-(6-fluoro-pyridin-3-yl)-imidazol-1-yl]-butylamine, 4-[4-(6-methoxy-pyridin-3-yl)-imidazol-1-yl]-butylamine, 4-[4-(6-chloro-pyridin-3-yl)-imidazol-1-yl]-butylamine, 4-[4-(6-ethoxy-pyridin-3-yl)-imidazol-1-yl]-butylamine, {5-[1-(4-aminobutyl)imidazol-4-yl](2-pyridyl)}methylamine, {5-[1-(4-aminobutyl)imidazol-4-yl](2-pyridyl)}dimethylamine, 4-[4-(6-methoxy(3-pyridyl))-5-methylimidazolyl]butylamine, 4-[4-(6-methoxy(3-pyridyl))-2-methylimidazolyl]butylamine, 4-[4-(6-chloro-(3-pyridyl))-2-methylimidazolyl]butylamine, 4-[4-(4-chloro-3-pyridyl)imidazolyl]butylamine, 4-[4-(4-methoxy-3-pyridyl)imidazolyl]butylamine, 4-[4-(6-chloro(3-pyridyl))-5-methylimidazolyl]butylamine, 4-[4-(6-chloro-5-methyl-3-pyridyl)imidazolyl]butylamine, 4-[4-(2-chloro-3-pyridyl)imidazolyl]butylamine, and 5-[1-(4-amino-butyl)-1H-imidazol-4-yl]-pyridin-2-ylamine under conditions sufficient to form a cyclized carbamate compound; and removing the benzoyl group.

* * * * *